(12) United States Patent
Bindra

(10) Patent No.: US 10,882,822 B2
(45) Date of Patent: Jan. 5, 2021

(54) USE OF COMPOUNDS FOR MAKING PRODUCTS WITH AT LEAST ONE N-HALAMINE PRECURSOR GROUP AND AT LEAST ONE CATIONIC CENTER

(71) Applicant: Exigence Technologies Inc., Winnipeg (CA)

(72) Inventor: Gurmeet S. Bindra, Winnipeg (CA)

(73) Assignee: UNIVERSITY OF MANITOBA, Winnipeg (CA)

( * ) Notice: Subject to any disclaimer, the term of this patent is extended or adjusted under 35 U.S.C. 154(b) by 0 days.

(21) Appl. No.: 16/315,585

(22) PCT Filed: Jul. 6, 2017

(86) PCT No.: PCT/CA2017/050819
§ 371 (c)(1),
(2) Date: Jan. 4, 2019

(87) PCT Pub. No.: WO2018/006175
PCT Pub. Date: Jan. 11, 2018

(65) Prior Publication Data
US 2019/0300481 A1 Oct. 3, 2019

Related U.S. Application Data

(60) Provisional application No. 62/358,621, filed on Jul. 6, 2016.

(51) Int. Cl.
| C07D 211/58 | (2006.01) |
| C07D 405/14 | (2006.01) |
| C07D 401/12 | (2006.01) |
| C07D 405/12 | (2006.01) |

(52) U.S. Cl.
CPC .......... *C07D 211/58* (2013.01); *C07D 401/12* (2013.01); *C07D 405/12* (2013.01); *C07D 405/14* (2013.01)

(58) Field of Classification Search
CPC .................................................. C07D 211/58
USPC ....................................................... 546/223
See application file for complete search history.

(56) References Cited

U.S. PATENT DOCUMENTS 7,858,539 B2 * 12/2010 Li ....................... D06M 13/325
442/123

FOREIGN PATENT DOCUMENTS

| WO | 2013/173905 A1 | 11/2013 | |
| WO | 2017/063091 A1 | 4/2017 | |
| WO | WO 2017063091 | * 4/2017 | ........... C07D 211/58 |
| WO | 2017/079825 A1 | 5/2017 | |

OTHER PUBLICATIONS

Sun, Ind. Eng. Chem. Res. 1994, 33, 168-170.*
Cerkez, Langmuir 2011, 27, 4091-4097 (see Scheme 1 and 2 on p. 4092).*
International Search Report issued in corresponding Application No. PCT/CA2017/050819, dated Sep. 28, 2017.
Written Opinion issued in corresponding Application No. PCT/CA2017/050819, dated Sep. 28, 2017.

* cited by examiner

*Primary Examiner* — Nizal S Chandrakumar
(74) *Attorney, Agent, or Firm* — Chamberlain, Hrdlicka, White, Williams & Aughtry

(57) ABSTRACT

The present disclosure relates to using a compound as a reactant in one or more chemical reactions for making intermediate compounds or reaction-product compounds that includes at least one cyclic N-halamine precursor group and at least one cationic center. The compound has the general formula (1): Wherein Z is either N or Y and when Z is N then $R_1$ and $R_2$ are each independently selected from a group of methyl, ethyl or n-propyl. When Z is Y then R1 and R2 are both nil and Y is selected from Cl, Br and I. The reaction-product compound may have biocidal activity and/ or it may have increased biocidal activity following one or more chemical-modification reactions.

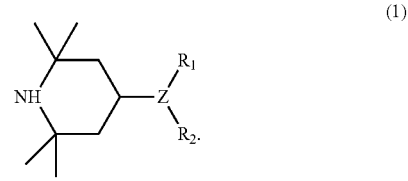

(1)

7 Claims, 92 Drawing Sheets

FIG. 1
Synthesis Reaction A
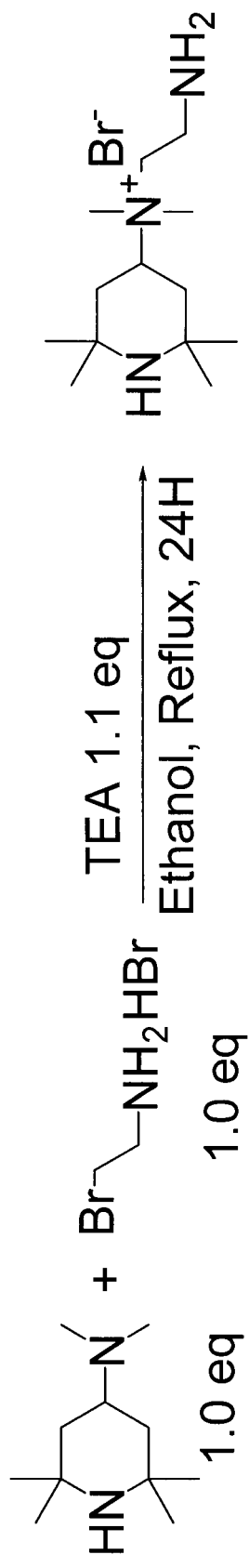
FIG. 1A
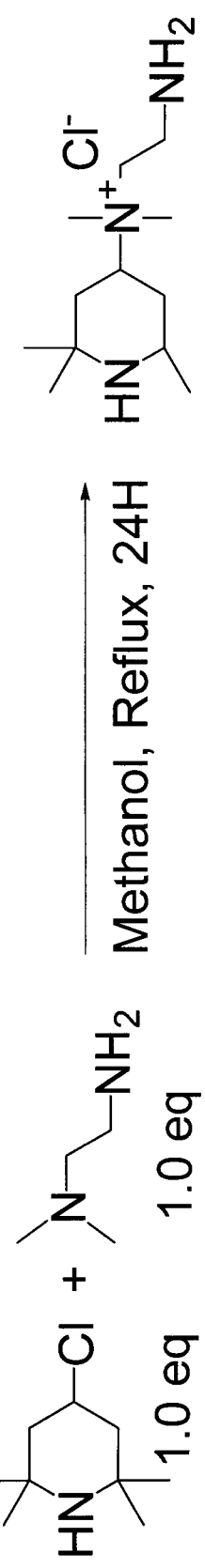
FIG. 1B

Synthesis Reaction C

Synthesis Reaction D

FIG. 5A Synthesis Reaction E

Synthesis Reaction F

Synthesis Reaction G

Synthesis Reaction H

Synthesis Reaction I

PIP-C6-C2-OH

Synthesis Reaction K

Synthesis Reaction L

PIP-C4-BIS-C3-NH2

Synthesis Reaction N

Synthesis Reaction O

FIG. 16A Synthesis Reaction P

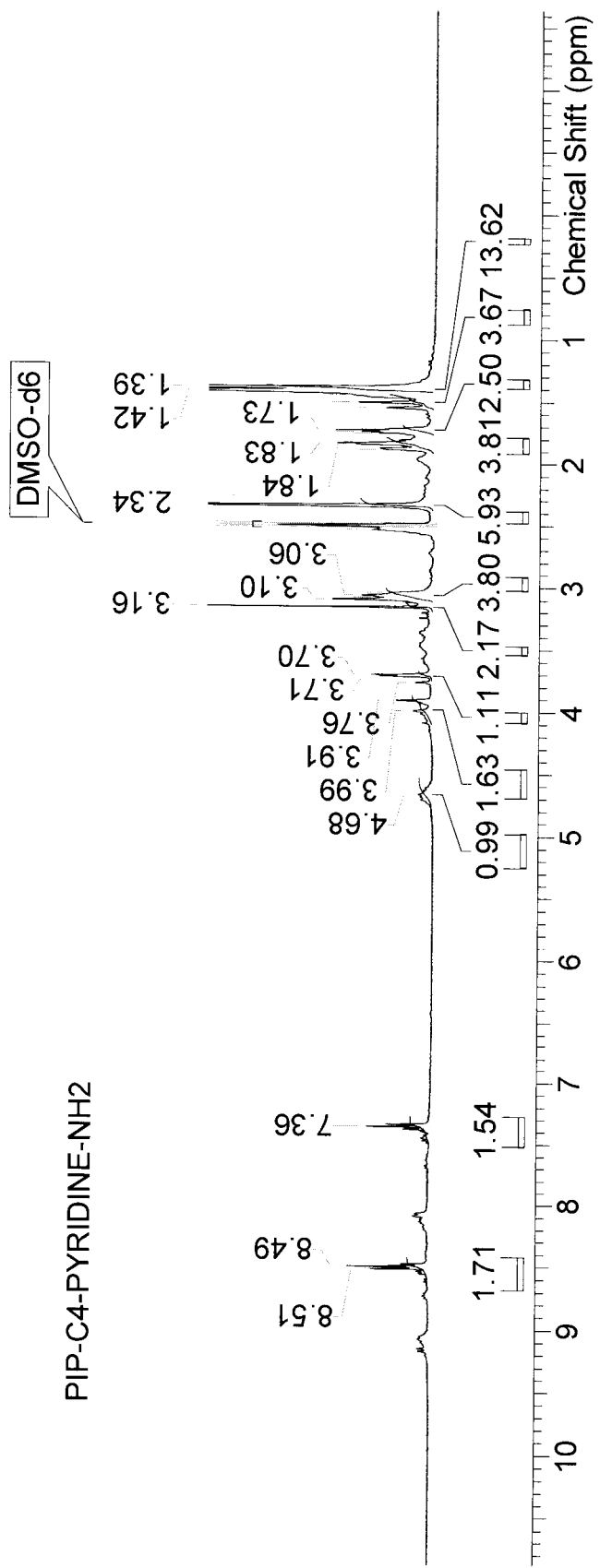
FIG. 16B PIP-C4-PYRIDINE-NH2

Synthesis Reaction Q

Synthesis Reaction R

Synthesis Reaction T

Synthesis Reaction U

Synthesis Reaction V

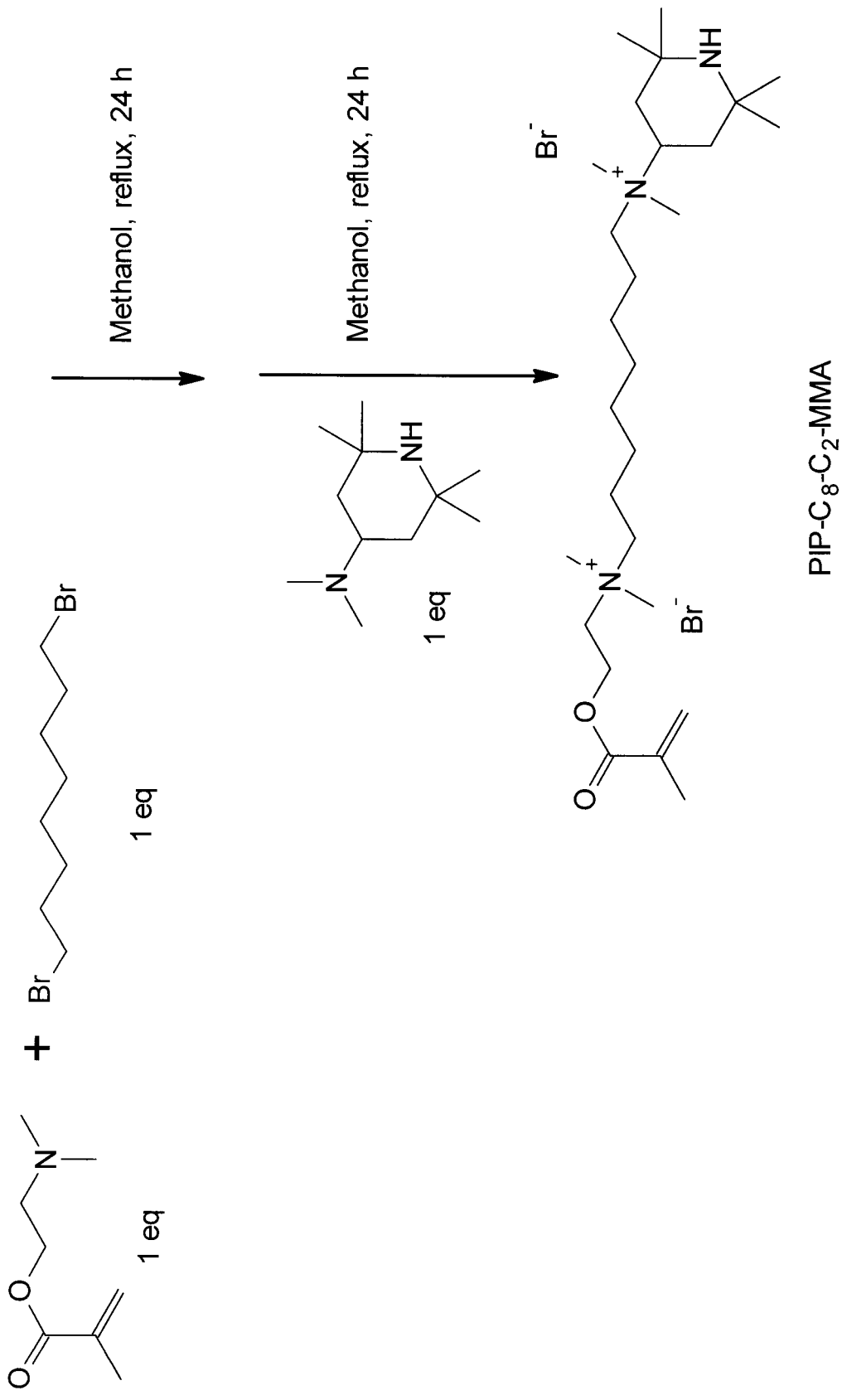

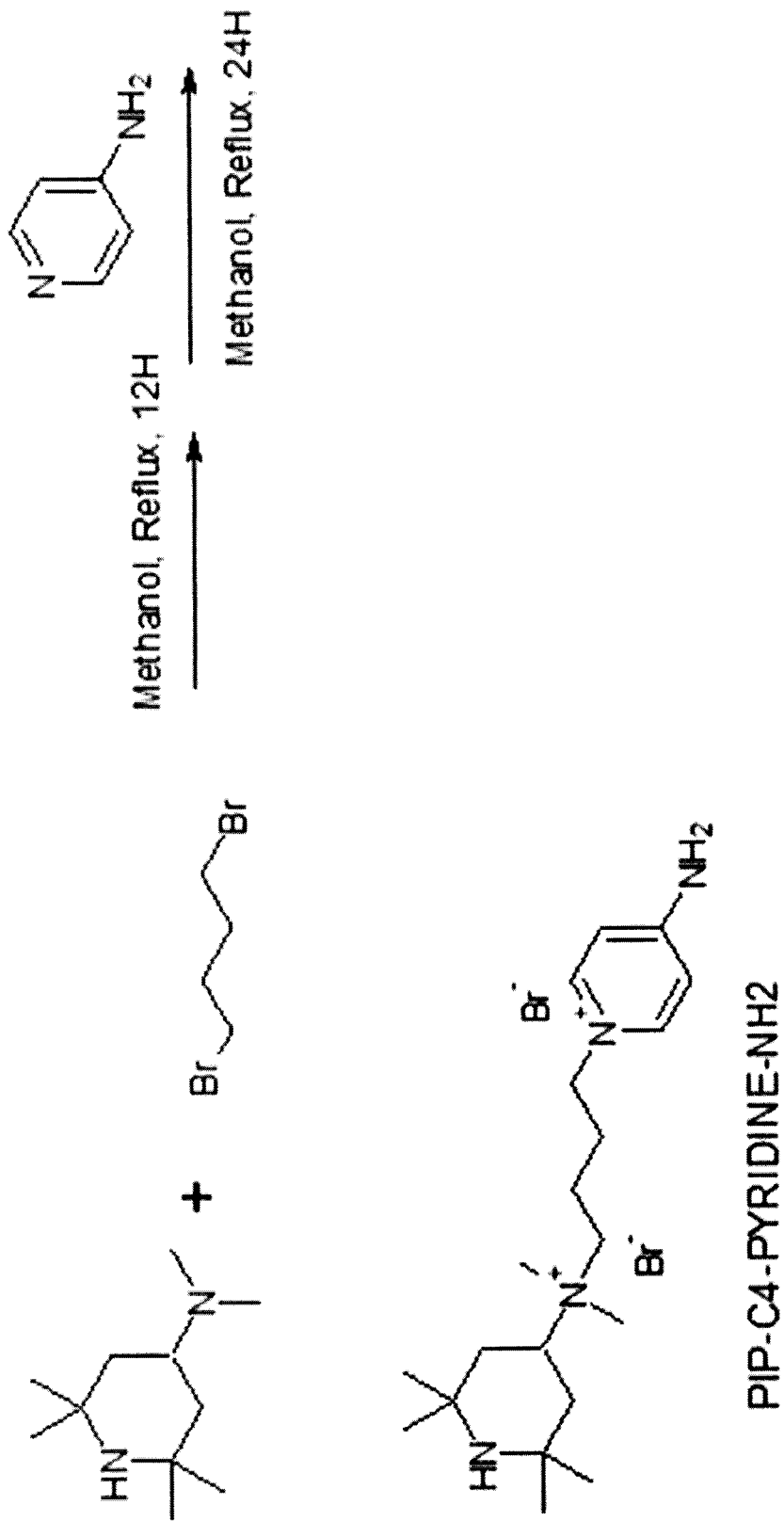

PIP-C3(BIS-OH)-P-C4-P-C3(BIS-OH)-BIS-C3-NH2

PIP-C4-NH2

BIS-PIP-PD

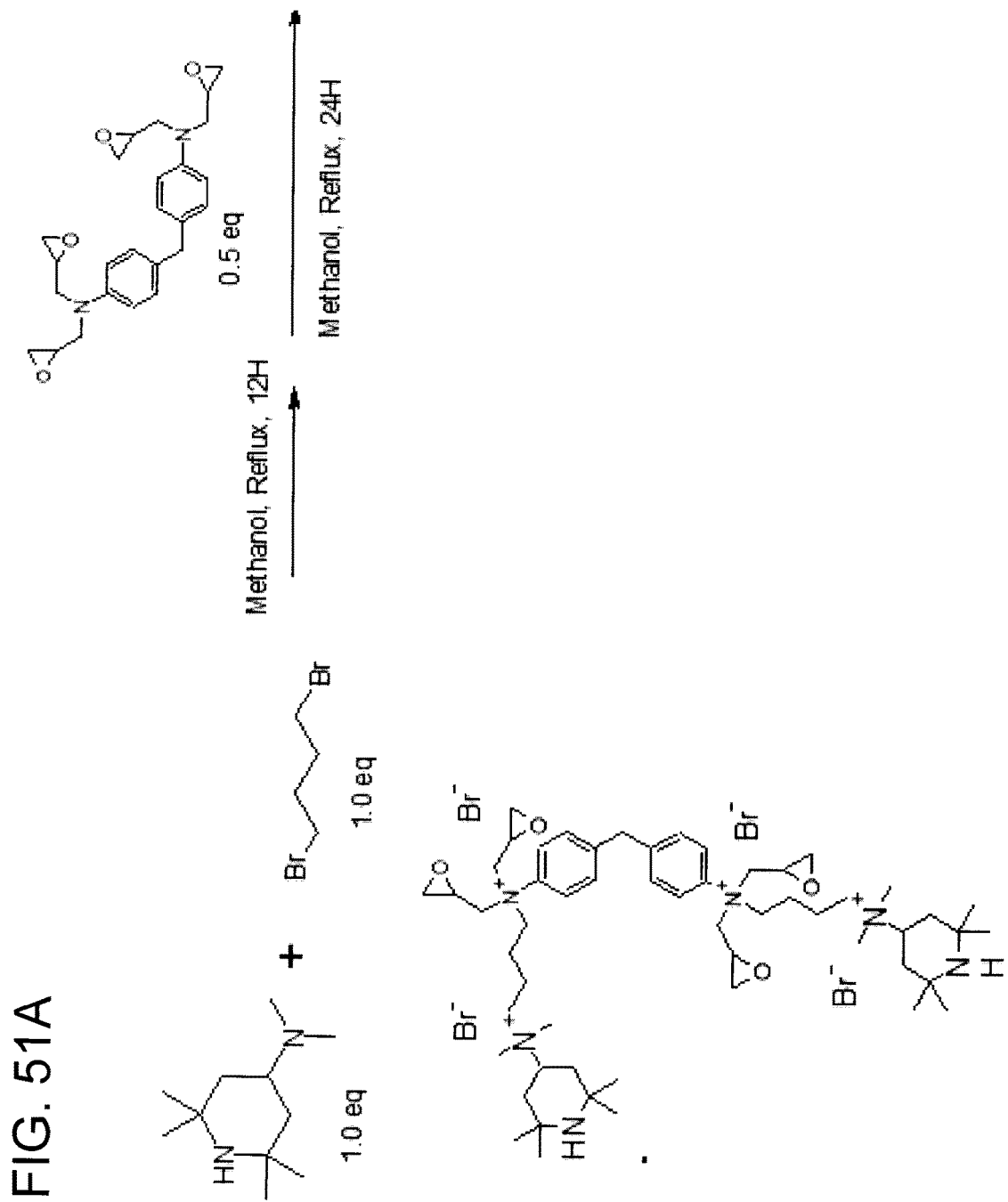

USE OF COMPOUNDS FOR MAKING PRODUCTS WITH AT LEAST ONE N-HALAMINE PRECURSOR GROUP AND AT LEAST ONE CATIONIC CENTER

CROSS-REFERENCE TO RELATED APPLICATIONS

This application claims the benefit of U.S. Provisional Patent Application No. 62/358,621 filed Jul. 6, 2016, the entire disclosure of which is incorporated herein by reference.

TECHNICAL FIELD

This disclosure generally relates to methods of synthesizing intermediate compounds and reaction-product compounds. In particular, the disclosure relates to the use of compounds as a reactant to synthesize reaction-product compounds that have at least one N-halamine precursor group and at least one cationic center.

BACKGROUND

Microorganisms, such as bacteria, archaea, yeast or fungi, can cause disease, spoilage of inventory, process inefficiencies, disruptions of healthy natural environments and infrastructure degradation. More specifically, healthcare-associated infections (HAIs) are a serious and growing challenge to health care systems around the world. HAIs cause over 100,000 deaths annually and have become the 3rd leading cause of death in Canada. It is estimated that in any given year, HAIs directly cost the United States healthcare system between about $30B and about $45B. Added to this challenge is the increasing prevalence of microorganisms that are resistant to currently available antimicrobial intervention products and processes, including preventative approaches (disinfectants used to control environmental contamination) and reactive approaches (remedies including the use of antibiotics). Therefore, it is necessary to deploy biocidal technologies in various environments as a strategy for controlling unwanted levels or types of micro-organisms.

A common approach for disinfecting of both hard and soft surfaces is the use of liquid disinfectants. Selection of a suitable disinfectant for any given application is dependent upon the environment where the disinfectant will be applied. Selection criteria include the types of micro-organisms targeted, contact time for the disinfectant, level of toxicity tolerable in each application, cleanliness (or lack thereof) of the surface to be cleaned, sensitivity of the surface materials to oxidization (i.e., leading to corrosion of the substrate), the presence or absence of biofilms, the amount of organic load present on substrate surfaces, and local regulations that may restrict the use of certain active ingredients within a disinfectant. Some environments are far more challenging to adequately disinfect than others.

It is known to modify soft surfaces, such as textiles, to provide biocidal properties. For example, the antimicrobial properties of silver have been known since at least the 1960s. Specifically, silver nanoparticles possess broad-spectrum antimicrobial activities and exhibit few toxicological side effects. Currently there are commercially available textiles that incorporate silver, for example, there is a LULULEMON® (Lululemon is a registered trademark of Lululemon Athletica Canada Inc.), SILVERSCENT® (Silverscent registered trademark of Lululemon Athletica Inc.) product that incorporates the X-STATIC® (X-static registered trademark of Noble Fiber Technologies, LLC) silver product. Additionally, UNDER ARMOUR® (Under Armour registered trademark of Under Armour, Inc.) markets a Scent Control technology that comprises a blend of at least silver and zinc. The biocidal activity of these silver-incorporated textiles is limited by the amount of silver that is present and available to react with micro-organisms. The amount of silver is finite and may decrease as the textiles are laundered.

It is also known to modify textiles that incorporate polyethylene terephthalate (PET). These modifications may be achieved by forming a surface network of polyacrylamide (PAM) and PET, and then converting immobilized amides within the surface network to N-chloramine. Composite fabrics with such surface networks have been termed PAM-PETs. PAM-PETs have been challenged with different strains of multi-drug resistant bacteria including healthcare acquired *Staphylococcus aureus*, an MRSA (isolate #70065); community-acquired *S. aureus*, also an MRSA (isolate #70527); multi-drug-resistant (MDR) ESBL *E. coli* (isolate #70094); MDR *Pseudomonas aeruginosa* (isolate #73104); and *S. aureus* ATCC 25923. The PAM-PET composite fabric demonstrated close to a 6-log reduction of all the tested bacteria. Furthermore, the N-chloramine on the PAM-PET was evaluated. After 29 regeneration cycles, the PAM-PET (active chlorine 306 ppm) was still able to provide 6-log reduction of HA-MRSA (isolate #70527) within 20 minutes of contact.

International patent application number PCT/CA2013/000491 teaches using forming a semi-interpenetrating network upon a PET surface. The network provides at least one alkynyl group for covalently bonding cyclic amide, azido-5, 5-dimethyl-hydantoin (ADMH). This modified PET sample could bring 7-log reductions of both MDR ESBL #70094 and CA-MRSA #70527. PCT/CA/-2013/00491 also teaches linking the ADMH molecule with a short-chain QAC to create N-(2-azidoethyl)-3-(4, 4-dimethyl-2, 5-dioxoimidazolidin-1-yl)-N, N-dimethylpropan-1-aminium chloride (ADPA) and covalently bonding this molecule onto the PET using the Cu (I)-catalyzed azide-alkyne cyclo addition (CuAAC, usually termed as "click chemistry").

However, forming the surface semi-interpenetrating network as taught by PCT/CA2013/00491, as used in the first step of modification as a priming process, cannot be easily scaled up to industrially relevant levels. For example, the process requires multiple processing steps as well as the introduction of environmentally unfriendly additives, such as a methanol bath at elevated temperature. Additionally, the process requires UV irradiation to promote crosslinking in a methanol saturated environment, which may cause a safety concern. Furthermore, the teaching of PCT/CA2013/00491 may have limited applicability for use with hard surfaces.

SUMMARY

Embodiments of the present disclosure relate to a use of a compound with the general formula (Formula 1):

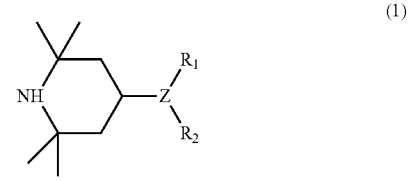

(1)

wherein

Z is either N or Y, when Z is N then $R_1$ and $R_2$ are each independently selected from a group of methyl, ethyl or n-propyl;

when Z is Y then $R_1$ and $R_2$ are both nil and Y is selected from Cl, Br and I; and, wherein the compound is used as a reactant in a chemical reaction for making a reaction-product compound that includes at least one cyclic N-halamine precursor group and at least one cationic center.

Some embodiments of the present disclosure relate to a process for making reaction-product compounds that comprise at least one cyclic N-halamine precursor group and at least one cationic center. The process comprises the step of mixing the compound of Formula 1 with one or more further reactants for producing an intermediary compound or a reaction-product compound.

Some embodiments of the present disclosure relate to a process for making reaction-product compounds that comprise at least one cyclic N-halamine precursor group, at least one cationic center and at least one coating incorporation group (CIG). The process comprises the step of mixing the compound of Formula 1 with one or more further reactants and the one or more further reactants contribute the CIG to the reaction-product compound. In some embodiments of the present disclosure the CIG is selected from the group comprising at least one of: a vinyl group, a hydroxyl group, a vinyl acetate group; an acrylate group; a methacrylate group; a methyl methacrylate group; an epoxide; a thiourea and combinations thereof.

In some embodiments of the present disclosure the CIG may be selected from a group that allows the reaction-product compound to form or incorporate into at least one of: an acetate polymer; a vinyl ester polymer, including a vinyl acetate polymer; a vinyl acetate homopolymer; an acrylate polymer, including a methacrylate polymer; a melamine; a modified melamine; a urethane polymer; a polyurethane polymer; an aliphatic urethane polymer; a polyesters; a self-crosslinking polyesters; an epoxide polymer, including an epoxide-ester polymer, a fluoropolymer; a silicone or silicone derivative polymer; a polyethylene; a polypropylene; a polyvinyl chloride; a polyimide; a polybutylene; a poly(buta-1,3-diene); a polysulfone; a precursor of any of the polymers listed above or any combinations thereof.

BRIEF DESCRIPTION OF THE DRAWINGS

These and other features of the present disclosure will become more apparent in the following detailed description in which reference is made to the appended drawings:

FIG. 1 is an example of a series of synthesis reactions for producing reaction-product compounds according to some embodiments, wherein FIG. 1A shows an example of a reaction for producing a reaction-product compound with an amine functional-group; FIG. 1B shows another example of a reaction for producing the reaction-product compound of FIG. 1A.

FIG. 4 is an example of another synthesis reaction for producing a reaction-product compound with a vinyl functional-group according to an embodiment of the present disclosure that may be used as a component of a textile-coating formulation, wherein FIG. 4A shows the reactants and the reaction-product compound and FIG. 4B shows an example of a proton nuclear magnetic resonance (NMR) spectroscopy data of the reaction-product compound of FIG. 4A;

FIG. 5 is an example of another synthesis reaction series for producing a reaction-product compound with a vinyl functional-group according to an embodiment of the present disclosure that may be used as a component of a textile-coating formulation, wherein FIG. 5A shows the reactants and the reaction-product compound and FIG. 5B shows an example of NMR spectroscopy data of the reaction-product compound of FIG. 5A;

FIG. 9 is an example of another synthesis reaction series for producing a reaction-product compound with a hydroxyl functional-group according to an embodiment of the present disclosure that may be used as a component of a textile-coating formulation, wherein FIG. 9A shows the reactants and the reaction-product compound and FIG. 9B shows an example of NMR spectroscopy data of the reaction-product compound of FIG. 9A;

FIG. 10 is an example of another synthesis reaction series for producing a reaction-product compound with a hydroxyl functional-group according to an embodiment of the present disclosure that may be used as a component of a textile-coating formulation, wherein

FIG. 11 is an example of a synthesis reaction series for producing a reaction-product compound with an amine functional-group according to an embodiment of the present disclosure that may be used as a component of an epoxy coating system, wherein FIG. 11A shows the reactants and the reaction-product compound and FIG. 11B shows an example of NMR spectroscopy data of the reaction-product compound of FIG. 11A;

FIG. 13 is an example of a synthesis reaction series for producing a reaction-product compound with two primary amine functional-groups according to an embodiment of the present disclosure that may be used as a component of an epoxy coating system, wherein FIG. 13A shows the reactants and the reaction-product compound and FIG. 13B shows an example of NMR spectroscopy data of the reaction-product compound of FIG. 13A;

FIG. 14 is an example of a synthesis reaction series for producing a reaction-product compound with one or more thiol-urea analogue functional-groups according to an embodiment of the present disclosure that may be used as a component of an epoxy coating system, wherein FIG. 14A shows the reactants and the reaction-product compound and FIG. 14B shows an example of NMR spectroscopy data of the reaction-product compound of FIG. 14A;

FIG. 15 is an example of another synthesis reaction series for producing a reaction-product compound with a single primary amine functional-group according to an embodiment of the present disclosure that may be used as a component of an epoxy coating system, wherein FIG. 15A shows the reactants and the reaction-product compound and FIG. 15B shows an example of NMR spectroscopy data of the reaction-product compound of FIG. 15A;

FIG. 16 is an example of another synthesis reaction series for producing a reaction-product compound with a single primary amine functional-group according to an embodiment of the present disclosure that may be used as a component of an epoxy coating system, wherein FIG. 16A shows the reactants and the reaction-product compound and FIG. 16B shows an example of NMR spectroscopy data of the reaction-product compound of FIG. 16A;

FIG. 18 is an example of a synthesis reaction series for producing a reaction-product compound with two cationic centers according to an embodiment of the present disclosure that may be used as a component of a liquid disinfectant formulation, wherein FIG. 18A shows an example of a first series of synthesis reactions for producing compounds that can be chemically modified for enhanced biocidal activity.

FIG. 33 is an example of another synthesis reaction series for producing a reaction-product compound according to an embodiment of the present disclosure, wherein FIG. 33A shows the reactants and the reaction-product compound and FIG. 33B shows an example of NMR spectroscopy data of the reaction-product compound of FIG. 33A;

FIG. 34 is an example of another synthesis reaction series for producing a reaction-product compound with a methylmethacrylate CIG according to an embodiment of the present disclosure that may be used as a component of an epoxy coating system, wherein FIG. 34A shows the reactants and the reaction-product compound and FIG. 34B shows an example of NMR spectroscopy data of the reaction-product compound of FIG. 34A;

FIG. 35 is an example of another synthesis reaction series for producing a reaction-product compound with a methylmethacrylate CIG according to an embodiment of the present disclosure, wherein FIG. 35A shows the reactants and the reaction-product compound and FIG. 35B shows an example of NMR spectroscopy data of the reaction-product compound of FIG. 35A;

FIG. 36 is an example of another synthesis reaction series for producing a reaction-product compound with a methylmethacrylate CIG according to an embodiment of the present disclosure, wherein FIG. 36A shows the reactants and the reaction-product compound and FIG. 36B shows an example of NMR spectroscopy data of the reaction-product compound of FIG. 36A;

FIG. 37 is an example of another synthesis reaction series for producing a reaction-product compound with a methylmethacrylate CIG according to an embodiment of the present disclosure, wherein FIG. 37A shows the reactants and the reaction-product compound and FIG. 37B shows an example of NMR spectroscopy data of the reaction-product compound of FIG. 37A;

FIG. 38 is an example of another synthesis reaction series for producing a reaction-product compound with a methylmethacrylate CIG according to an embodiment of the present disclosure, wherein FIG. 38A shows the reactants and the reaction-product compound and FIG. 38B shows an example of NMR spectroscopy data of the reaction-product compound of FIG. 38A;

FIG. 39 is an example of another synthesis reaction series for producing a reaction-product compound with a methylmethacrylate CIG according to an embodiment of the present disclosure, wherein FIG. 39A shows the reactants and the reaction-product compound and FIG. 39B shows an example of NMR spectroscopy data of the reaction-product compound of FIG. 39A;

FIG. 40 is an example of further synthesis reaction series for producing reaction-product compounds with a methylmethacrylate CIG according to an embodiment of the present disclosure, wherein FIG. 40A shows the reactants and the reaction-product compound is referred to herein as PIP-C4-C2-MMA, and FIG. 40B shows the reactants and the reaction-product compound is referred to herein as PIP-C8-C2-MMA;

FIG. 41 is an example of another synthesis reaction series for producing a reaction-product compound with a methylmethacrylate CIG according to an embodiment of the present disclosure, wherein FIG. 41A shows the reactants and the reaction-product compound and FIG. 41B shows an example of NMR spectroscopy data of the reaction-product compound of FIG. 41A;

FIG. 42 is an example of another synthesis reaction series for producing a reaction-product compound with an amine CIG according to an embodiment of the present disclosure, wherein FIG. 42A shows the reactants and the reaction-product compound and FIG. 42B shows an example of NMR spectroscopy data of the reaction-product compound of FIG. 42A;

FIG. 43 is an example of another synthesis reaction series for producing a reaction-product compound with an amine CIG according to an embodiment of the present disclosure, wherein FIG. 43A shows the reactants and the reaction-product compound and FIG. 43B shows an example of NMR spectroscopy data of the reaction-product compound of FIG. 43A;

FIG. 44 is an example of further synthesis reaction series for producing reaction-product compounds with two amine CIGs according to an embodiment of the present disclosure, wherein FIG. 44A shows the reactants and the reaction-product compound is referred to herein as PIP-C4-P-C4-P4-C4-BIS-C3-NH2.

FIG. 45 is an example of further synthesis reaction series for producing reaction-product compounds with one or more amine CIGs according to an embodiment of the present disclosure, wherein FIG. 45A shows the reactants and the reaction-product compound is referred to herein as PIP-C3(BIS-OH)-P-C4-P-C3(BIS-OH)-BIS-C3-NH2.

FIG. 46 is an example of another synthesis reaction series for producing a reaction-product compound with two amine CIGs and a phosphate counter-ion according to an embodiment of the present disclosure, wherein FIG. 46A shows the reactants and the reaction-product compound and FIG. 46B shows an example of NMR spectroscopy data of the reaction-product compound of FIG. 46A;

FIG. 47 is an example of another synthesis reaction series for producing a reaction-product compound with two amine CIGs according to an embodiment of the present disclosure, wherein FIG. 47A shows the reactants and the reaction-product compound and FIG. 47B shows an example of NMR spectroscopy data of the reaction-product compound of FIG. 47A;

FIG. 48 is an example of another synthesis reaction series for producing a reaction-product compound with a hydroxyl CIG according to an embodiment of the present disclosure, wherein FIG. 48A shows the reactants and the reaction-product compound and FIG. 48B shows an example of NMR spectroscopy data of the reaction-product compound of FIG. 48A;

FIG. 49 is an example of further synthesis reaction series for producing reaction-product compounds with a hydroxyl CIG according to an embodiment of the present disclosure, wherein FIG. 49A shows the reactants and the reaction-product compound that is referred to herein a PIP-C4-BIS-C2-OH, FIG. 48B shows the reactants and the reaction-product compound that is referred to herein a PIP-C3-C2-OH, and FIG. 48C is an example of NMR spectroscopy data of the reaction-product compound of FIG. 48B;

FIG. 51 is an example of another synthesis reaction series for producing reaction-product compounds with multiple epoxide CIGs according to an embodiment of the present disclosure, wherein FIG. 51A shows the reactants and the reaction-product compound, and FIG. 48B is an example of NMR spectroscopy data of the reaction-product compound of FIG. 48A;

Figure 1C:
FIG. 1C shows an example of a reaction for producing a reaction-product compound with a hydroxyl functional-group.

The drawings are limited to show three-dimensional chemical compounds in only two dimensions. The present disclosure is not limited to the specific compounds shown in the drawings. The present disclosure also contemplates resonance structures and isomers, such as stereoisomers, diastereomers and enantiomers that have the same functional groups as the compounds shown in the drawings. Furthermore, the present disclosure is not limited to the specific counter ions depicted in the drawings depict. The present disclosure contemplates other suitable counter ions. For example, the $Br^-$ or $Cl^-$ ions depicted may also represent other counter ions, such as other halogen ions, phosphate ions or other similar ions.

DETAILED DESCRIPTION

Some embodiments of the present disclosure relate to methods for making reaction-product compounds that include at least one N-halamine precursor group and at least one cationic center. Some embodiments of the present disclosure relate to different uses of the reaction-product compounds produced by said methods. In some embodiments of the present disclosure, the cationic center comprises one of a quaternized ammonium group, a quaternized phosphonium group or a tertiarized sulfonium group.

Some embodiments of the present disclosure relate to the use of a group of compounds as a reactant in one or more synthesis reactions to make one or more intermediate compounds and one or more reaction-product compounds. These reaction-product compounds comprise at least one N-halamine precursor group and at least one cationic center. The reactant may be used in an initial synthesis reaction or the reactant may be used in a subsequent or intermediate synthesis reaction step within a series of two or more synthesis reactions. Optionally, the reactant may be used in more than one synthesis reaction within a series of two or more synthesis reactions. When the reactant is used in accordance with embodiments of the present disclosure, the reaction-product is one or more chemical compounds that include at least one N-halamine precursor group and at least one cationic center. In some embodiments of the present disclosure, the at least one N-halamine precursor group is selected from a piperidine group or a hydantoin group. In some embodiments of the present disclosure, the at least one cationic center one or more of a nitrogen-based cationic center, a phosphorous-based cationic center or a sulfur-based cationic center. In some embodiments of the present disclosure, there is one cationic center. In some embodiments of the present disclosure, there are at least two cationic centers that are separated by a chain of carbon atoms, saturated or unsaturated hydrocarbons. The chain may include cyclic structures and/or branches, or not. The cationic centers may be the same or different.

Some embodiments of the present disclosure relate to using a reactant to synthesize one or more intermediate compounds and one or more reaction-product compounds. The reaction-product compounds have biocidal activity or they have a potential for biocidal activity or they have a potential for enhanced biocidal activity. Following one or more chemical-modification reactions, the reaction-product compounds may have a greater biocidal activity than prior to the further modification reactions. Furthermore, over time the reaction-product compounds may demonstrate a reduced biocidal activity or no biocidal activity due to various reasons including, but not limited to: exposure to microbes, inhibition caused by organic load, depletion of one or more biocidal components, or combinations thereof. When the reaction-product compounds have a reduced biocidal activity or no biocidal activity, the reaction-product compounds may regain biocidal activity by performing one or more further chemical-modification reactions so that the biocidal activity increases to a greater level than the biocidal activity prior to performing the one or more further chemical-modification reactions. The increase in biocidal activity may also be referred to herein as enhanced biocidal activity. The one or more chemical-modification reactions may be the same as the one or more further chemical-modifications reactions, or not.

Some embodiments of the present disclosure relate to using a reactant to synthesize one or more intermediate compounds and one or more reaction-product compounds with at least one N-halamine precursor group and at least one cationic center. The N-halamine precursor group can be chemically modified to change the N-halamine precursor group to an N-halamine group. Following the chemical modification, the one or more reaction-production compounds may have biocidal activity or enhanced biocidal activity, as compared to the biocidal activity prior to the chemical modification. The chemical modification may occur once or more than once. The N-halamine precursor group may be chemically modified by a halogenation reaction, such as a fluorination, bromination, a chlorination, an iodination or combinations thereof.

Some embodiments of the present disclosure relate to one or more intermediate compounds and one or more reaction-product compounds that are produced by using at least one reactant that is the same. The reactant may enable efficient, high yield reactions that produce a variety of reaction-product compounds. Optionally, the reaction-product compounds may be monomers with a coating incorporation group (CIG). The CIG allows the monomers to form part of or be incorporated into polymers as either homopolymers or heteropolymers, which are also referred to herein as copolymers. Forming part of or becoming incorporated into a polymer may occur by forming one or more chemical bonds between monomers that form the polymer. The polymer structure may be organized so that at least some of the N-halamine precursor groups are external to the polymer structure. This organization allows the polymer to have biocidal activity or the potential for biocidal activity or the potential for enhanced biocidal activity. Furthermore, when the polymer is subjected to a chemical-modification step, the polymer will have greater biocidal activity as compared to prior to the chemical-modification step. The chemical-modification step may be performed once or multiple times so that the biocidal activity of the polymer may be increased once or multiple times.

Some embodiments of the present disclosure relate to the use of at least one specific compound as a reactant in one or more synthesis reactions to make intermediate compounds and reaction-product compounds. The reaction-product compounds comprise at least one N-halamine precursor group, at least one cationic center and at least one CIG. The reaction-product compounds may be used as a component in one or more coating formulations. The one or more CIGs may be selected from a group that comprises one or more of: a vinyl group, a vinyl acetate group, an acrylate group, a methacrylate group, a methyl methacrylate group, an acrylamide group, a styrenic group, a hydroxyl group, an alkyloxy group, an aldehyde group, a ketone group, a carboxy group, an epoxide, an amine group, an imine group, an imide group, an azide group, an amide group, a cyanate group, an isocyanate group, a carbamide group, a thioruea, a thiol group, a sulfinic group, a sulfone group, a sulfoxide group or combinations thereof.

In some embodiments of the present disclosure the CIG may be selected from a group that allows the reaction-product compound to form at least part of or incorporate into at least one of: an acetate polymer; a vinyl ester polymer, including a vinyl acetate polymer; a vinyl acetate homopolymer; an acrylate polymer, including a methacrylate polymer; a melamine; a modified melamine; a urethane polymer; a polyurethane polymer; an aliphatic urethane polymer; a polyesters; a self-crosslinking polyesters; an epoxide polymer, including an epoxide-ester polymer, a fluoropolymer; a silicone or silicone derivative polymer; a polyethylene; a polypropylene; a polyvinyl chloride; a polyimide; a polybutylene; a poly(buta-1,3-diene); a polysulfone; a precursor for any of the components listed above or any combinations thereof. One or more of these coating formulations may be useful for coating soft surfaces and/or hard-surfaces.

At least some of the reaction-product compounds of the present disclosure may be used as a component in a liquid-disinfectant formulation.

The coating formulations and the liquid disinfectant formulation may further include other components such as one or more of a potentiator compound, a cross-linker, a hardener, a diluent, a surfactant or other chemical additives.

Definitions

Unless defined otherwise, all technical and scientific terms used herein have the same meaning as commonly understood by one of ordinary skill in the art to which this disclosure belongs.

As used herein, the term "about" refers to an approximately +/−10% variation from a given value. It is to be understood that such a variation is always included in any given value provided herein, whether or not it is specifically referred to.

As used herein, the term "activity" refers to biocidal activity.

As used herein, the term "biocide" means a chemical compound or a chemical composition or a chemical formulation that can kill or render harmless one or more microbes.

As used herein, the term "cationic center" means an atom within a compound that has a positive charge. The positive charge at a cationic center may be balanced by the presence of one or more negatively-charged ionic species, which may also be referred to herein as a counter-ion. Examples of some atoms that form part of cationic centers described here include but are not limited to: nitrogen, phosphorous and sulfur.

As used herein, the terms "microbe", "microbes", and "micro-organisms" refer to one or more single-celled or multi-cellular microorganisms such as those exemplified by bacteria, archaea, yeast, and fungi.

As used herein, the terms "N-halamine" and "N-halamine group" are used interchangeably to refer to a compound containing one or more nitrogen-halogen covalent bonds that is normally formed by the halogenation of imide and/or amide and/or amine groups within the compound. The presence of the halogen renders the compound biocidal. N-halamines, as referred to in the present disclosure, include both cyclic and acyclic N-halamine compounds.

As used herein, the terms "N-halamine precursor" and "N-halamine precursor group" are used interchangeably to refer to a functional group of a compound that contains an imide, amide or amine that is susceptible to halogenation to form N-halamines or N-halamine groups with biocidal activity. When part of a compound, N-halamine precursors provide the potential for biocidal activity and/or the potential for increased biocidal-activity. Increased biocidal-activity is as compared to the biocidal activity of the compound independent of the halogenation of the N-halamine precursor group.

The terms "halo" or "halogen" by themselves or as part of another substituent, have the same meaning as commonly understood by one of ordinary skill in the art, and preferably refer to chlorine, bromine, iodine or combinations thereof.

The term "quaternary ammonium cation", "quaternary ammonium compound", "quaternary ammonium salt", "QAC", "quat" and "QUAT" may be used interchangeably throughout the present disclosure to refer to ammonium compounds in which four organic groups are linked to a nitrogen atom that produces a positively charged ion (cation) of the structure $NR_4+$.

The terms "organic load", "organic loading", or "organic soil", which may be used interchangeably, as used herein, refer to matter composed of organic compounds that have come from the waste products or the remains of living organisms (plant and animal) or organic molecules made by chemical reactions. Organic load is used herein in a context-dependent manner which may vary per facility, but organic load can be generalized into the following non-limiting examples: animal feces; blood; debris; soil; milk; fats; oils; greases; manure; plant residue etc. These examples of organic load are mainly high in proteins, nitrogen, lipids and carbohydrates.

As used here, the terms "textile", "cloth" and "fabric" may be interchangeable and these terms refer to products made by knitting, weaving or matting of natural fibers, synthetic fibers or combinations thereof.

Embodiments of the present disclosure will now be described by reference to FIG. 1 to FIG. 52, which show examples of synthesis reactions that utilize a family of related compounds as a reactant to produce reaction-product compounds with at least one N-halamine precursor group and at least one cationic center.

The Reactant Compounds

Some embodiments of the present disclosure relate to use of members of a group of compounds as a reactant in different synthesis reactions to synthesize reaction-product compounds that have at least one cyclic N-halamine precursor group and at least one cationic center. In some embodiments of the present disclosure the reactant has the following general formula (Formula 1):

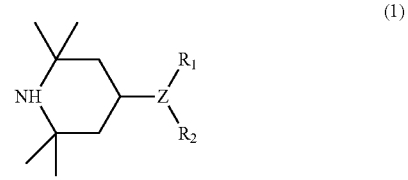

wherein
Z is either N or Y,
when Z is N then $R_1$ and $R_2$ are each independently selected from a group of methyl, ethyl or n-propyl; and
when Z is Y then $R_1$ and $R_2$ are both nil and Y is selected from Cl, Br and I.

The compound of Formula 1 can be used as a reactant in a chemical reaction for making a reaction-product compound that includes at least one cyclic N-halamine precursor group and at least one cationic center.

In at least one embodiment of the present disclosure, the reactant has the general formula (Formula 2):

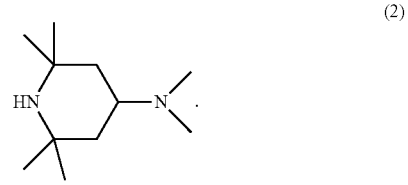

The compound of Formula 2 may also be referred to as N,N-dimethyamino-2,2,6,6-tetramethyl-piperidine (DMATMP).

In at least one embodiment of the present disclosure, the reactant has the general formula (Formula 3):

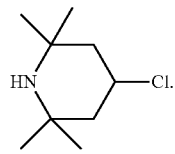

(3)

The compound of Formula 3 may also be referred to as 4-Chloro-2,2,6,6-tetramethyl-piperidine (CITMP).

EXAMPLES

Figure 22:
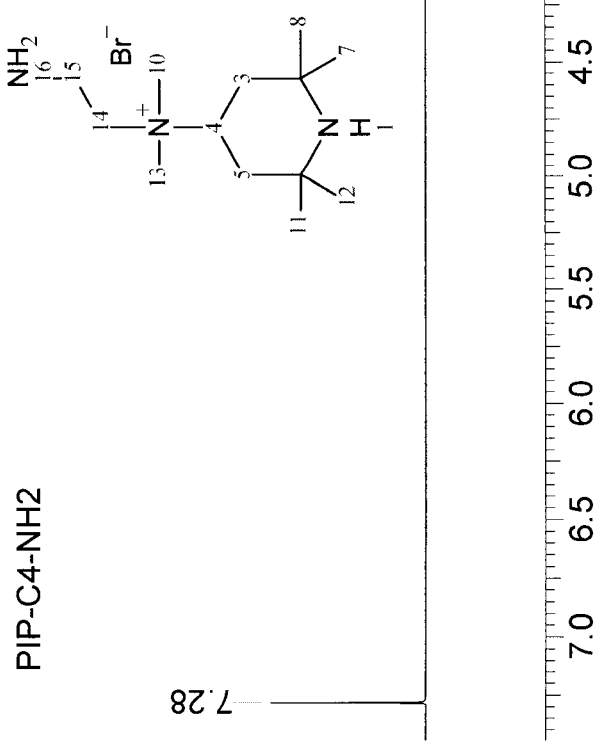
FIG. 22 is an example of NMR spectroscopy data of the reaction-product compound of FIG. 1A.

FIG. 1A shows one example of a use of the compound of Formula 2 to make a reaction-product compound that includes an N-halamine precursor group, a cationic center and an amine CIG. The following were added to a reaction vessel: 1.0 eq of N,N-dimethylamino-2,2,6,6-tetramethyl-piperidine, 1.0 eq of 2-bromoethyleneamine hydrobromide and 1.1 eq of triethylamine dissolved in ethanol and refluxed for 24 hours. The solvent was evaporated and dried under vacuum. The white crystalline product was washed with ethyl acetate and filtered to remove triethylamine hydrobromide salts. The purity of the compound was verified by nuclear magnetic resonance spectroscopy analysis (NMR). Unless otherwise indicated herein, the NMR was proton NMR performed at 300 MHz in CDCl3 for assessing the purity of reaction-product compounds based upon the amount of the reactant, for example DMATMP, DMCITMP or otherwise, that was left over. In this example, the purity was around 98%. In some reaction-product compounds that include phosphorous, separate phosphorous-31 NMR experiments were performed and some examples of the phosphorous-31 NMR spectrum data are provided herein below. The yield of the reaction-product compound shown in FIG. 1A was 99%. FIG. 22 shows an example of the NMR spectrum data obtained.

Figure 23:
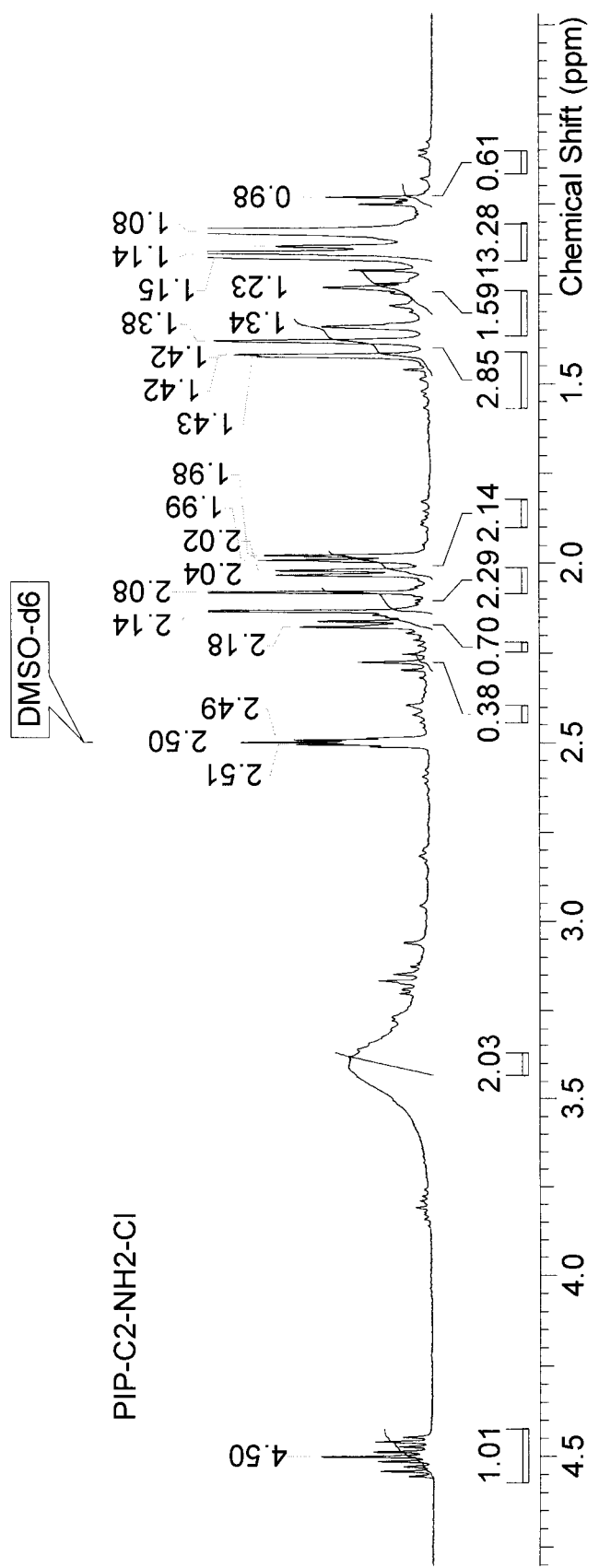
FIG. 23 is an example of NMR spectroscopy data of the reaction-product compound of FIG. 1B.

FIG. 1B shows one example of a use of the compound of Formula 3 to make the same reaction-product compound as in FIG. 1A. The following were added to a reaction vessel: 1.0 eq of 4-Chloro-2,2,6,6-tetramethyl-piperidine, 1.0 eq of N,N-dimethyl ethylenediamine dissolved in methanol and refluxed for 24 hours. The solvent was evaporated and dried under vacuum. The reaction product was washed with ethyl acetate. The purity of the compound was verified by NMR in DMSO, and it was around 98%. The yield of the product was 40%. FIG. 23 shows an example of the NMR spectrum data obtained.

Figure 10:
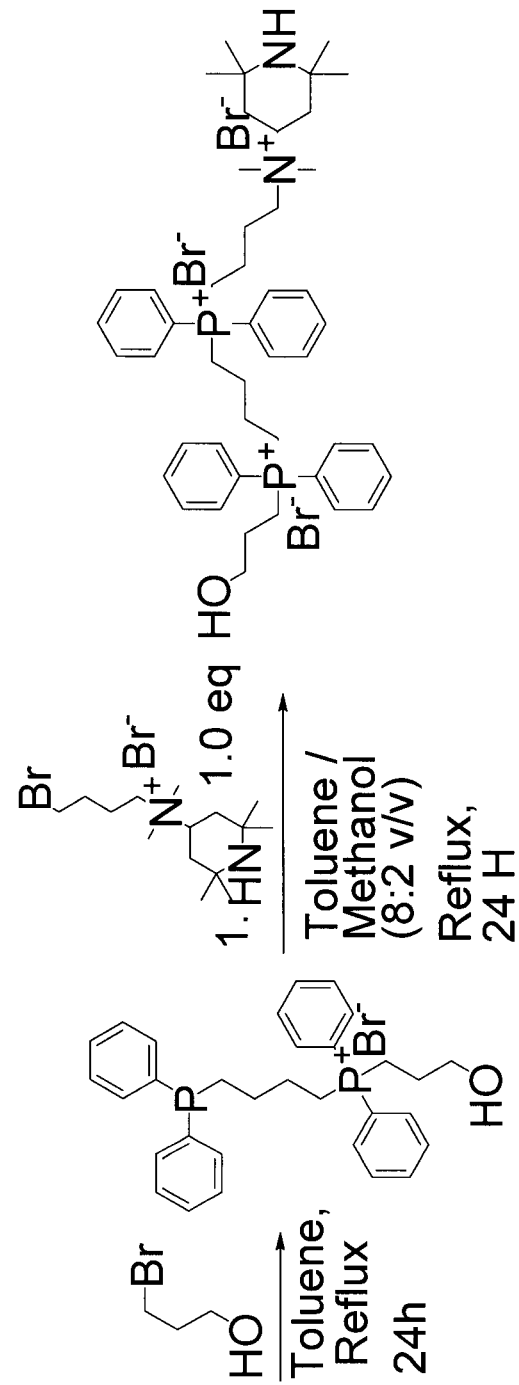
Figure 24:
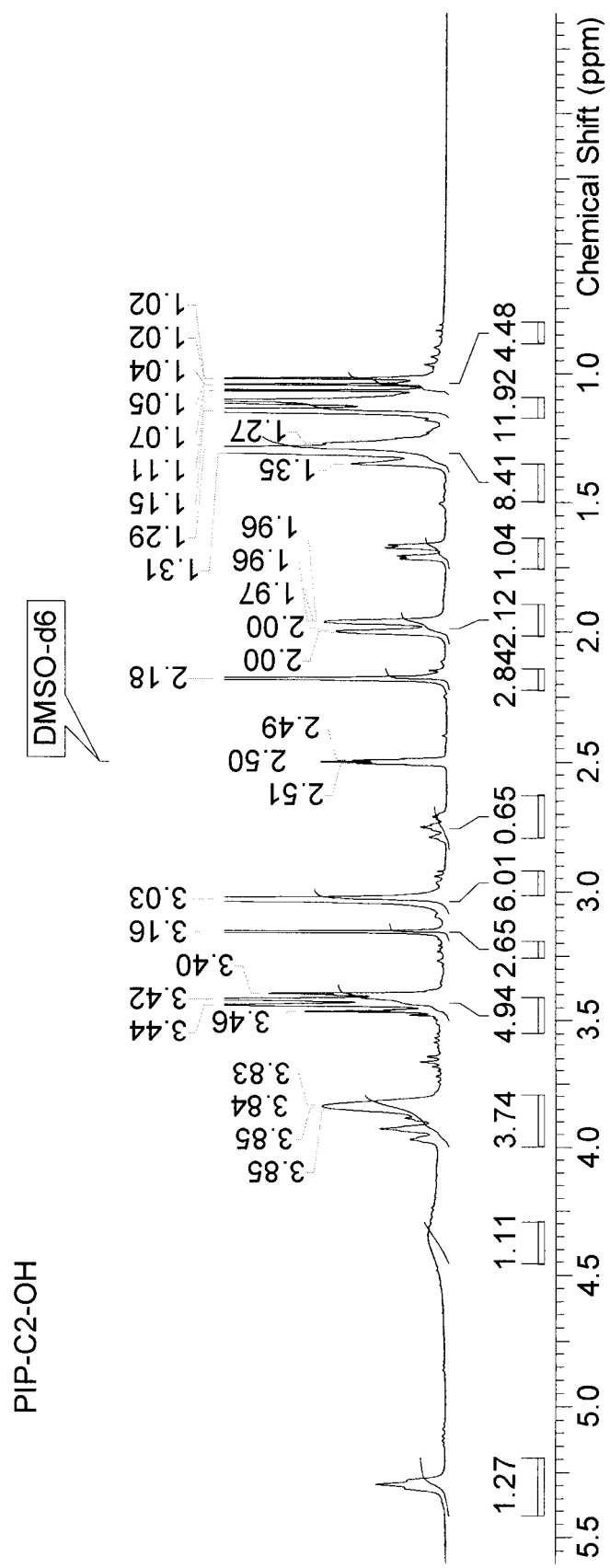
FIG. 24 is an example of NMR spectroscopy data of the reaction-product compound of FIG. 1C.

FIG. 10 shows one example of a use of the compound of Formula 2 to make a reaction-product compound that has an N-halamine precursor group, a cationic center and a hydroxyl CIG. The following were added to a reaction vessel: 1.0 eq of N,N-dimethylamino-2,2,6,6-tetramethyl-piperidine and 1.0 eq of 2-bromoethanol dissolved in methanol and refluxed for 24 hours. The solvent was evaporated and dried under vacuum. The purity of the compound was verified by NMR in DMSO, which was around 98%. The yield of the product was 99%. FIG. 24 shows an example of the NMR spectrum data obtained.

Figure 1D:
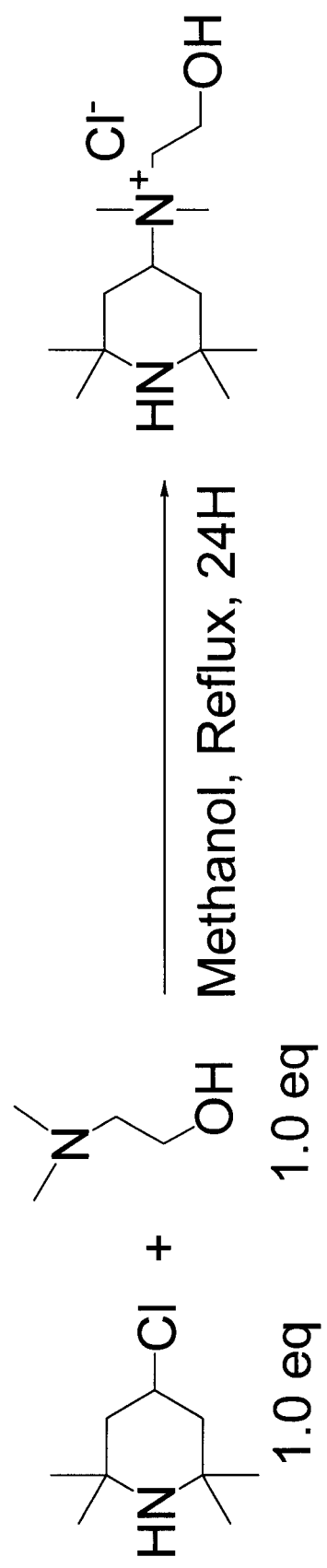
FIG. 1D shows another example of a reaction for producing the reaction-product compound of FIG. 10.
Figure 25:
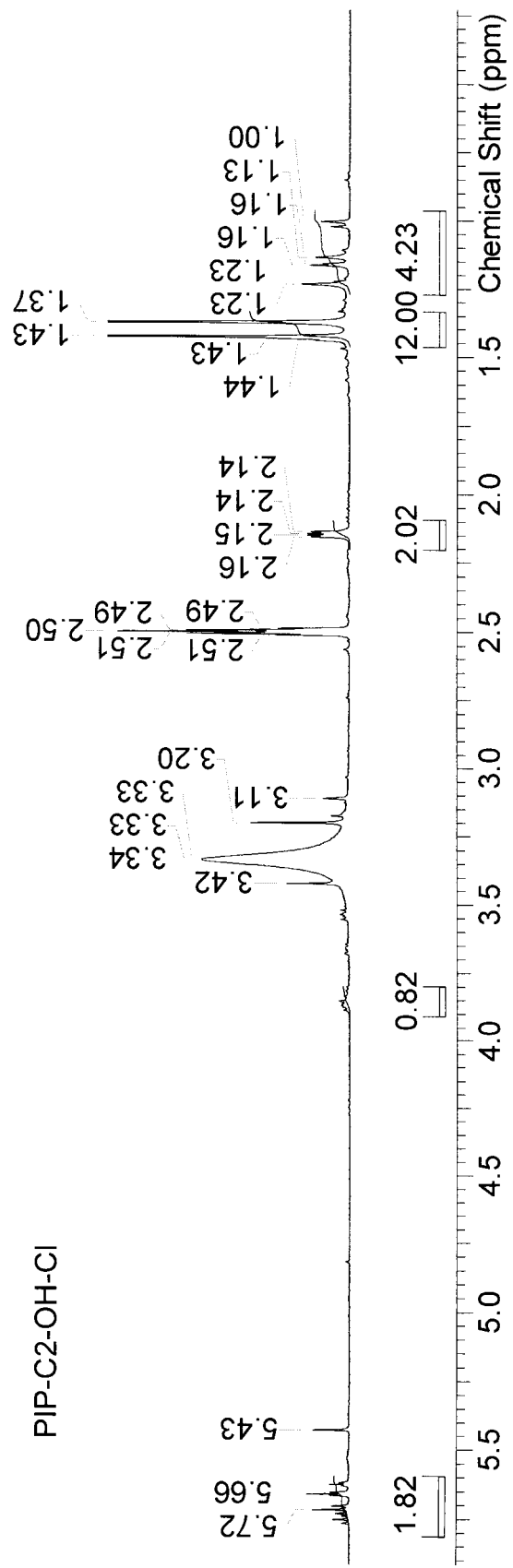
FIG. 25 is an example of NMR spectroscopy data of the reaction-product compound of FIG. 1D.

FIG. 1D shows one example of a use of the compound of Formula 3 to make the same reaction-product compound as in FIG. 10. The following were added to a reaction vessel: 1.0 eq of 4-chloro-2,2,6,6-tetramethyl-piperidine and 1.0 eq of N,N-dimethyl ethanolamine dissolved in methanol and refluxed for 24 hours. The solvent was evaporated and dried under vacuum. Washed with ethyl acetate. The purity of the compound was verified by NMR in DMSO, which was about 98%. The yield of the product was 30%. FIG. 25 shows an example of the NMR spectrum data obtained.

Figure 1E:
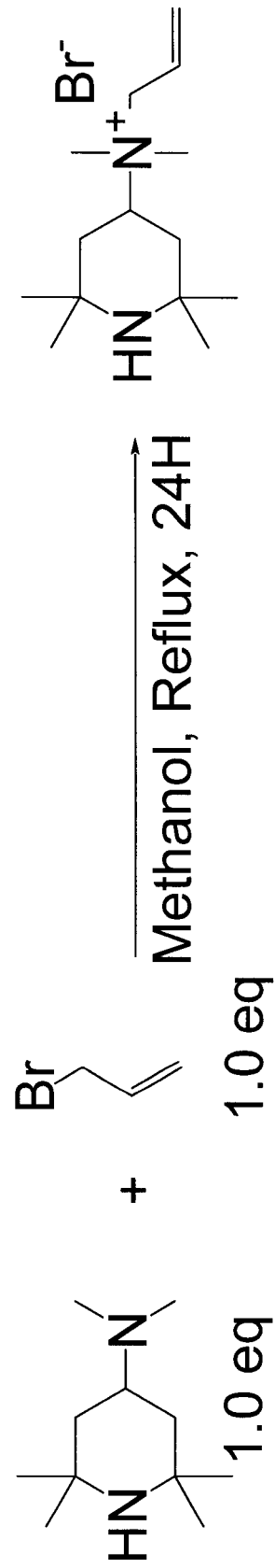
FIG. 1E shows an example of a reaction for producing a reaction-product compound with an vinyl functional-group.
Figure 26:
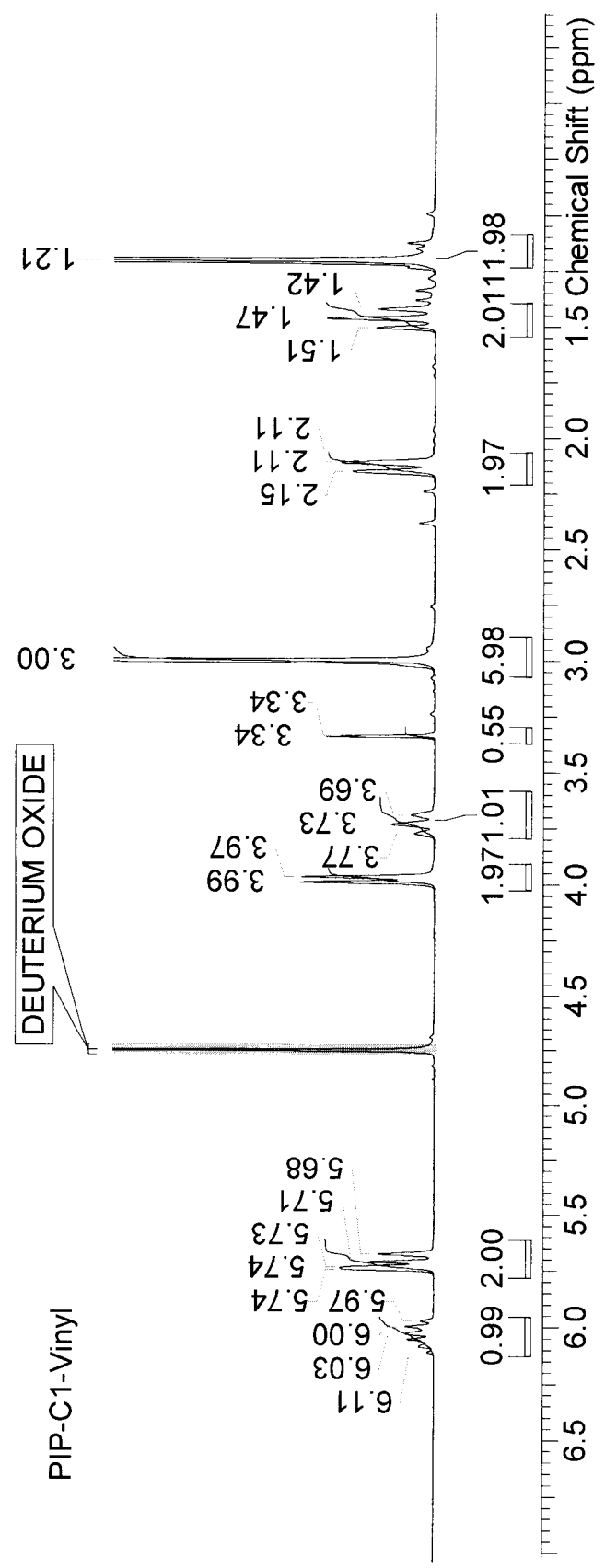
FIG. 26 is an example of NMR spectroscopy data of the reaction-product compound of FIG. 1E.

FIG. 1E shows one example of a use of the compound of Formula 2 to make a reaction-product compound that has an N-halamine precursor group, a cationic center and a vinyl CIG. The following were added to a reaction vessel: 1.0 eq of N,N-dimethylamino-2,2,6,6-tetramethyl-piperidine and 1.0 eq of allyl bromide dissolved in methanol and refluxed for 24 hours. The solvent was evaporated and dried under vacuum. The purity of the compound was verified by NMR in DMSO, which was around 98%. The yield of the product was 99%. FIG. 26 shows an example of the NMR spectrum data obtained.

Figure 1F:
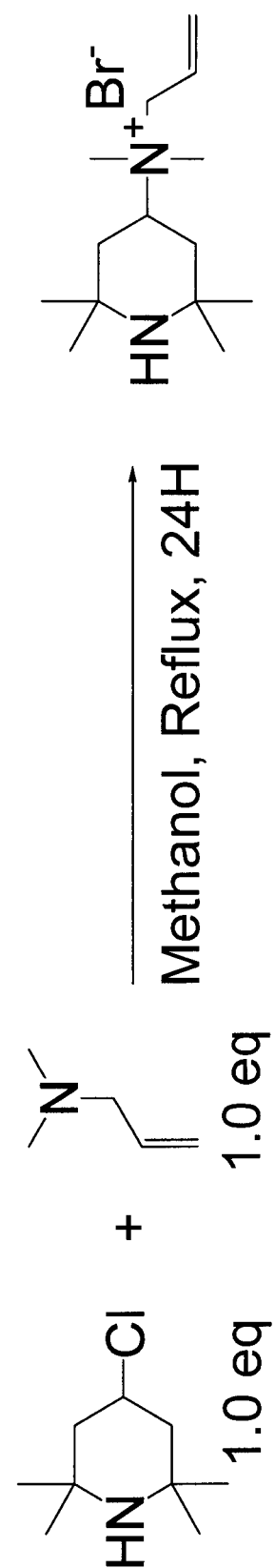
FIG. 1F shows another example of a reaction for producing the reaction-product compound of FIG. 1E.
Figure 27:
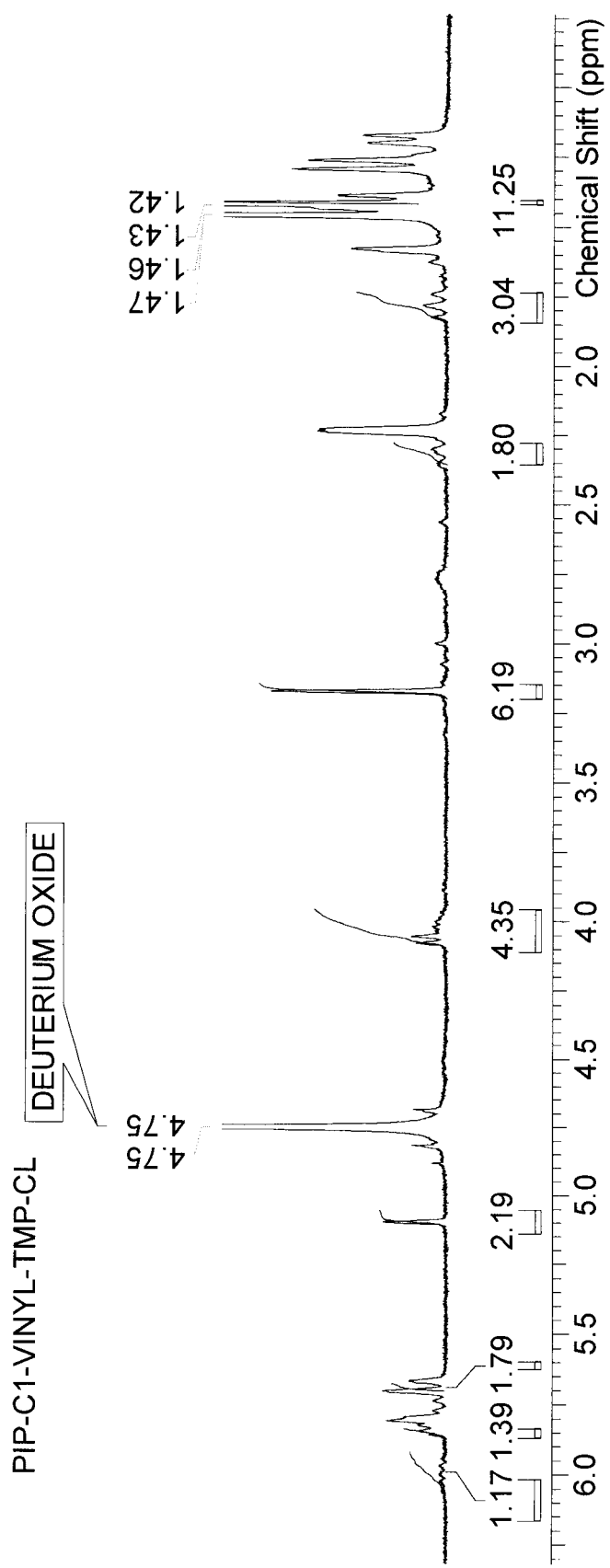
FIG. 27 is an example of NMR spectroscopy data of the reaction-product compound of FIG. 1F.

FIG. 1F shows one example of a use of the compound of Formula 3 to make the same reaction-product compound as in FIG. 1E. The following were added to a reaction vessel: 1.0 eq of 4-chloro-2,2,6,6-tetramethyl-piperidine and 1.0 eq of allyl bromide dissolved in methanol and refluxed for 24 hours. The solvent was evaporated and dried under vacuum. The reaction product was washed with ethyl acetate. The purity of the compound was verified by NMR in DMSO, which was about 90%. The yield of the product was 20%. FIG. 27 shows an example of the NMR spectrum data obtained.

Textile Coatings

The compounds of Formula 1, Formula 2 and Formula 3 can be used as a reactant to synthesize reaction-product compounds that are suitable for coating textiles. DMATMP may be used as a reactant to make reaction-product compounds that have one or more N-halamine precursor groups, one or more cationic centers and at least one of a group of linking terminal-groups. A linking terminal-group may also be referred to herein as a CIG. In some embodiments of the present disclosure the group of CIGs includes at least an amine group, a vinyl group, a hydroxyl group, a vinyl acetate or a thiol group. These reaction-product compounds can be useful as components of a textile-coating formulation.

Some embodiments of the present disclosure relate to one or more textile-coating compounds that include one or more CIGs. The CIG chemically links or bonds the textile-coating compound to another component of the textile-coating formulation that is already linked or bonded to a surface of the textile or to another component that can readily link with or bond to a surface of the textile. When the at least two components of the textile-coating formulation become chemically linked or bonded upon a surface of the textile, the textile may then be considered coated. Alternatively, the textile-coating formulation may comprise the textile-coating compound as substantially the only active ingredient and the textile-coating compound may homopolymerize to form a polymer that is coated on a surface of the textile. Due to the textile-coating compound being coated on the textile, the coated textile has biocidal activity or the potential for biocidal activity or the potential for enhanced biocidal activity.

Some embodiments of the present disclosure relate to textile-coating compounds that have one or more vinyl groups as the linking terminal-group. The one or more vinyl linking terminal-groups may allow the textile-coating compound to chemically link to or bond with another component of the textile-coating formulation.

Some embodiments of the present disclosure relate to textile-coating compounds that have one or more hydroxyl groups as the linking terminal-group. The one or more hydroxyl linking terminal-groups may allow the textile-coating compound to chemically link to or bond with another compound that is part of or bound to the fabric.

Figure 1G:
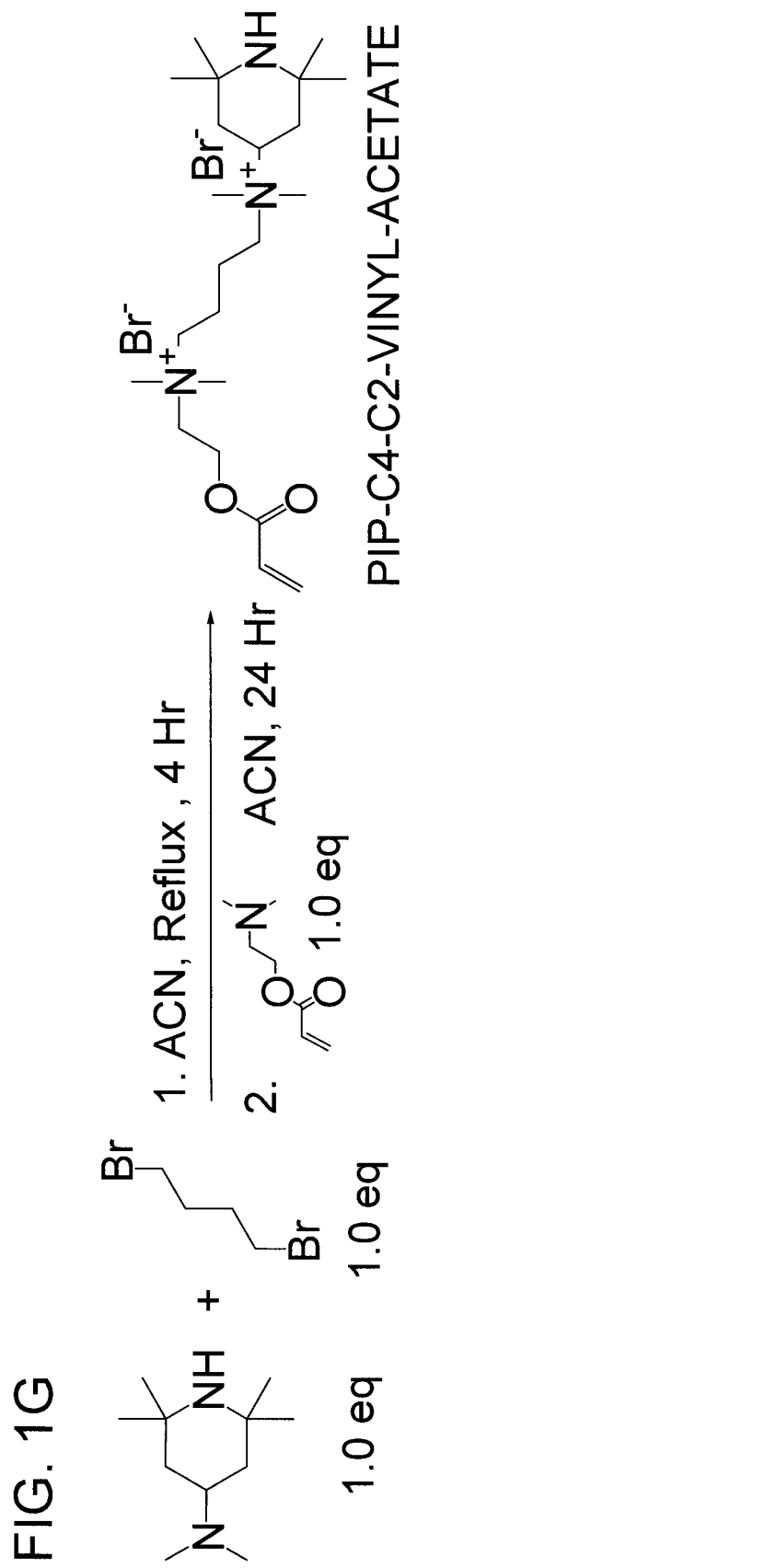
FIG. 1G shows an example of a reaction for producing a reaction-product compound with a vinyl acetate functional-group that may be used as a component of a textile-coating formulation.

FIG. 1G shows one example of a series of reactions that use DMATMP as a reactant for synthesizing a reaction-product compound. This series of reactions is collectively referred to as Synthesis Reaction A and it comprises at least two steps as shown in FIG. 1. The Synthesis Reaction A produces a reaction-product compound with an N-halamine precursor group, two cationic centers and a vinyl CIG. In this example, the reaction-product compound is referred to as PIP-C4-C2-vinyl-acetate. PIP refers to the cyclic N-halamine precursor group piperidine. C4 refers to the four-carbon chain between the two cationic centers, which are QAS in this case. C2 refers to the two carbon chain between the second cationic center and the vinyl acetate group.

Figure 28:
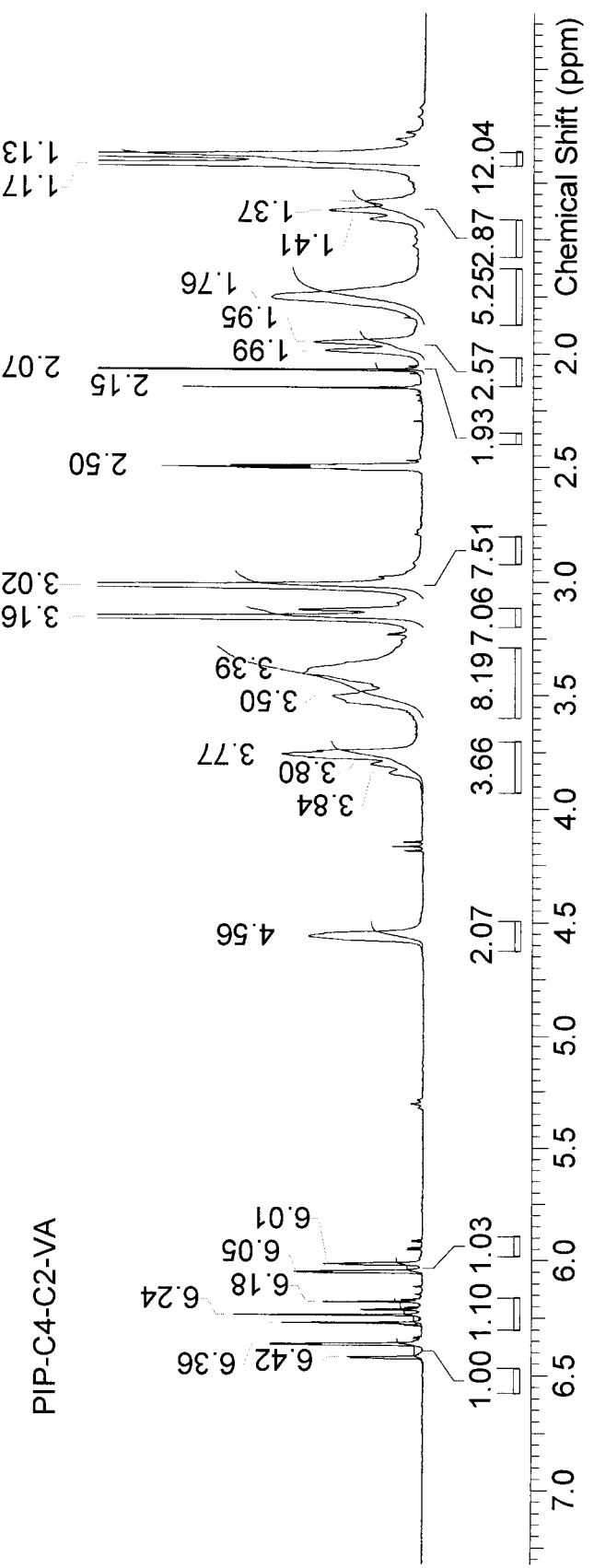
FIG. 28 is an example of NMR spectroscopy data of the reaction-product compound of FIG. 1G.

To make the PIP-C4-C2-vinyl-acetate compound, about 1.0 eq of DMATMP and about 1.0 eq of 1, 4-dibromobutane were dissolved in acetonitrile within a reaction vessel and refluxed for about 4 hours. The reaction mixture appeared as a white precipitate, which was dissolved again by adding methanol in a drop-wise fashion until a clear solution appeared. Next, a third reactant 1.0 eq of 2-(Dimethylamino) ethyl acrylate was added. The reaction mixture was stirred under reflux conditions for about 24 hours in acetonitrile/methanol. The solvent was evaporated and dried under vacuum. The purity of this PIP-C4-C2-vinyl-acetate compound was about 98% as verified by proton NMR in DMSO-d6. The yield of this reaction-product compound was about 90%. FIG. 28 shows an example of the NMR spectrum data obtained.

Figure 2:
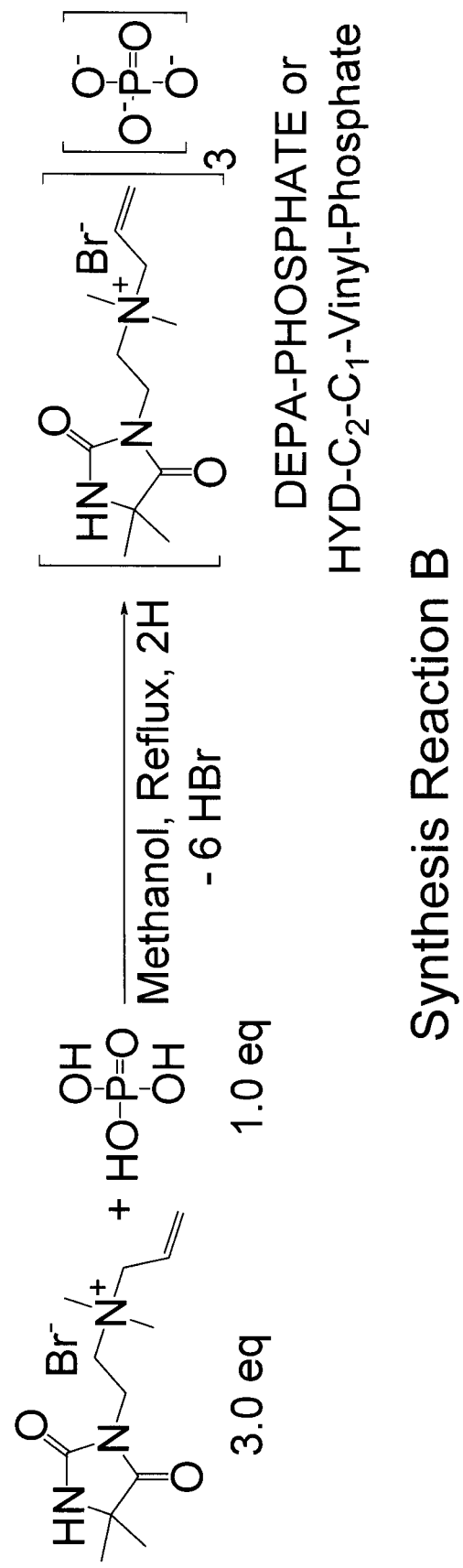
FIG. 2 is an example of another synthesis reaction series for producing a reaction-product compound with a vinyl functional-group according to an embodiment of the present disclosure that may be used as a component of a textile-coating formulation.

FIG. 2 shows another example of a reaction that produces a compound with an N-halamine precursor group, a cationic center and a vinyl CIG.

Figure 3:
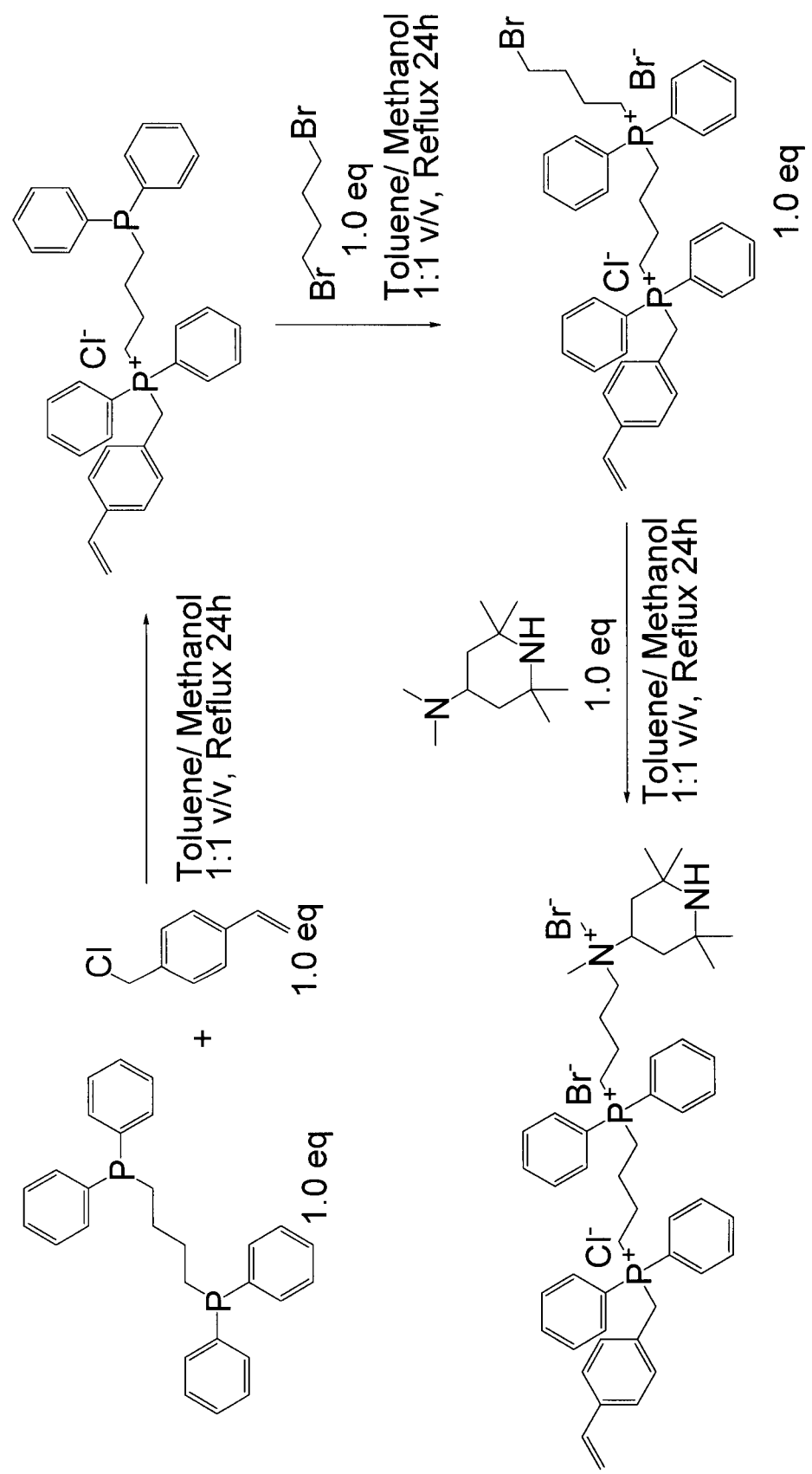
FIG. 3 is an example of another synthesis reaction series for producing a reaction-product compound with a vinyl functional-group according to an embodiment of the present disclosure that may be used as a component of a textile-coating formulation.

FIG. 3 shows another example of a series of reactions that use DMATMP as a reactant for synthesizing another reaction-product compound. This series of reactions is collectively referred to as Synthesis Reaction C and it comprises at least three steps, as shown in FIG. 3. The Synthesis Reaction C produces a reaction-product compound with an N-halamine precursor group, three cationic centers and a vinyl CIG. In this example, the reaction-product compound is referred to as PIP-C4-PPh2-C4-PPh2-C1-benzyl-vinyl. PIP refers to the cyclic N-halamine precursor group piperidine. The first C4 refers to the four-carbon chain between the QAS cationic center and a first phosphorous-based cationic center (P). PPh2 refers to the phosphorous-based cationic center (P) with two phenyl groups (Ph2). The second C4 refers to the four-carbon chain between the first phosphorous-based cationic center (P) and the second phosphorous-based cationic center (P), which also has two phenyl groups (Ph2). C1 refers to a single methyl group between the second cationic center and the benzyl vinyl group.

Figure 29:
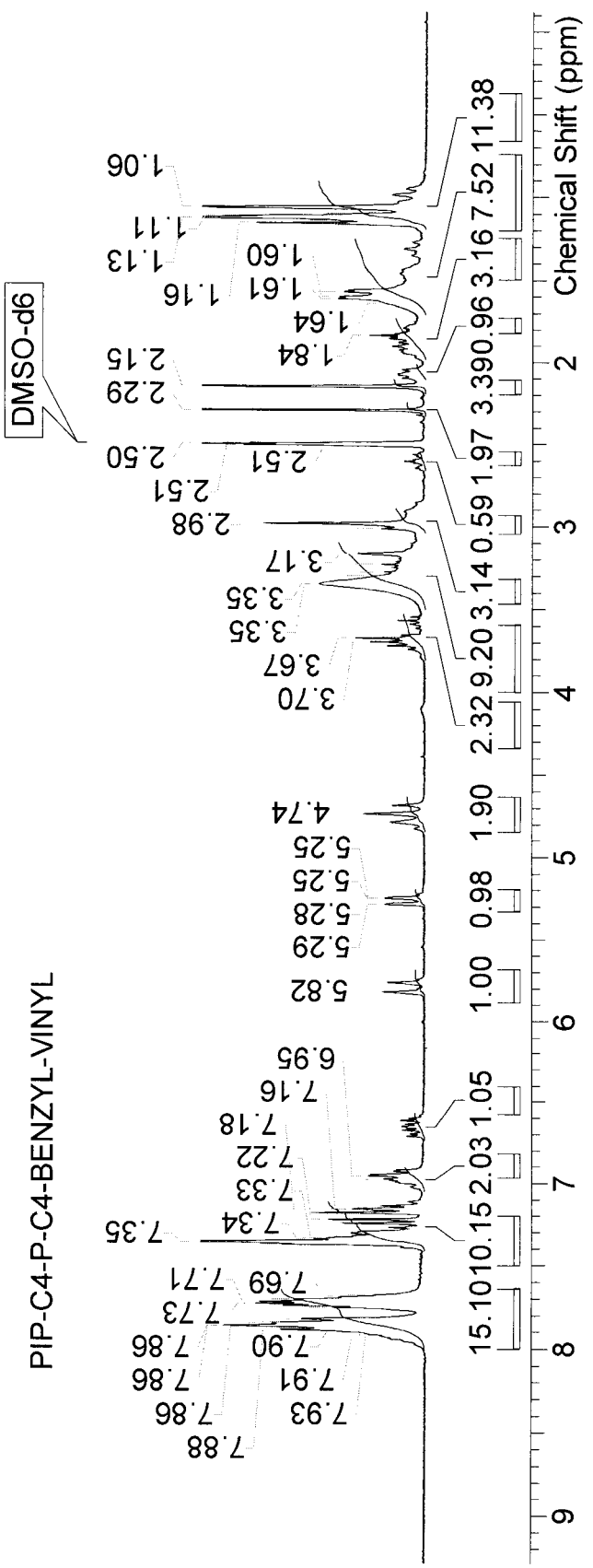
FIG. 29 is an example of NMR spectroscopy data of the reaction-product compound of FIG. 3.
Figure 54:
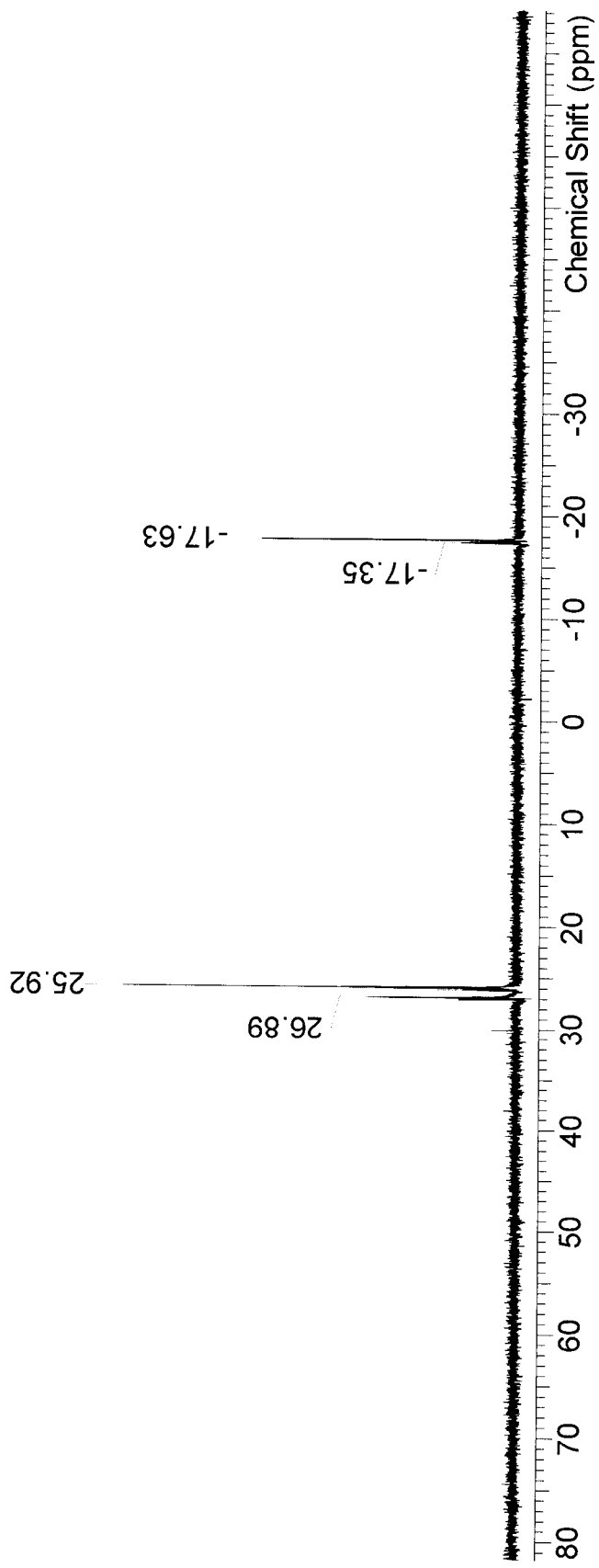
FIG. 54 is an example of a phosphorous-31 NMR spectrum from the reaction-compound shown in FIG. 3.

To make the PIP-C4-PPh2-C4-PPh2-C1-benzyl-vinyl compound the following were added to a reaction vessel: 1.0 eq of 1,4-Bis(diphenylphosphino)butane and 1.0 eq of 4-Vinylbenzyl chloride dissolved in Toluene/methanol (1:1) and refluxed for 24 hours. After that added the third reactant 1.0 eq of 1,4-dibromobutane. The reaction mixture was stirred under reflux condition for 24 hours in Toluene/methanol (1:1). After that added the fourth reactant 1.0 eq of N,N-dimethylamino-2,2,6,6-tetramethyl-piperidine. The reaction mixture was stirred again under reflux condition for 24 hours in Toluene/methanol (1:1). The solvent was evaporated and dried under vacuum. The purity of the compound was verified by NMR in DMSO-d6, which around 98% (FIG. 29). FIG. 54 shows the phosphorous-31 NMR spectrum from this reaction-compound. The yield of the product was 97%.

Figures 4, 4A:
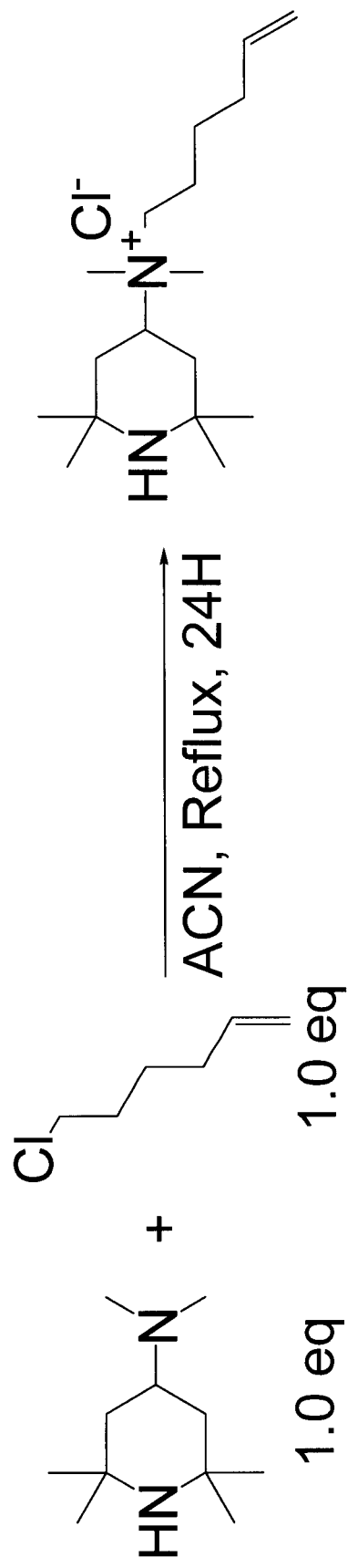

FIG. 4A shows another example of a series of reactions that use DMATMP as a reactant for synthesizing a reaction-product compound. This series of reactions is collectively referred to as Synthesis Reaction D and it comprises at least one step. The Synthesis Reaction D produces a reaction-product compound with an N-halamine precursor group, one cationic center, and a vinyl CIG. In this example, the reaction-product compound is referred to as PIP-C4-vinyl. PIP refers to the cyclic N-halamine precursor group piperidine. C4 refers to the four-carbon chain between the QAS cationic center and the vinyl group.

Figure 4B:
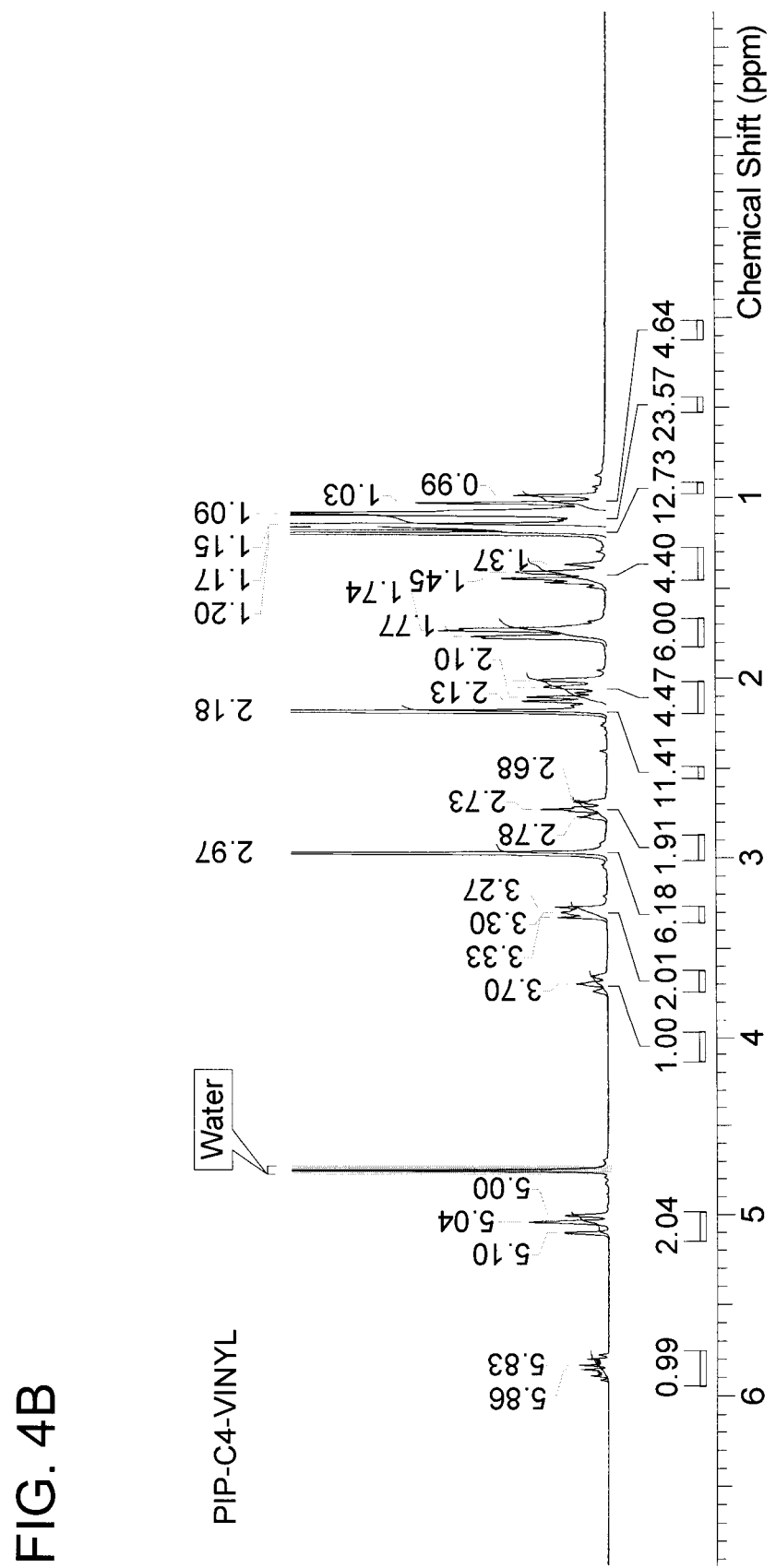

To make the PIP-C4-vinyl compound, about 1.0 eq of DMATMP and about 1.0 eq of 6-chloro-hex-1-ene were dissolved in acetonitrile within a reaction vessel and refluxed for about 24 hours. The solvent was evaporated and dried under vacuum. The purity of the PIP-C4-vinyl compound was about 98% as verified by NMR in $D_2O$ (FIG. 4B). The yield of this reaction-product compound was about 99%.

Figure 5:
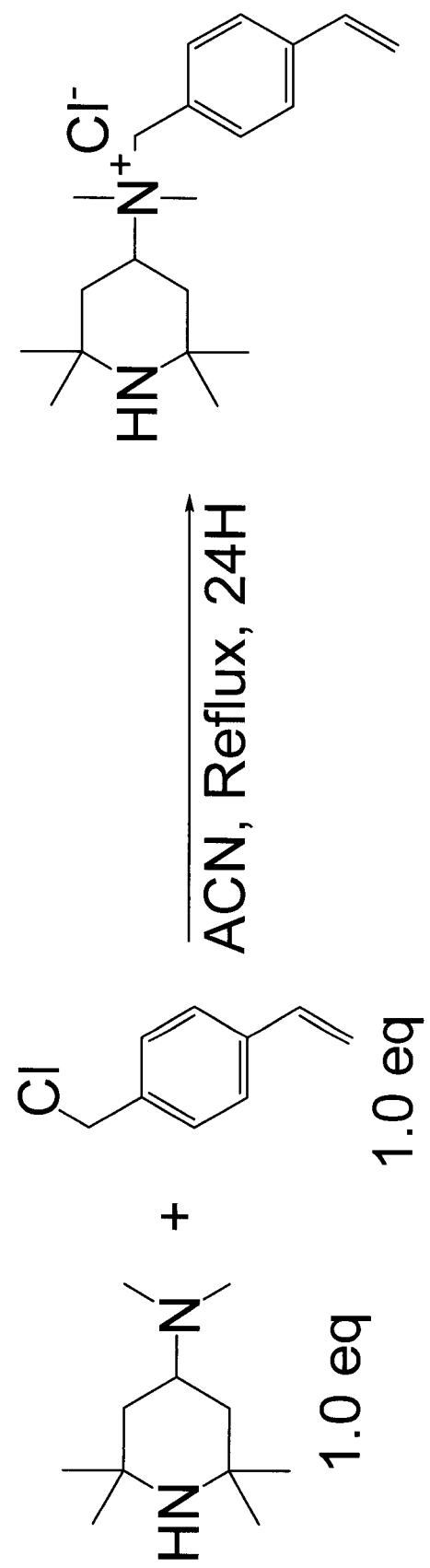

FIG. 5A shows another example of a series of reactions that use DMATMP as a reactant for synthesizing a reaction-product compound. This series of reactions is collectively referred to as Synthesis Reaction E and it comprises at least one step. The Synthesis Reaction E produces a reaction-product compound with an N-halamine precursor group, one cationic center, and a vinyl CIG. In this example, the reaction-product compound is referred to as PIP-C1-benzyl-vinyl. PIP refers to the cyclic N-halamine precursor group piperidine. C1 refers to the one carbon between the QAS cationic center and the benzyl-vinyl group.

Figure 5B:
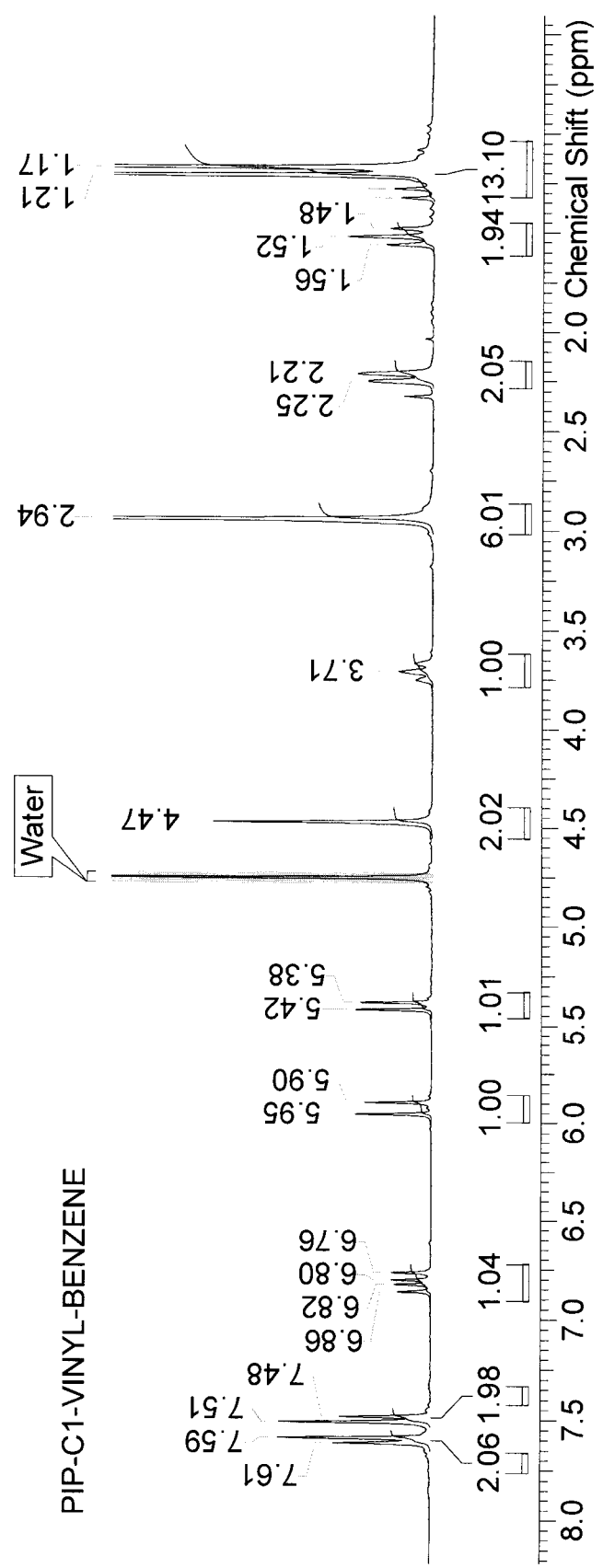

To make the PIP-C1-benzyl-vinyl compound, about 1.0 eq of DMATMP and about 1.0 eq of 4-vinylbenzyl chloride were dissolved in acetonitrile within a reaction vessel and refluxed for about 24 hours. The solvent was evaporated and dried under vacuum. The purity of the PIP-C1-benzyl-vinyl compound was about 98% as verified by NMR in $D_2O$ (FIG. 5B). The yield of this reaction-product compound was about 99%.

Figure 6:
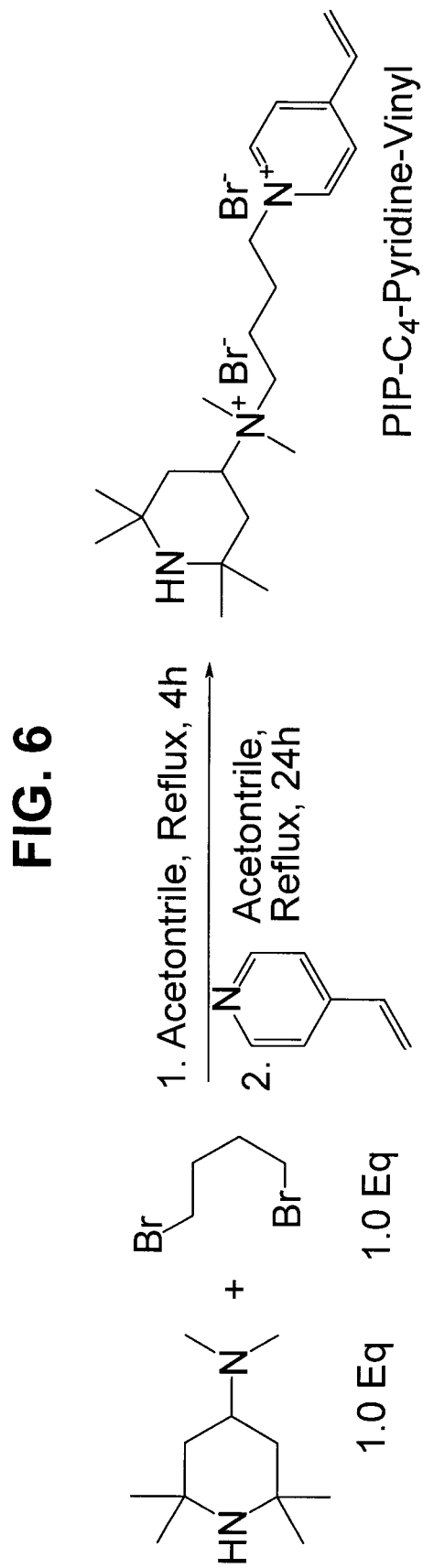
FIG. 6 is an example of another synthesis reaction series that, under the conditions described, was unsuccessful at producing a reaction-product compound that may be used as a component of a textile-coating formulation.

FIG. 6 shows another example of a series of reactions that use DMATMP as a reactant for synthesizing a reaction-product compound. This series of reactions is referred to as Synthesis Reaction F and no reaction-product compound was synthesized under the reaction conditions shown in FIG. 6.

Figure 7:
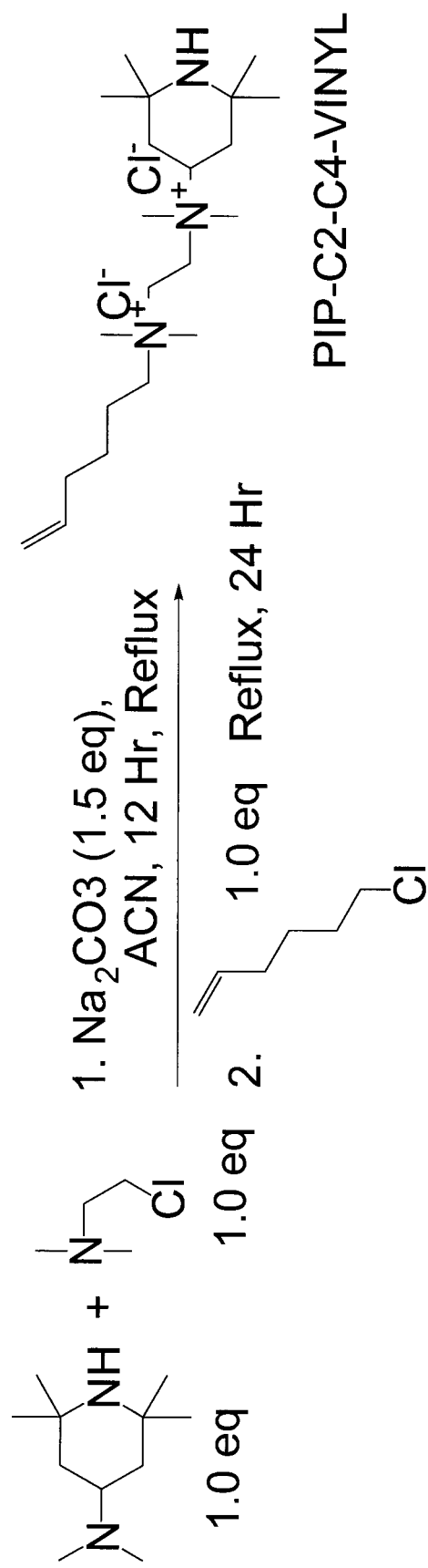
FIG. 7 is an example of another synthesis reaction series that, under the conditions described, was unsuccessful at producing a reaction-product compound that may be used as a component of a textile-coating formulation.

FIG. 7 shows another example of a series of reactions that use DMATMP as a reactant for synthesizing a reaction-product compound. This series of reactions is referred to as Synthesis Reaction G and no reaction-product compound was synthesized under the reaction conditions shown in FIG. 7.

Figure 8:
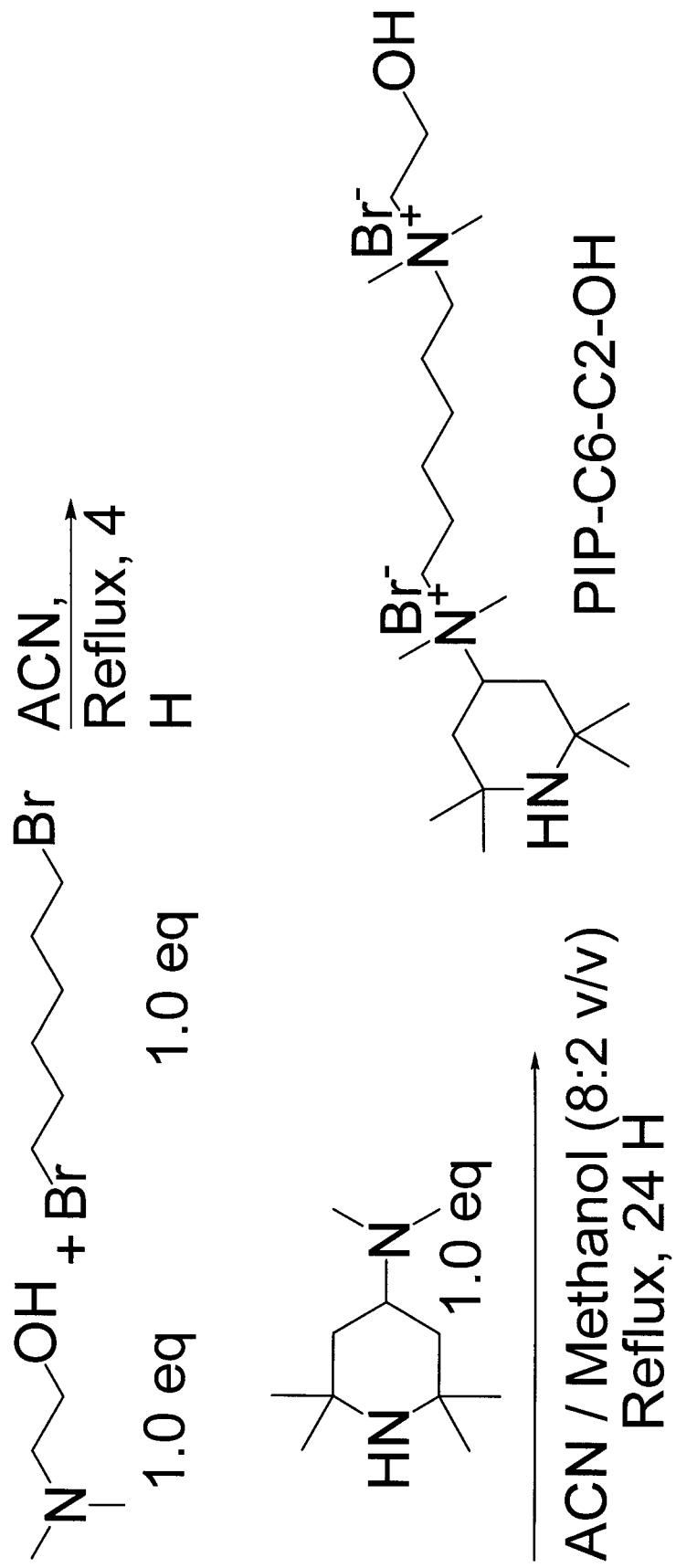
FIG. 8 is an example of another synthesis reaction series that, under the conditions described, was unsuccessful at producing a reaction-product compound that may be used as a component of a textile-coating formulation.

FIG. 8 shows another example of a series of reactions that use DMATMP as a reactant for synthesizing a reaction-product compound. This series of reactions is referred to as Synthesis Reaction H and no reaction-product compound was synthesized under the reaction conditions shown in FIG. 8.

Figures 9, 9A:
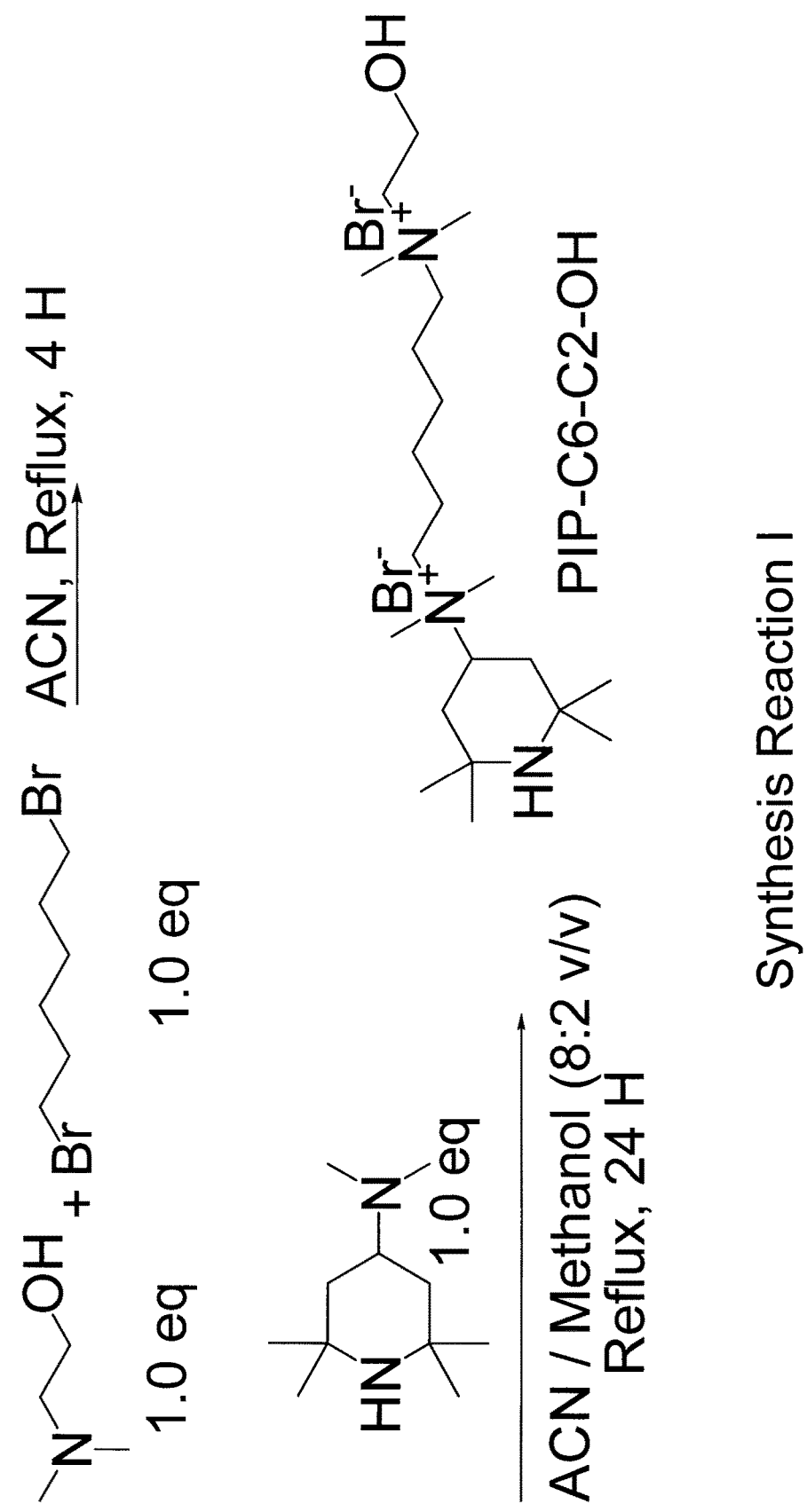

FIG. 9A shows another example of a series of reactions that use DMATMP as a reactant for synthesizing a reaction-product compound. This series of reactions is collectively referred to as Synthesis Reaction I and it comprises at least two steps. The Synthesis Reaction I produces a reaction-product compound with an N-halamine precursor group, two cationic centers, and a hydroxyl CIG. In this example, the reaction-product compound is referred to as PIP-C6-C2-OH. PIP refers to the cyclic N-halamine precursor group piperidine. C6 refers to the six-carbon chain between the first QAS cationic center and the second QAS cationic center. C2 refers to the two-carbon chain that connects the second QAS and the hydroxyl group (OH).

Figure 9B:
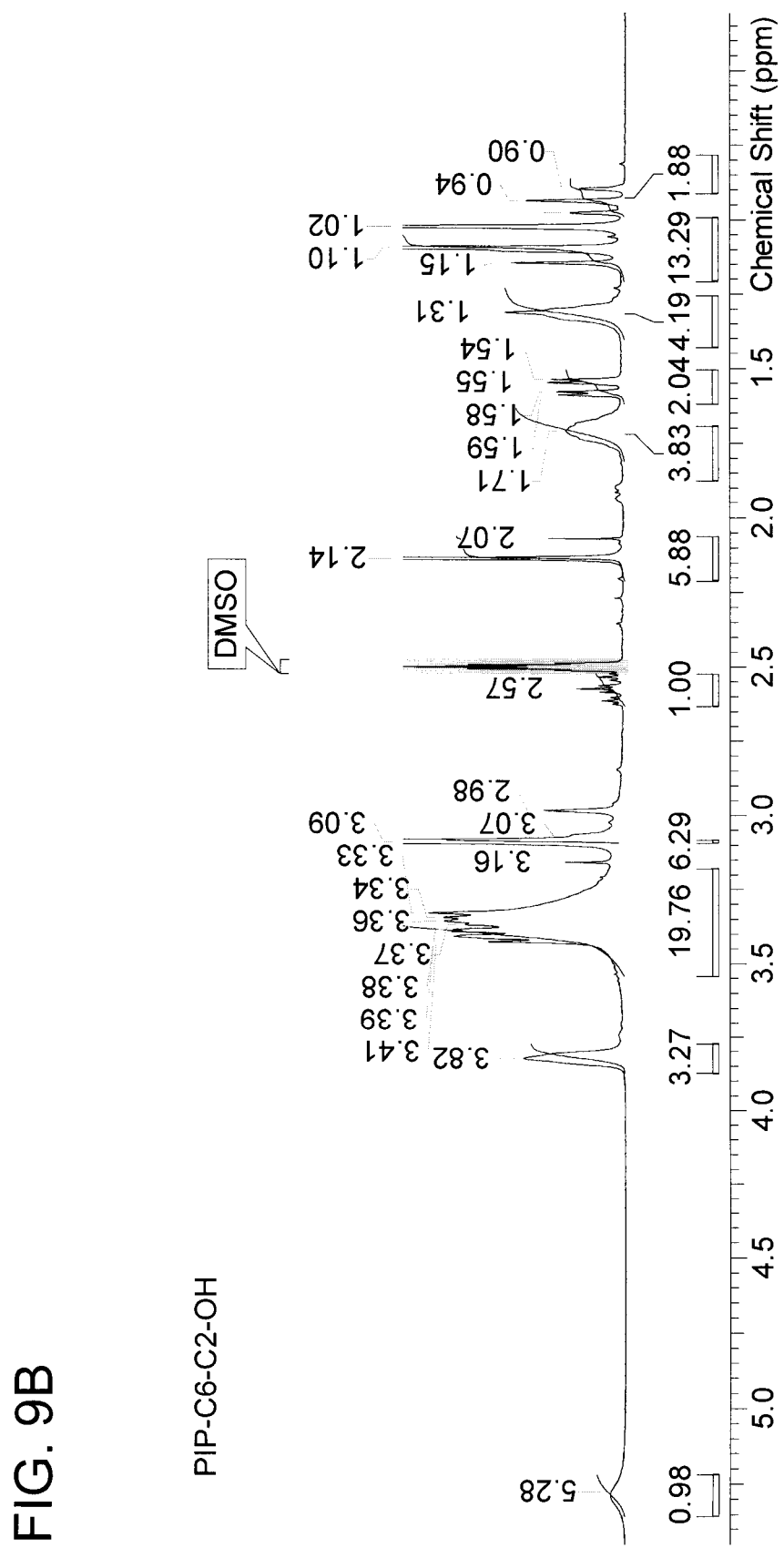

To make the PIP-C6-C2-OH compound, about 1.0 eq of DMATMP and about 1.0 eq of 1, 6-dibromohexane were dissolved in acetonitrile separately, mixed within a reaction vessel and refluxed for about 4 hours. The reaction mixture evaporated and appeared as a white precipitate, which was dissolved by adding acetonitrile/methanol mixture (8:2 v/v) until a clear solution appeared. After which, about 1.0 eq of DMATMP was added and the reaction mixture was stirred under reflux condition for about 24 hours in acetonitrile/methanol. The solvent was evaporated and dried under vacuum. The purity of the PIP-C6-C2-OH compound was about 98% as verified by NMR in DMSO-d6 (FIG. 9B). The yield of the reaction-product compound was about 95%.

Figure 10A:
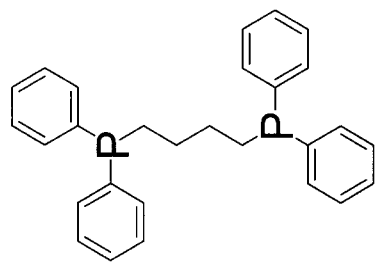
FIG. 10A shows the reactants and the reaction-product compound and FIG. 10B shows an example of NMR spectroscopy data of the reaction-product compound of FIG. 10A.

FIG. 10A shows another example of a series of reactions that use DMATMP as a reactant for synthesizing a reaction-product compound. This series of reactions is collectively referred to as Synthesis Reaction J and it comprises at least two steps. The Synthesis Reaction J produces a reaction-product compound with an N-halamine precursor group, three cationic centers, and a hydroxyl group. In this example, the reaction-product compound is referred to as PIP-C4-PPh2-C4-PPh2-C3-OH. PIP refers to the cyclic N-halamine precursor group piperidine. C4 refers to the four-carbon chain between the first QAS cationic center and the second cationic center, which is a phosphate-based cationic center (P) with two phenyl groups attached thereto (Ph2). The second C4 refers to the four-carbon chain that connects the second cationic center with the third cationic center which is also a phosphate-based cationic center (P) with two phenyl groups attached thereto (Ph2). C3 refers to the three-carbon chain between the third cationic center, and the hydroxyl group (OH).

To make the PIP-C4-PPh2-C4-PPh2-C3-OH compound, about 1.0 eq of 1, 4-bis (diphenylphosphino) butane, and about 1.0 eq of 3-bromopropanol were dissolved in toluene within a first reaction vessel and refluxed for about 24 hours. The reaction mixture evaporated and appeared as a white precipitate, which was dissolved by adding methanol in a drop-wise fashion until a clear solution appeared. About 1.0 eq of DMATMP and about 1.0 eq of 1, 4-dibromobutane were dissolved in acetonitrile within a second reaction vessel. This reaction mixture was stirred under reflux condition for 4 hours in acetonitrile and evaporated the solvent to get a white precipitate.

Figure 10B:
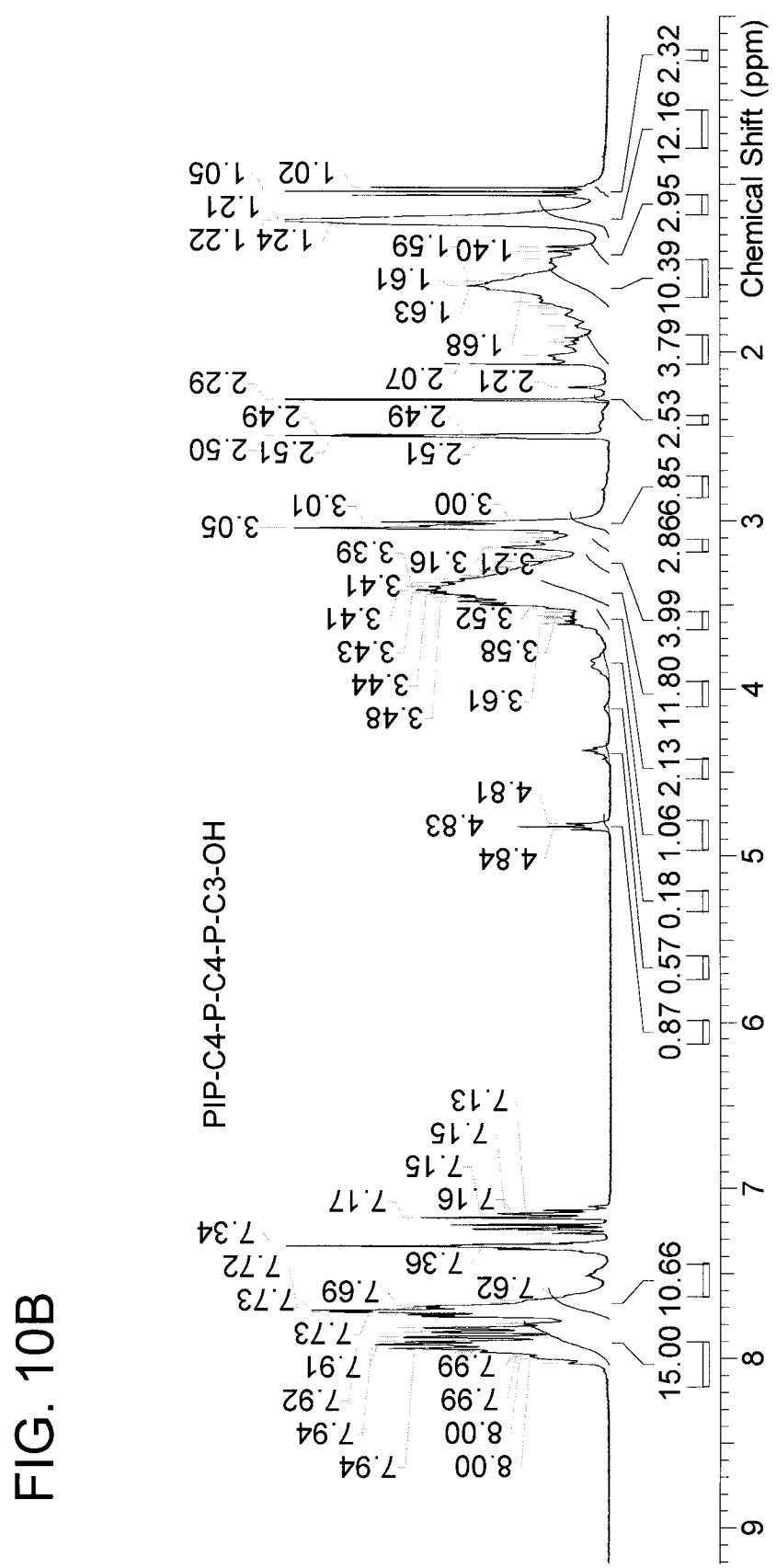

The contents of the two reaction vessel mixtures were combined and dissolved in a toluene/methanol mixture (8:2 v/v). The reaction mixture was stirred again under reflux conditions for about 24 hours in toluene/methanol. The solvent was evaporated and dried under vacuum to get a white precipitate. The purity of the PIP-C4-PPh2-C4-PPh2-C3-OH compound was assessed by NMR in DMSO-D6 (FIG. 10B). The yield of this reaction-product compound was about 95%.

Epoxy Coatings

DMATMP can also be used as a reactant to synthesize compounds that are suitable for use in an epoxy-based coating system. DMATMP may be used as a reactant to synthesize reaction-product compounds that have one or more N-halamine precursor groups, one or more cationic centers, and one or more primary amine CIGs. These reaction-product compounds are suitable as components of an epoxy-based coating system, which are suitable for coating hard surfaces.

Figures 11, 11A:
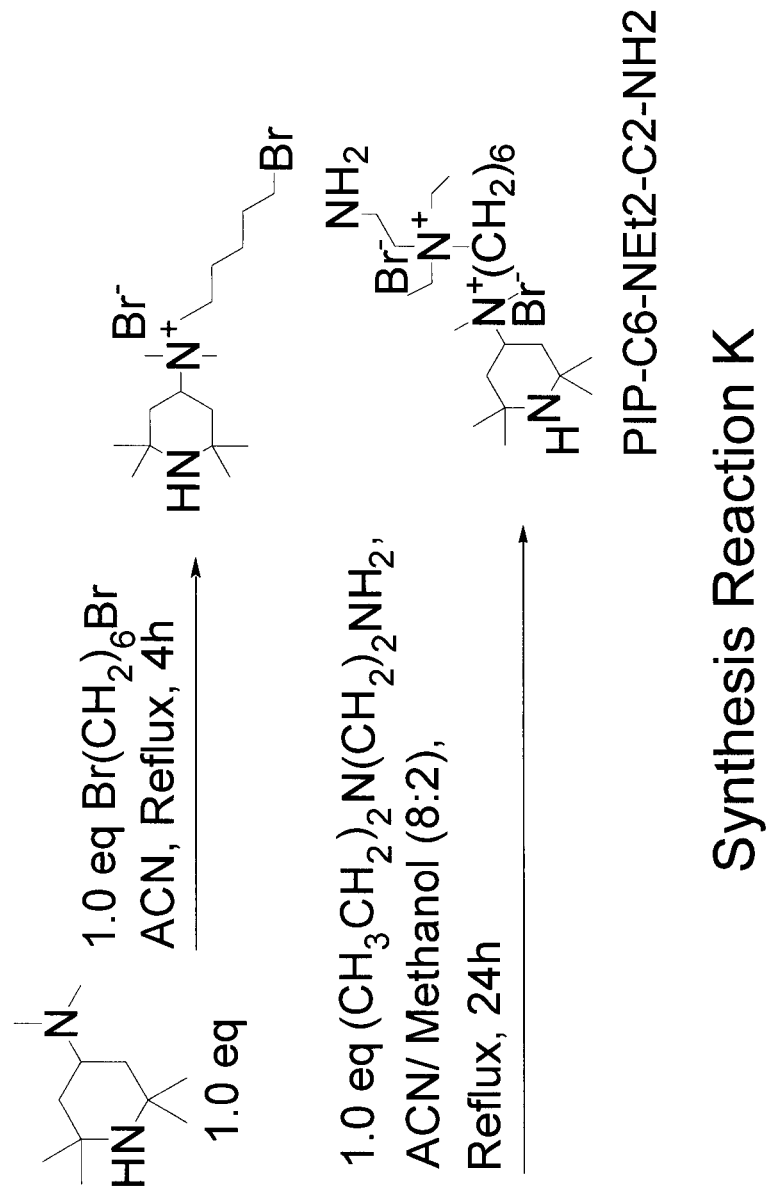

FIG. 11A shows another example of a series of reactions that use DMATMP as a reactant for synthesizing a reaction-product compound. This series of reactions is collectively referred to as Synthesis Reaction K and it comprises at least two steps. The Synthesis Reaction K produces a reaction-product compound with an N-halamine precursor group, two cationic centers, and a primary amine CIG. In this example, the reaction-product compound is referred to as PIP-C6-NEt2-C2-$NH_2$. PIP refers to the cyclic N-halamine precursor group piperidine. C6 refers to the six-carbon chain between the first cationic center, and the second cationic center, both of which are a QAS. NEt2 refers to the two ethyl groups that are attached to the second cationic center. C2 refers to the two-carbon chain that connects the second cationic center with the primary amine group ($NH_2$).

Figure 11B:
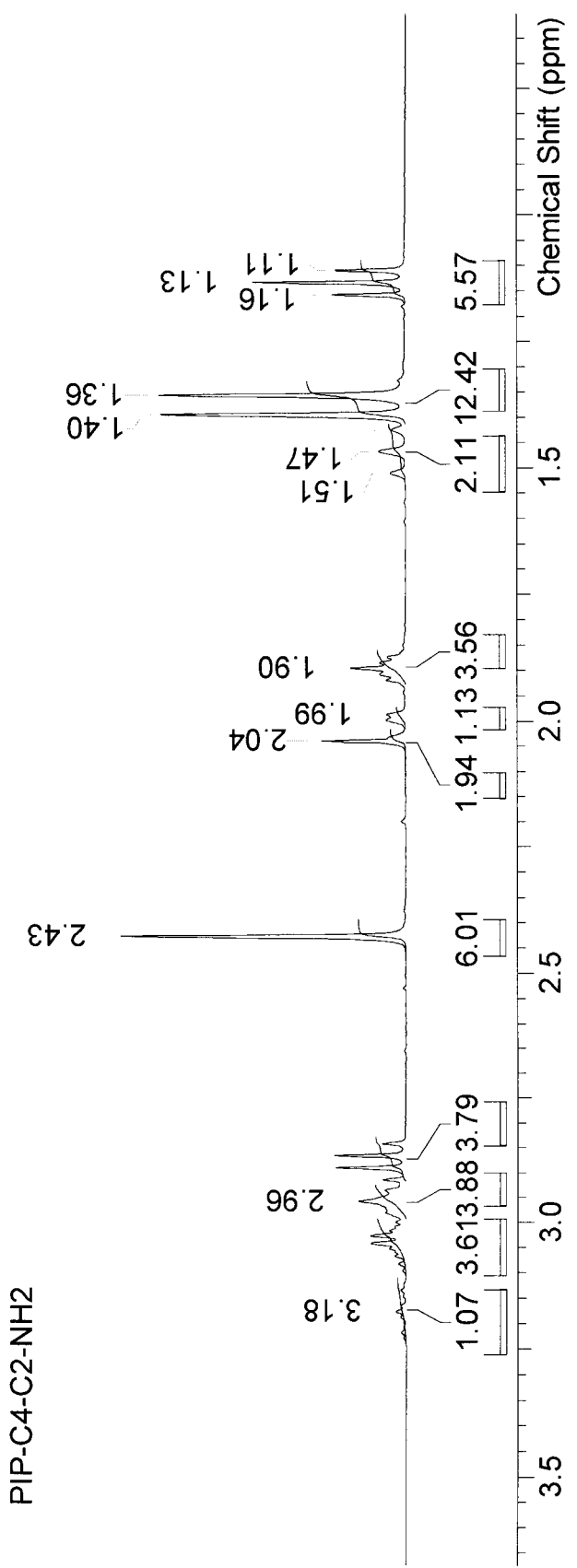

To make the PIP-C6-NEt2-C2-$NH_2$ compound, about 1.0 eq of DMATMP and about 1.0 eq of 1, 6-dibromohexane were dissolved in acetonitrile within a reaction vessel and refluxed for about 4 hours. The reaction mixture appeared as a white precipitate, which was dissolved again by adding methanol in a drop-wise fashion until a clear solution appeared. Following which, about 1.0 eq of 2-(N, N-Diethyl) ethylene amine was added. The reaction mixture was stirred under reflux conditions for about 24 hours in acetonitrile/methanol. The solvent was evaporated and dried under vacuum. The purity of the PIP-C6-NEt2-C2-$NH_2$ compound was about 98% as verified by NMR in $D_2O$ (FIG. 11B). The yield of this reaction-product compound was 94%.

Figure 12:
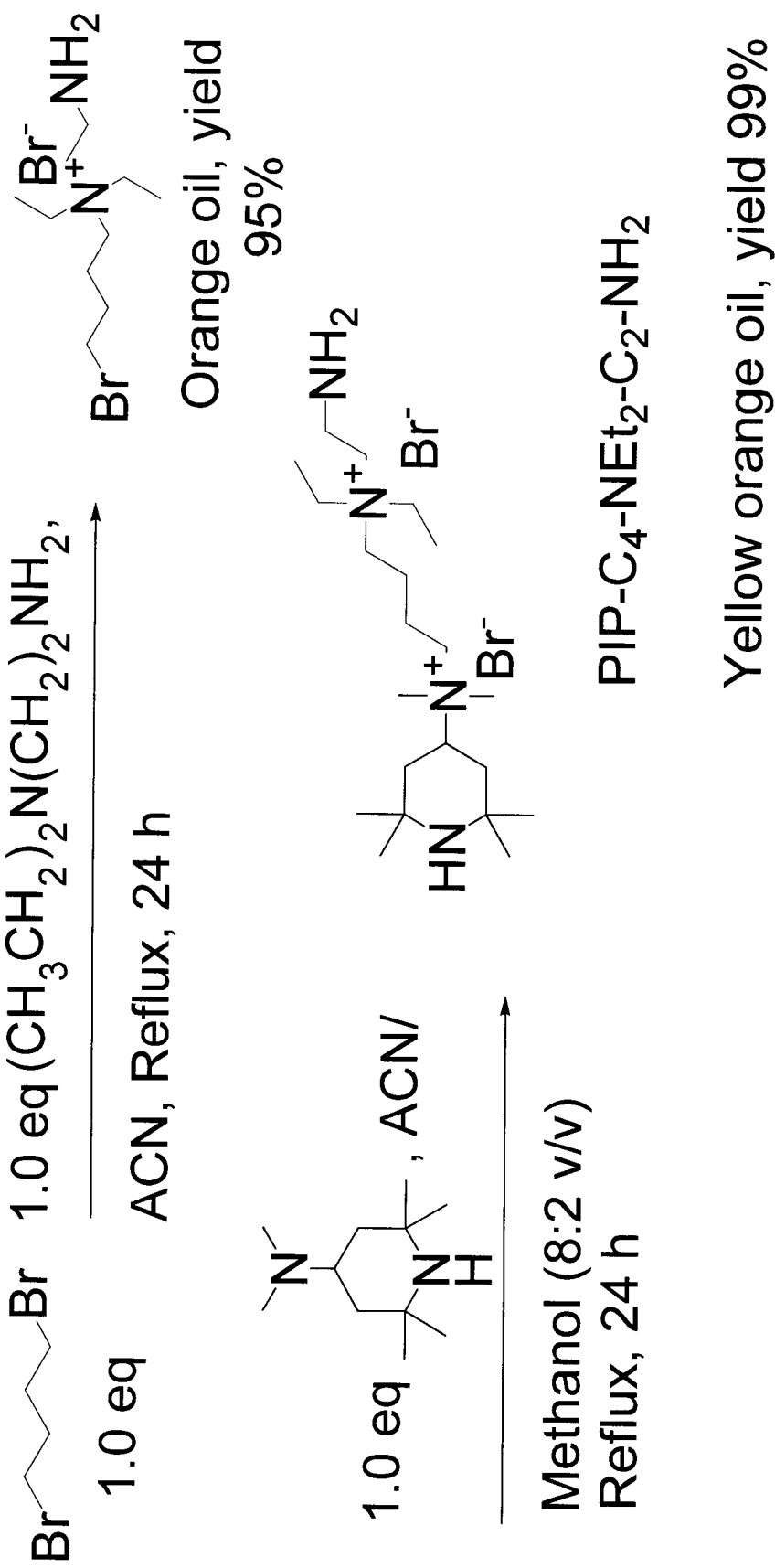
FIG. 12 is an example of another synthesis reaction series for producing a reaction-product compound with a primary amine functional-group according to an embodiment of the present disclosure that may be used as a component of an epoxy coating system.

FIG. 12 shows another example of a series of reactions that use DMATMP as a reactant for synthesizing a reaction-product compound. This series of reactions is collectively referred to as Synthesis Reaction L and it comprises at least two steps. The Synthesis Reaction L produces a reaction-product compound with an N-halamine precursor group, two cationic centers, and a primary amine group. In this example, the reaction-product compound is referred to as PIP-C4-NEt2-C2-$NH_2$. PIP refers to the cyclic N-halamine precursor group piperidine. C4 refers to the four-carbon chain between the first cationic center, and the second cationic center, both of which are a QAS. NEt2 refers to the two ethyl groups that are attached to the second cationic center. C2 refers to the two-carbon chain that connects the second cationic center with the primary amine group ($NH_2$).

To make the PIP-C4-C2-$NH_2$ compound, about 1.0 eq of 2-(N, N-Diethyl) ethylenediamine and about 1.0 eq of 1, 4 dibromohexane were dissolved in acetonitrile within a reaction vessel separately, mixed and refluxed for about 24 hours. The reaction mixture evaporated and appeared as an orange oil, which was dissolved again by adding acetonitrile/methanol mixture (8:2 v/v) until a clear solution appeared. Following which, about 1.0 eq of DMATMP was added. The reaction mixture was stirred under reflux condition for about 24 hours in acetonitrile/methanol. The solvent was evaporated and dried under vacuum. The purity of the PIP-C4-C2-$NH_2$ compound was about 98% as verified by NMR in $D_2O$. The yield of this reaction-product compound was about 99%.

Figures 13, 13A:
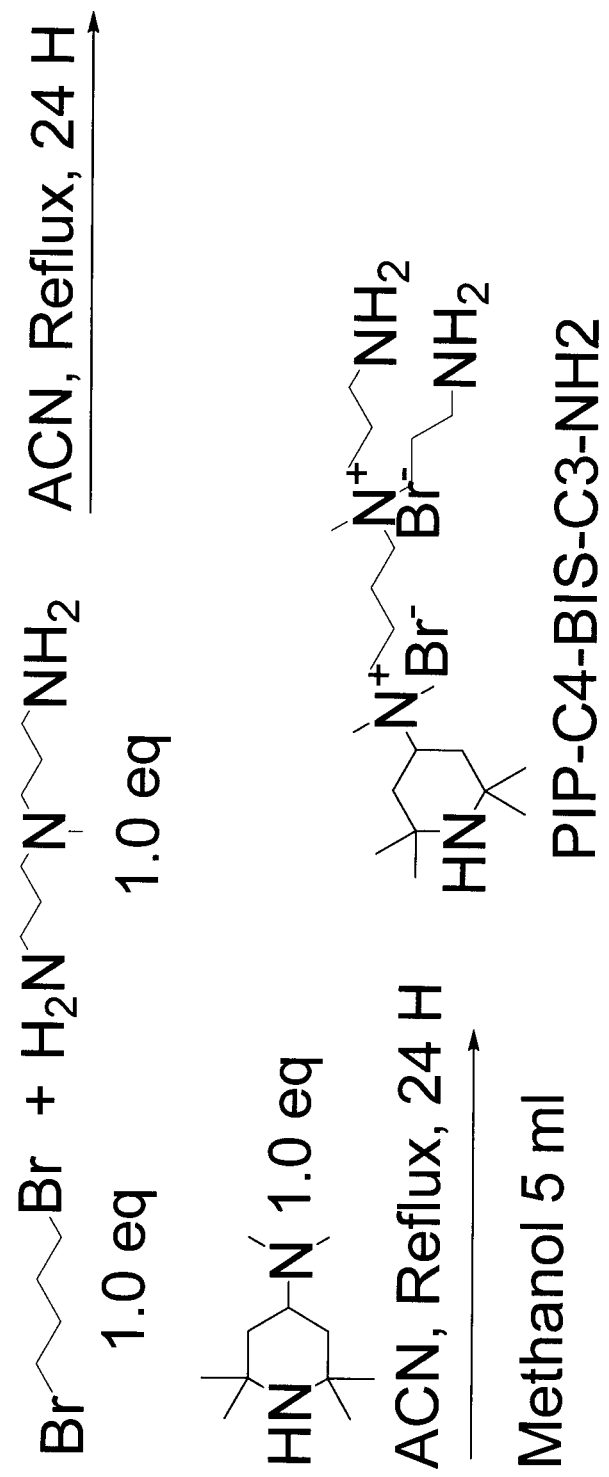

FIG. 13A shows another example of a series of reactions that use DMATMP as a reactant for synthesizing a reaction-product compound. This series of reactions is collectively referred to as Synthesis Reaction M and it comprises at least two steps. The Synthesis Reaction M produces a reaction-product compound with an N-halamine precursor group, two cationic centers, and two primary amine CIGs. In this example, the reaction-product compound is referred to as PIP-C4-BIS-C3-NH$_2$. PIP refers to the cyclic N-halamine precursor group piperidine. C4 refers to the four-carbon chain between the first cationic center, and the second cationic center, both of which are a QAS. BIS-C3 refers to the two three-carbon chains that each connect the second cationic center with a primary amine group (NH$_2$).

Figure 13B:
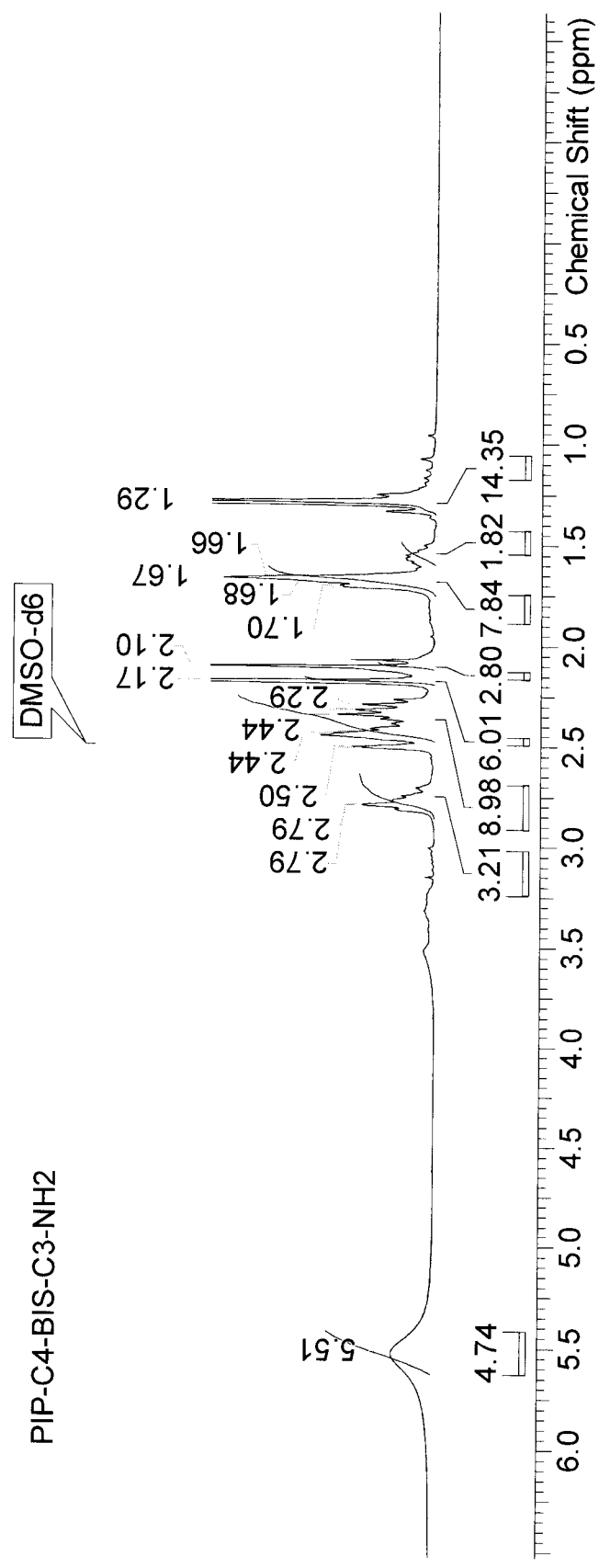

To make the PIP-C4-BIS-C3-NH$_2$ compound, about 1.0 eq of 3, 3-diamino-N-methyldipropylamine and about 1.0 eq of 1, 4-dibromobutane were dissolved within a reaction vessel in acetonitrile separately, mixed and refluxed for about 24 hours. The reaction mixture evaporated and appeared as an orange oil, which was dissolved again by adding acetonitrile/methanol mixture (8:2 v/v) until a clear solution appeared. After that about 1.0 eq of DMATMP was added. The reaction mixture was stirred under reflux condition for about 24 hours in acetonitrile/methanol. The solvent was evaporated and dried under vacuum to form as an off-white solid. The purity of the PIP-C4-BIS-C3-NH$_2$ compound was about 98% as verified by NMR in D$_2$O (FIG. 13B). The yield of this reaction-product compound was about 99%.

Figures 14, 14A:
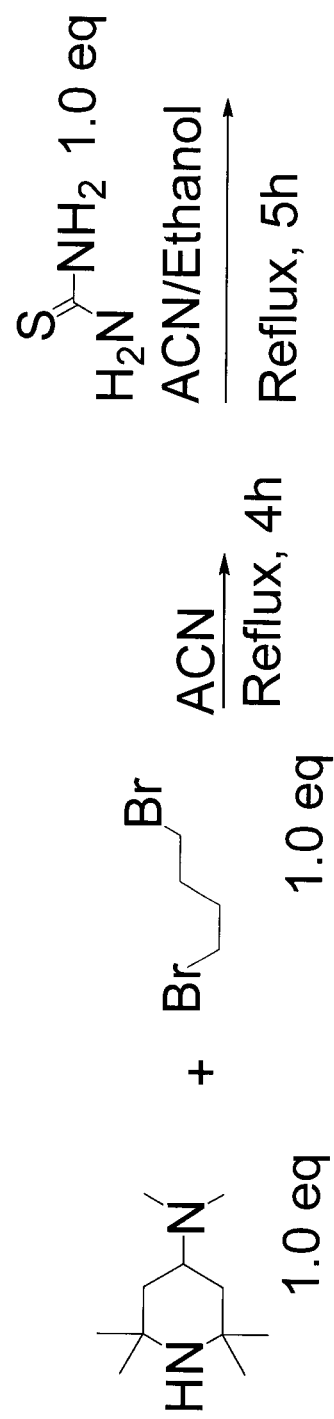

FIG. 14A shows another example of a series of reactions that use DMATMP as a reactant for synthesizing a reaction-product compound. This series of reactions is collectively referred to as Synthesis Reaction N and it comprises at least two steps. The Synthesis Reaction N produces a reaction-product compound with an N-halamine precursor group, two cationic centers, and two primary amine CIGs. In this example, the reaction-product compound is referred to as PIP-C4-thiourea. PIP refers to the cyclic N-halamine precursor group piperidine. C4 refers to the four-carbon chain between the first cationic center, and the second cationic center. The first cationic center is a QAS and the second cationic center is a sulfur-based cationic center (S). The sulfur-based cationic center is part of the thiourea group that has two primary amine groups.

Figure 14B:
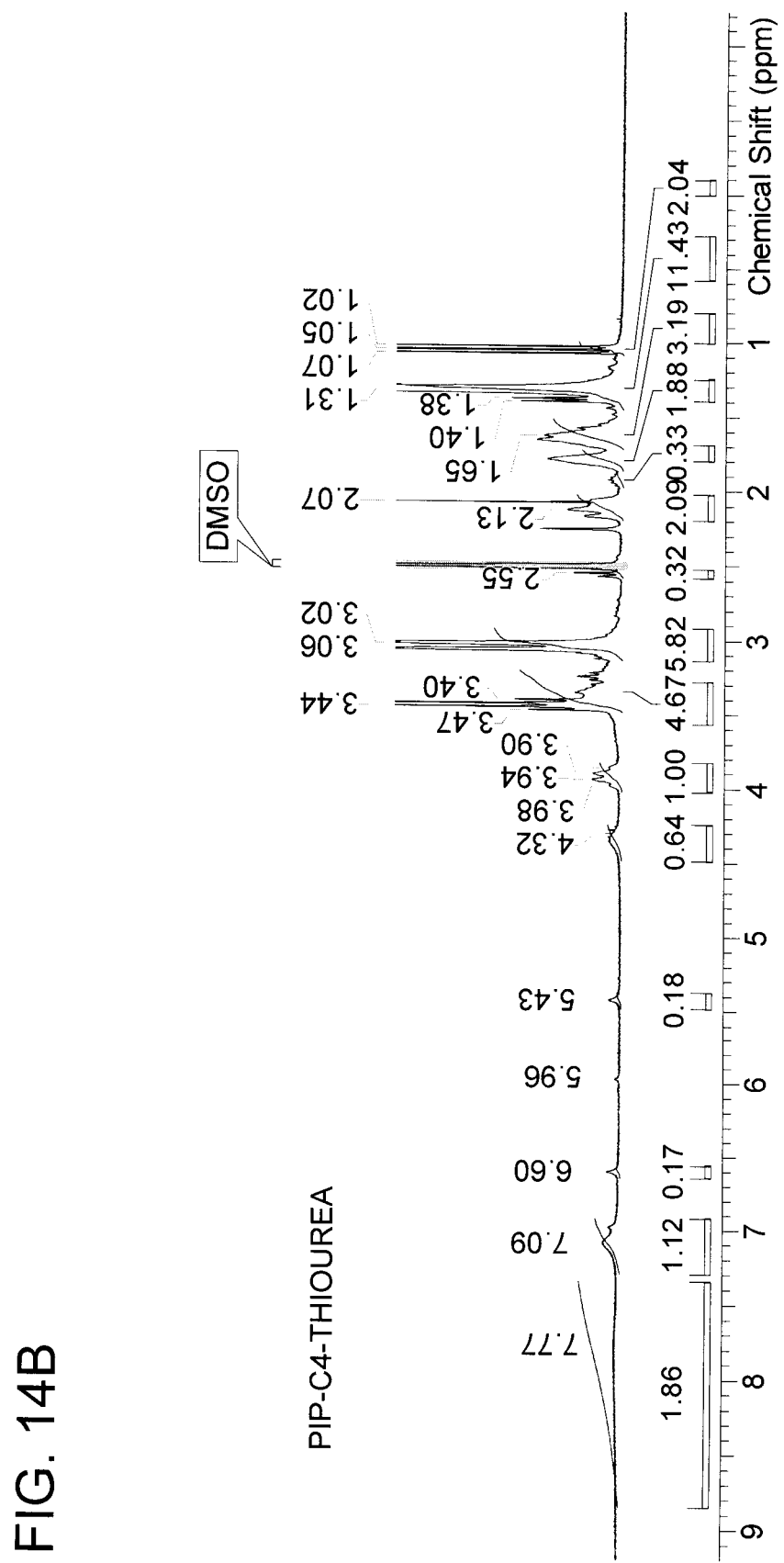

To make the PIP-C4-thiourea compound, about 1.0 eq of DMATMP and about 1.0 eq of 1, 4-dibromobutane were dissolved in acetonitrile within a reaction vessel and refluxed for about 4 hours. The reaction mixture appeared as a white precipitate, which was dissolved again by adding methanol in a drop-wise fashion until a clear solution appeared. Following which, about 1.0 eq of 2-(Dimethylamino) ethyl acrylate was added. The reaction mixture was stirred under reflux condition for about 24 hours in acetonitrile/methanol. The solvent was evaporated and dried under vacuum. The purity of PIP-C4-thiourea compound was about 98% as verified by NMR in DMSO-d6 (FIG. 14B). The yield of this reaction-product compound was about 90%.

Figures 15, 15A:
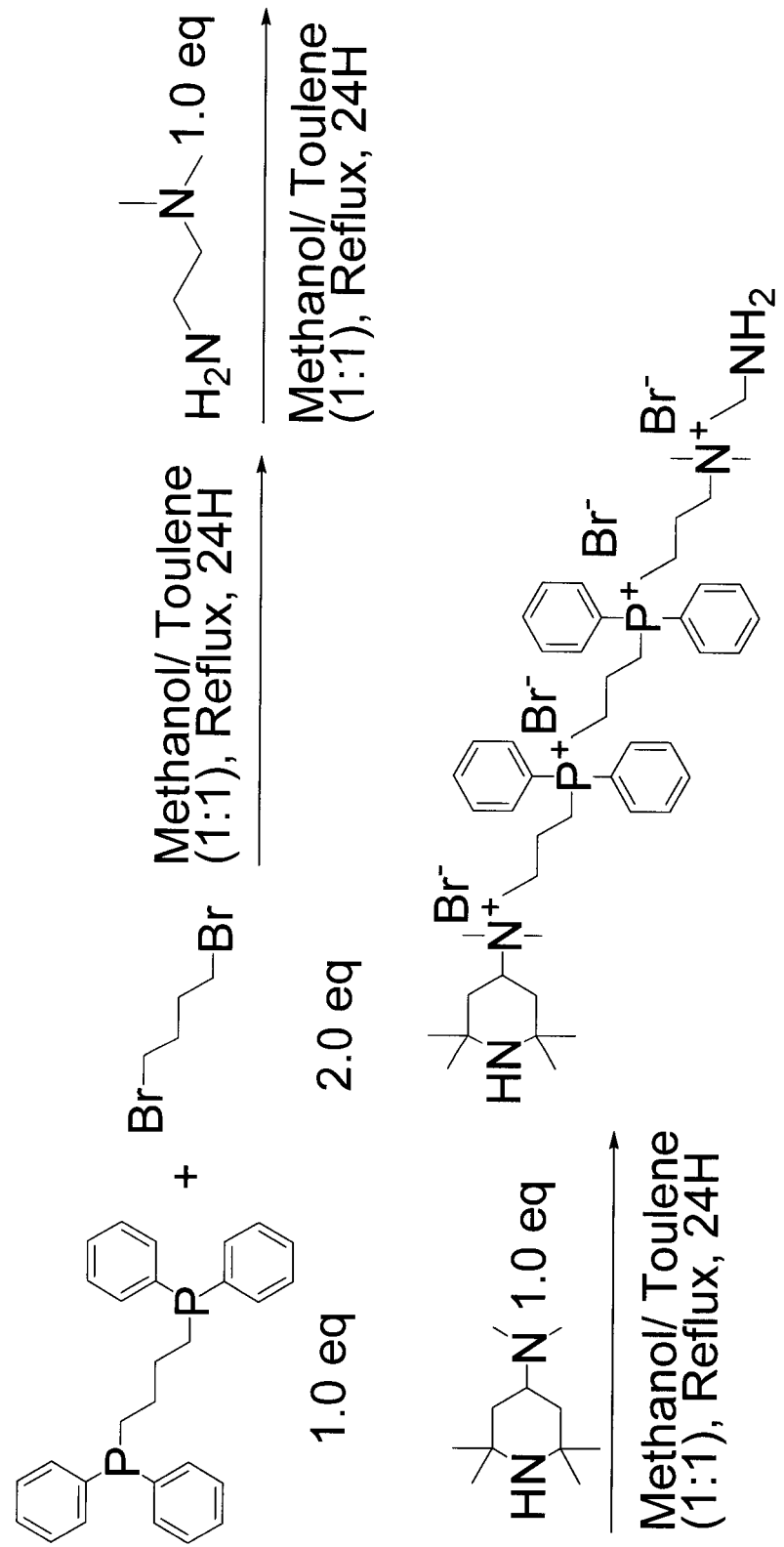

FIG. 15A shows another example of a series of reactions that use DMATMP as a reactant for synthesizing a reaction-product compound. This series of reactions is referred to as Synthesis Reaction 0 and it produces a reaction-product compound with an N-halamine precursor group, three cationic centers, and analogues of a thiol-urea functional group. In this example, the reaction-product compound is referred to as PIP-C4-PPh2-C4-PPh2-C2-NH$_2$. PIP refers to the cyclic N-halamine precursor group piperidine. The first C4 refers to the four-carbon chain between the first cationic center, and the second cationic center. The first cationic center is a QAS and the second cationic center is a phosphate-based cationic center (P) with two phenyl groups attached thereto (Ph2). The second C4 refers to the four-carbon chain between the second cationic center, and the third cationic center, which is also a phosphate-based cationic center (P) with two phenyl groups attached thereto (Ph2). C2 refers to a two-carbon chain between the third cationic center, and the primary amine group.

Figure 15B:
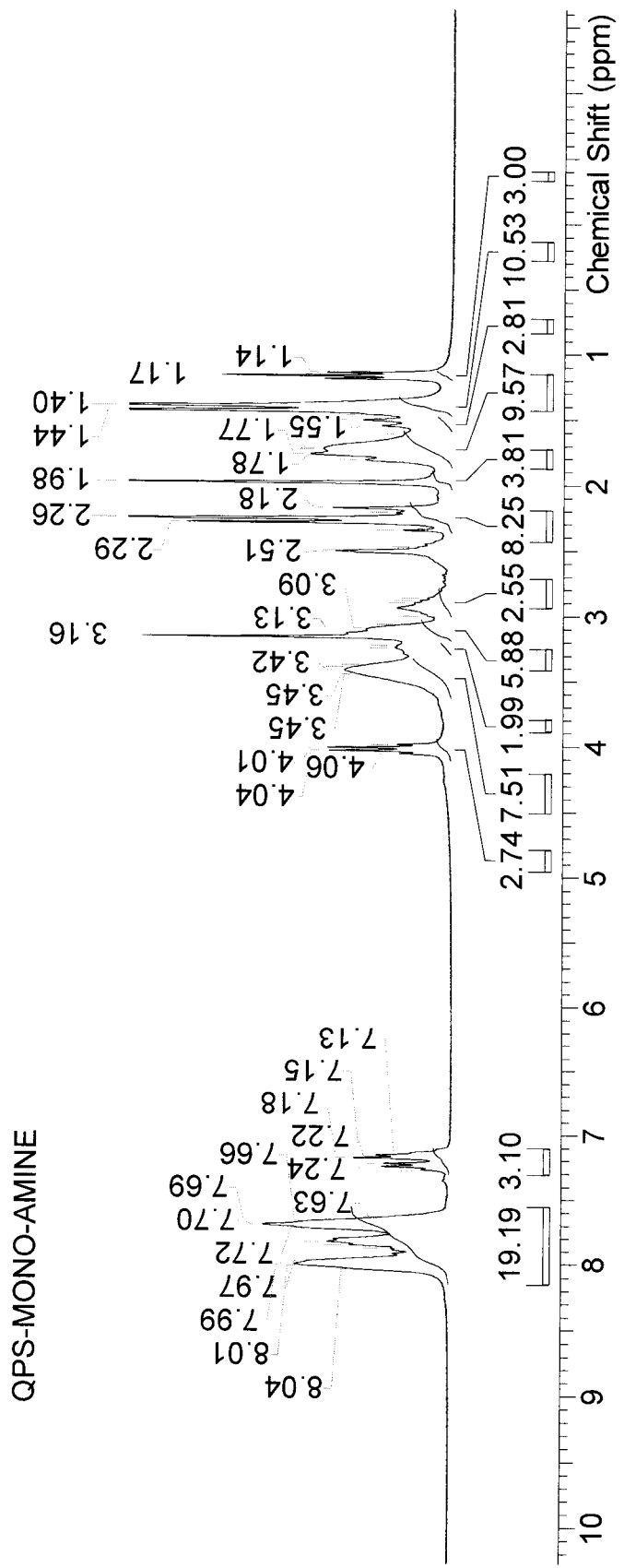

To make the PIP-C4-PPh2-C4-PPh2-C2-NH$_2$ compound the following were added to a reaction vessel: 1.0 eq of 1,4-Bis(diphenylphosphino)butane and 2.0 eq of 1,4-dibromobutane dissolved in toluene/methanol (1:1 v/v) and refluxed for 24 hours. In the same reaction vessel, added the third reactant 1.0 eq of N,N-Dimethylethylenediamine and refluxed for another 24 hours. Again to the same reaction vessel added the fourth reactant 1.0 eq. of N,N-dimethylamino-2,2,6,6-tetramethyl-piperidine and refluxed it for another 24 hours. The solvent was evaporated and dried under vacuum to resolve a white precipitate. The NMR (proton and phosphorus-31) (FIG. 15B) confirmed a purity of 97%. The yield of the product was 99%.

Figure 16:
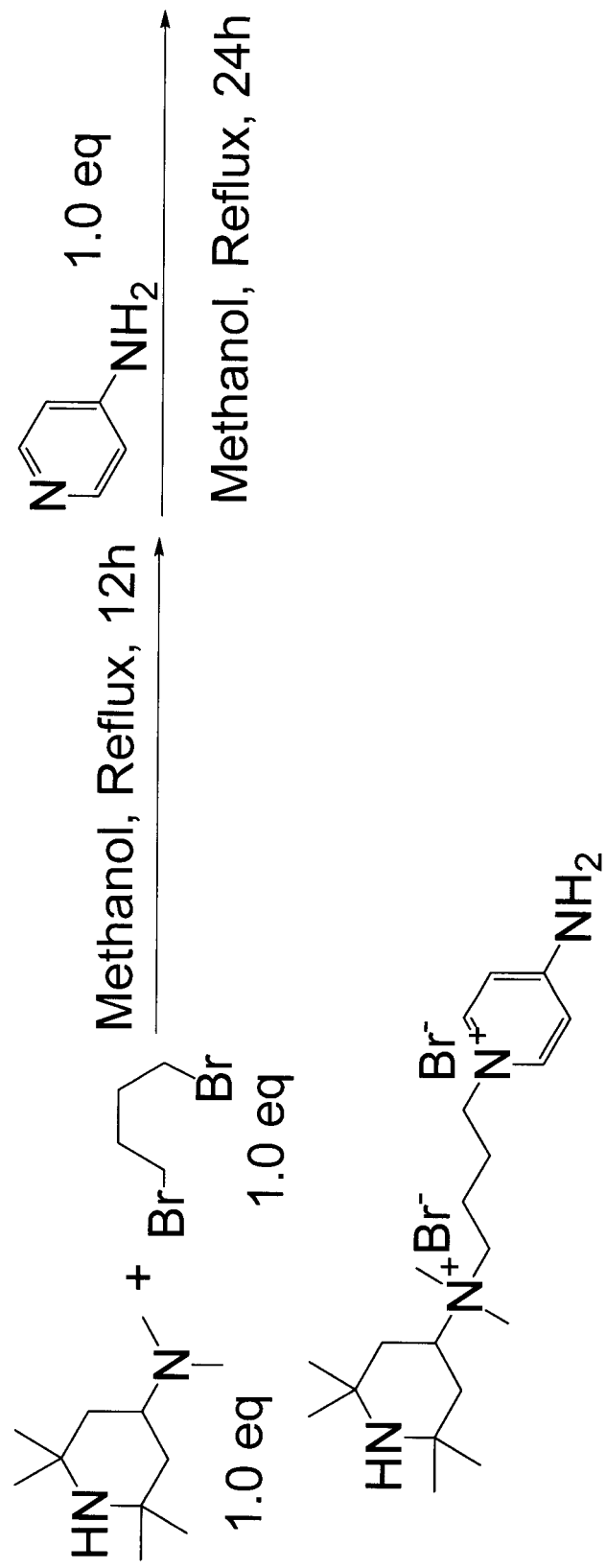

FIG. 16A shows another example of a series of reactions that use DMATMP as a reactant for synthesizing a reaction-product compound. This series of reactions is collectively referred to as Synthesis Reaction P and it comprises at least two steps. The Synthesis Reaction P produces a reaction-product compound with an N-halamine precursor group, two cationic centers, and one primary amine group. In this example, the reaction-product compound is referred to as PIP-C4-PYR-NH$_2$ (shown as PIP-C4-PYRIDINE-AMINE in FIG. 16). PIP refers to the cyclic N-halamine precursor group piperidine. C4 refers to the four-carbon chain between the first cationic center, and the second cationic center. The first cationic center is a QAS and the second cationic center is a cyclic QAS called a pyridine that is connected to the primary amine group.

To make the PIP-C4-PYR-NH$_2$ compound, about 1.0 eq of 4-aminopyridine and about 1.0 eq of 1, 4-dibromohexane were dissolved in acetonitrile in a reaction vessel and refluxed for about 4 hours. The reaction mixture evaporated and appeared as a white precipitate, which was dissolved by adding acetonitrile/methanol mixture (8:2 v/v) until a clear solution appeared. Following which, about 1.0 eq of DMATMP was added. The reaction mixture was stirred under reflux condition for about 24 hours in acetonitrile/methanol. The solvent was evaporated and dried under vacuum. FIG. 16B shows an example of NMR spectrum data obtained.

Figure 17:
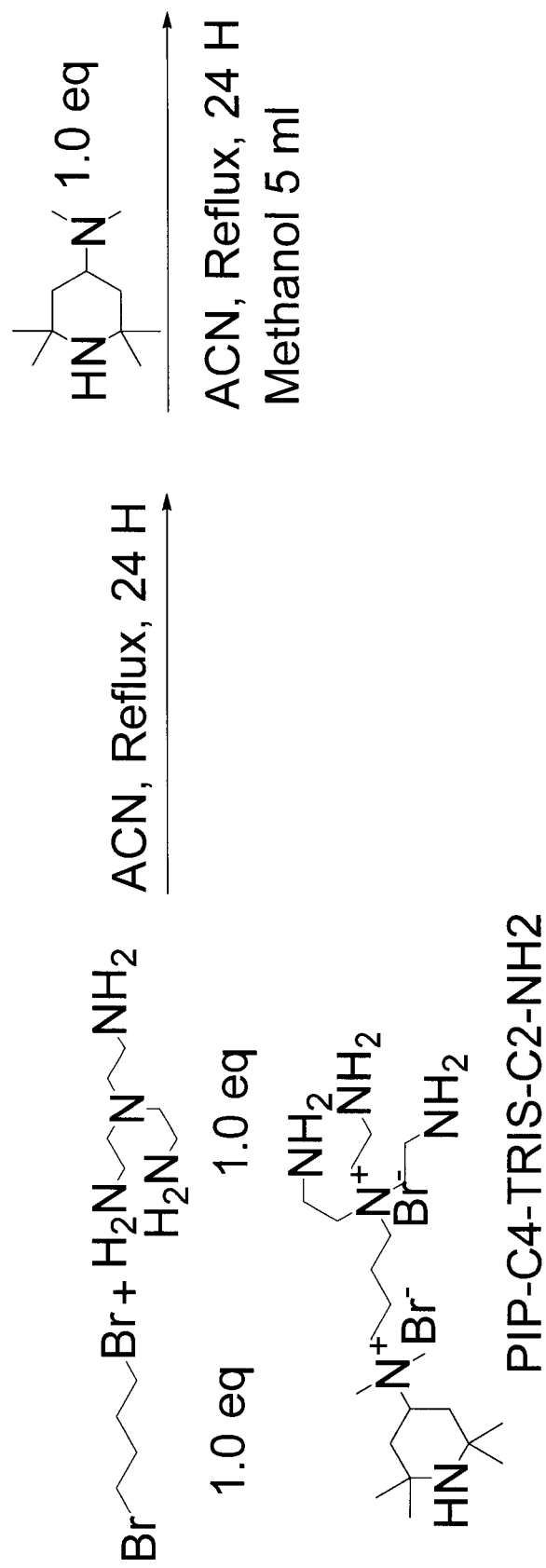
FIG. 17 is an example of a synthesis reaction series for producing a reaction-product compound with three primary amine functional-groups according to an embodiment of the present disclosure that may be used as a component of an epoxy coating system.

FIG. 17 shows another example of a series of reactions that use DMATMP as a reactant for synthesizing a reaction-product compound. This series of reactions is collectively referred to as Synthesis Reaction Q and it comprises at least two steps. The Synthesis Reaction Q produces a reaction-product compound with an N-halamine precursor group, two cationic centers, and three primary amine groups. In this example, the reaction-product compound is referred to as PIP-C4-TRIS-C2-NH$_2$. PIP refers to the cyclic N-halamine precursor group piperidine. C4 refers to the four-carbon chain between the first cationic center, and the second cationic center. The first and second cationic centers are each a QAS. C2 refers to the two-carbon chain that connects each of the three primary amine groups to the second cationic center.

To make the PIP-C4-TRIS-C2-NH$_2$ compound, about 1.0 eq of tris(2-aminoethyl)amine and about 1.0 eq of 1,6-dibromohexane were dissolved in acetonitrile within a reaction vessel, mixed and refluxed for about 4 hours. The reaction mixture evaporated and appeared as a white precipitate, which was dissolved again by adding an acetonitrile/methanol mixture (8:2 v/v) until a clear solution appeared. Following which, about 1.0 eq of DMATMP was added. The reaction mixture was stirred under reflux condition for about 24 hours in acetonitrile/methanol. The solvent was evaporated and dried under vacuum.

Liquid Formulation

DMATMP can also be used as a reactant to synthesize compounds that are suitable for use as a component in a liquid formulation with biocidal properties or with the potential for biocidal properties. DMATMP may be used as a reactant to synthesize reaction-product compounds that have one or more N-halamine precursor groups, one or more cationic centers, and carbon chains attached thereto.

Figures 18, 18A:
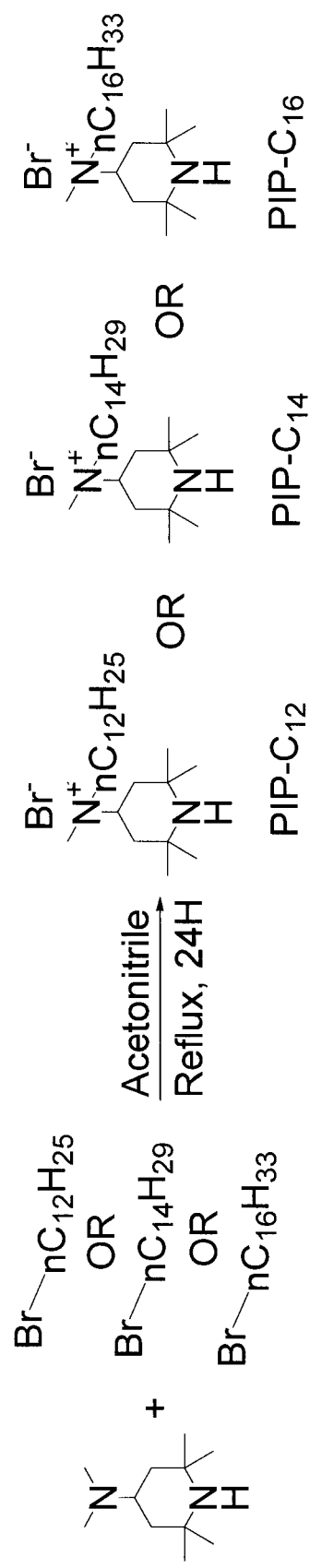

FIG. 18A shows another example of a series of reactions that use DMATMP as a reactant for synthesizing one of three reaction-product compounds. This series of reactions is collectively referred to as Synthesis Reaction R and it comprises at least one step. The Synthesis Reaction R may produce one of three reaction-product compounds each with an N-halamine precursor group, one QAS cationic center, and a carbon chain attached thereto. In this example, the reaction-product compounds may be three compounds which are referred to as PIP-C12, PIP-C14 and PIP-C16. PIP refers to the cyclic N-halamine precursor group piperidine. C12 refers to the twelve-carbon chain that is connected to the cationic center. C14 refers to the fourteen-carbon chain that is connected the cationic center. C16 refers to the sixteen-carbon chain that is connected to the cationic center.

Figure 30:
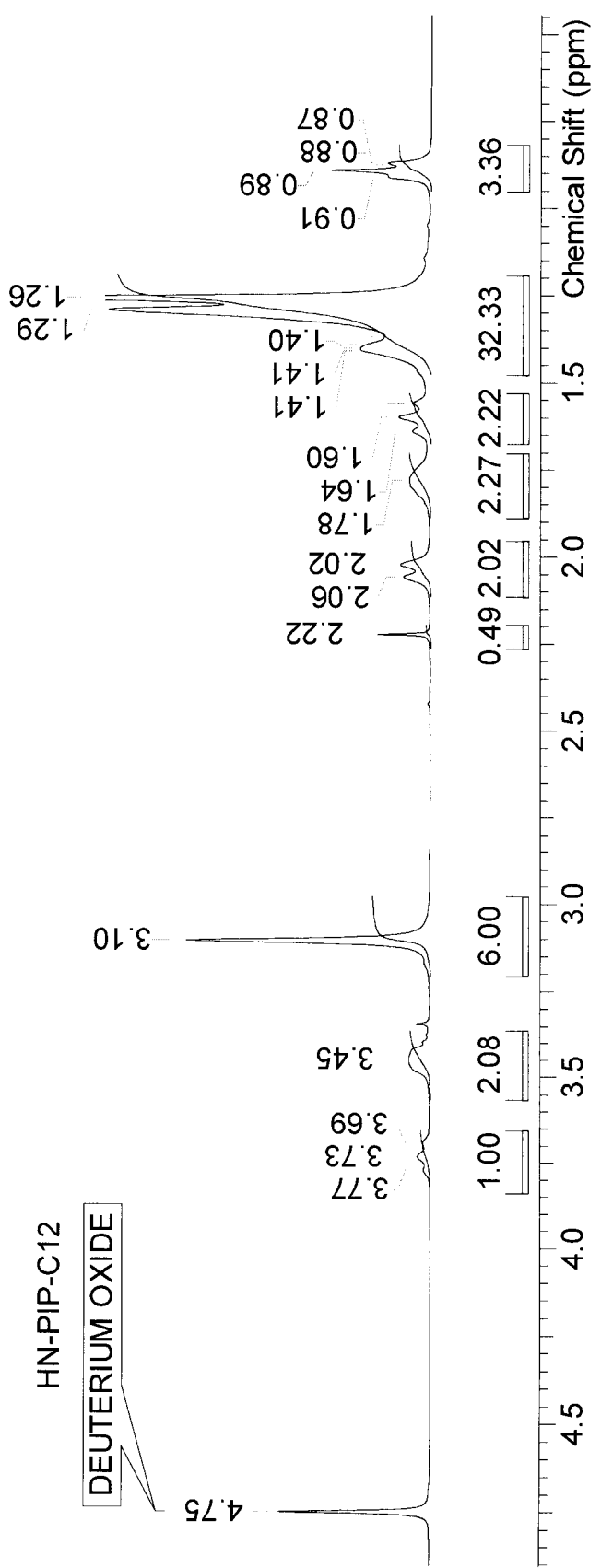
FIG. 30 is an example of NMR spectroscopy data of the PIP-C12 compound reaction-product compound of FIG. 18A.

To make the PIP-C12 compound, about 1.0 eq of DMATMP and about 1.0 eq 1-bromododecane were dissolved in acetonitrile within a reaction vessel and refluxed for about 4 hours. The solvent was evaporated under reduced pressure. The purity was about 99% as verified by NMR using $D_2O$ and the yield of this reaction-product compound was about 98% (FIG. 30).

Figure 31:
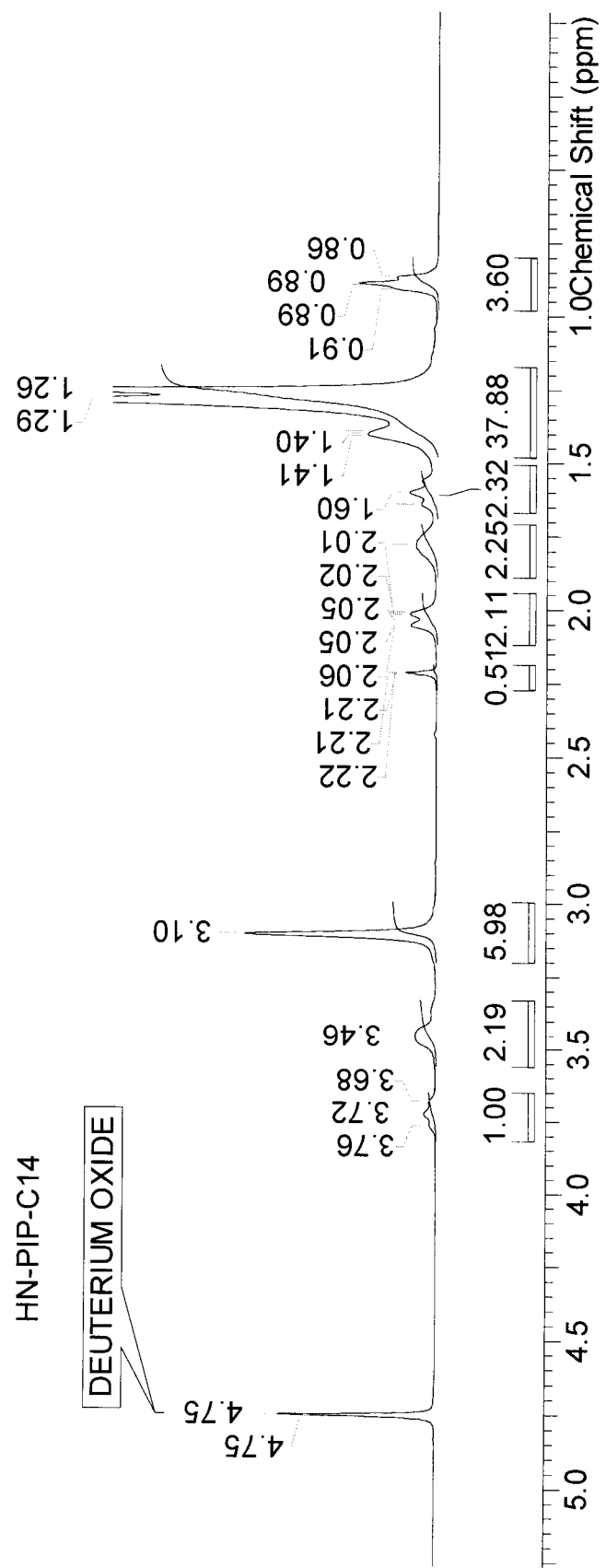
FIG. 31 is an example of NMR spectroscopy data of the PIP-C14 compound reaction-product compound of FIG. 18A.

To make the PIP-C14 compound, about 1.0 eq of DMATMP and about 1.0 eq of 1-bromotetradecane were dissolved in acetonitrile within a reaction vessel and refluxed for about 4 hours. The solvent was evaporated under reduced pressure. The purity was about 99% as verified by NMR using $D_2O$ and the yield of this reaction-product compound was about 98% (FIG. 31).

Figure 32:
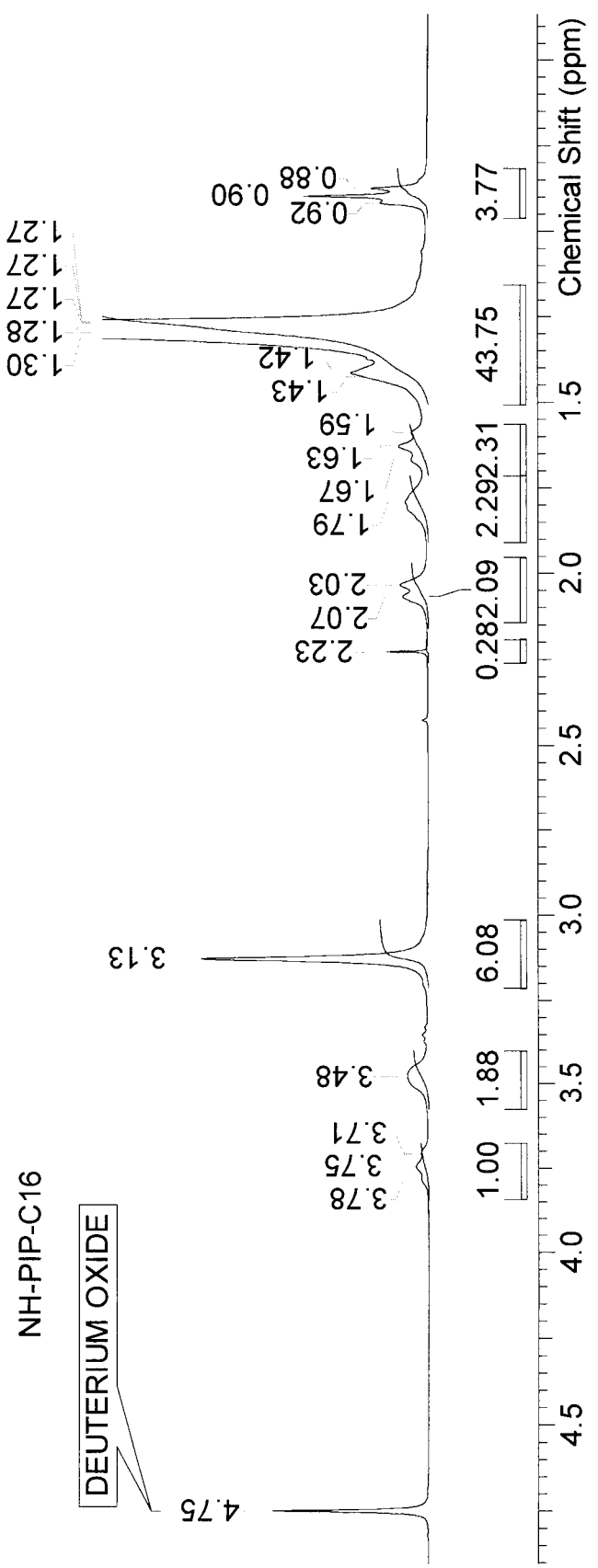
FIG. 32 is an example of NMR spectroscopy data of the PIP-C16 compound reaction-product compound of FIG. 18A.

To make the PIP-C16 compound, about 1.0 eq of DMATMP and about 1.0 eq of 1-bromohexadecane were dissolved in acetonitrile within a reaction vessel and refluxed for about 4 hours. The solvent was evaporated under reduced pressure. The purity was about 99% as verified by NMR using $D_2O$ and the yield of this reaction-product compound was about 98% (FIG. 32).

Figure 18B:
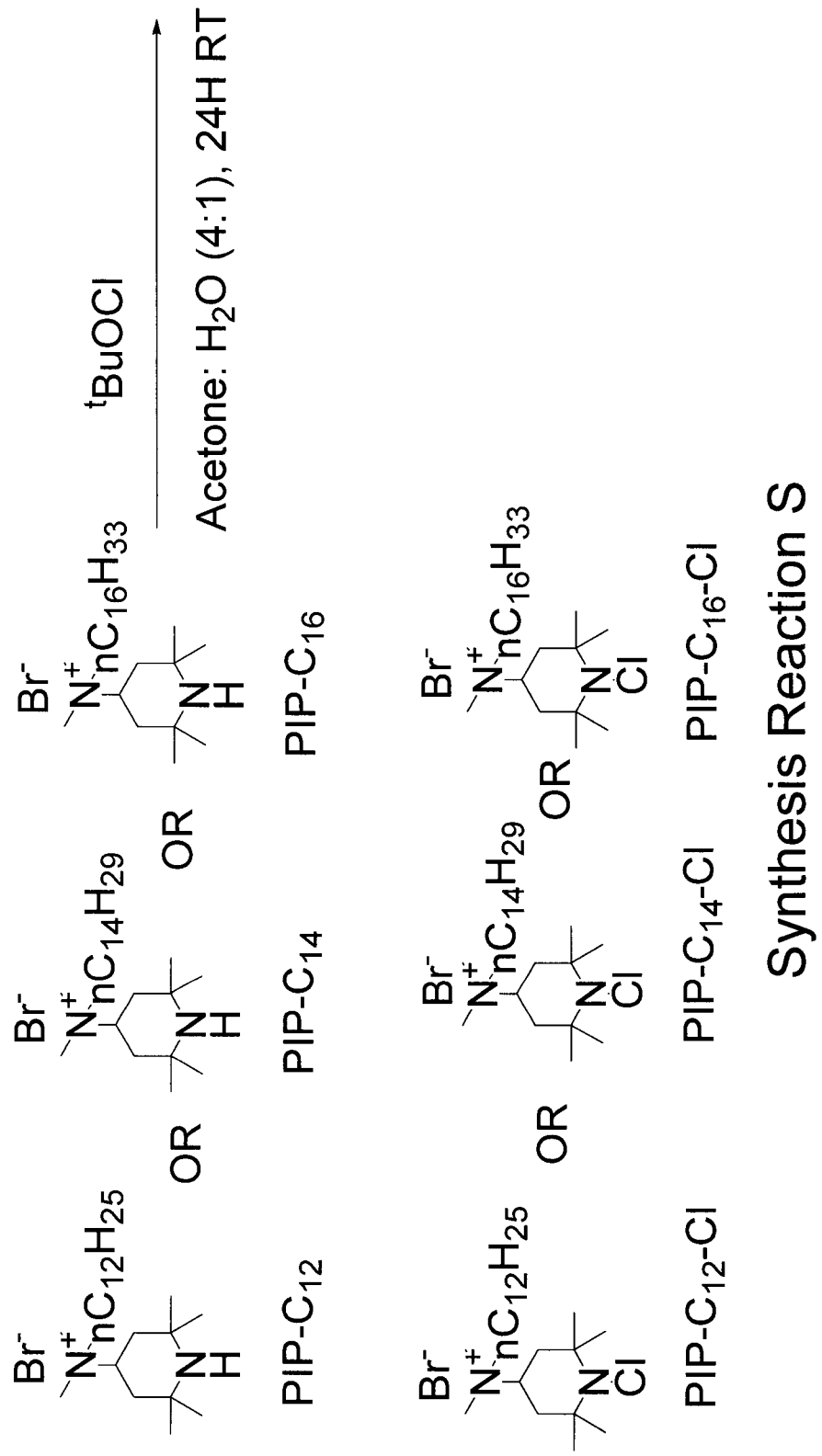
FIG. 18B shows an example of a second series of chemical modification reactions for enhancing the biocidal activity of the compounds shown in FIG. 18A.

FIG. 18B shows an example of a series of reactions that chemically modify the PIP-C12, PIP-C14 or the PIP-C16 compounds so that these compounds have biocidal activity or increased biocidal activity. This series of reactions is collectively referred to as Synthesis Reaction S and it comprises at least one step that halogenates the N-halamine precursor group within each of the PIP-012, PIP-C14 or the PIP-C16 compounds.

To make the PIP-C12-Cl compound, about 1.0 eq of PIP-C12 was dissolved in about 2 mL of an acetone/water mixture (4:1 v/v) for about 1 hour and later stirred at room temperature for about 24 hours. The purity of the PIP-C12-Cl compound was about 99% as verified by NMR using $D_2O$ and the yield of this reaction-product compound was about 98%.

To make the PIP-C14-Cl compound, about 1.0 eq of PIP-C14 was dissolved in about 2 mL of an acetone/water mixture (4:1 v/v) and then about 3.0 eq of tert-butoxy-hypochlorite (t-BuOCl) was added. The reaction was stirred at about 0° C. for about 1 hour and later stirred at room temperature for about 24 hours. The purity of the PIP-C14-Cl compound was about 99% as verified by NMR using $D_2O$ and the yield of this reaction-product compound was about 99%.

To make the PIP-C16-Cl compound, about 1.0 eq of PIP-C16 was dissolved in about 2 mL of an acetone/water mixture (4:1 v/v) and then about 3.0 eq of tert-butoxy-hypochlorite (t-BuOCl) was added. The reaction was stirred at about 0° C. for about 1 hour and later stirred at room temperature for about 24 hours. The purity of the PIP-C16-Cl compound was about 99% as verified by NMR using $D_2O$ and the yield of this reaction-product compound was about 99%.

Figure 19:
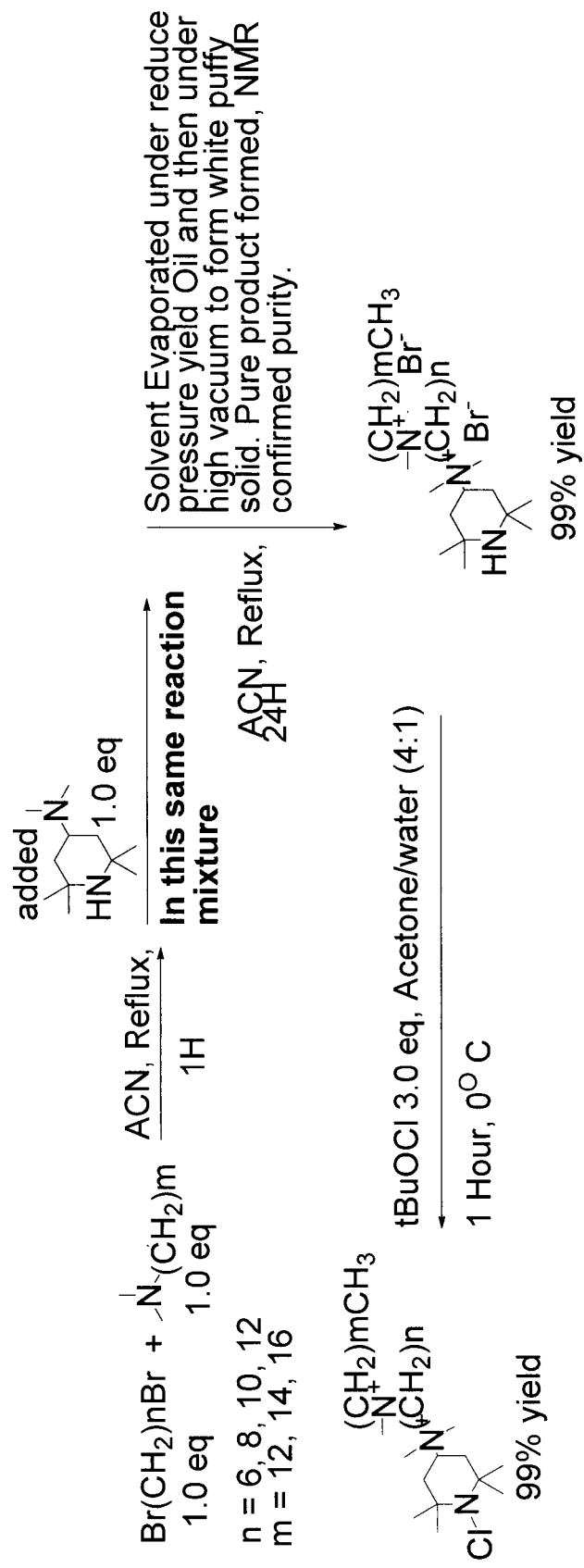
FIG. 19 is an example of a synthesis reaction series for producing a reaction-product compound with two cationic centers according to an embodiment of the present disclosure that may be used as a component of a liquid disinfectant formulation.

FIG. 19 shows another example of a series of reactions that use DMATMP as a reactant for synthesizing a halogenated reaction-product compound. This series of reactions is collectively referred to as Synthesis Reaction T and it comprises at least four steps. The Synthesis Reaction T produces a reaction-product compound with an N-halamine precursor group, two cationic centers, and two carbon chains. In this example, the reaction-product compound is referred to as PIP-$(CH_2)$n-$(CH_2)$m$CH_3$. PIP refers to the cyclic N-halamine precursor group piperidine. $(CH_2)$n refers to the carbon chain between the first cationic center, and the second cationic center, both of which are each a QAS and n is 6 to 12. $(CH_2)$m refers to the carbon chain that is connected to the second cationic center and m is between 12 and 16.

To make PIP-C6-C12, about 1.0 eq of 1, 6-dibromo-hexane and about 1.0 eq of N, N-dimethyldodecane were dissolved in 50 mL of acetonitrile within a reaction vessel. The reaction mixture was refluxed and stirred for about 1 hour using a reflux condenser at about 85° C.

Upon completion of the above steps, about 1.0 eq of DMATMP was dissolved in about 5 mL of acetonitrile and added into the above reaction mixture and refluxed for about 24 hours at about 85° C. The solvent was evaporated under reduced pressure to produce an oil. Then the oil was put under vacuum (starting from low to high vacuum) to produce a white puffy solid, which remained under vacuum for about 4 hours. The purity of the PIP-C6-C12 compound was about 99% as verified by NMR using $D_2O$ (not shown) and the yield of this reaction-product compound was about 98.2%.

To make the PIP-C6-C12-Cl compound, about 1.0 eq of PIP-C6-C12 was dissolved in about 2 mL of an acetone/water mixture (4:1) and about 3.0 eq of tert-butoxy-hypochlorite (t-BuOCl) was then added. The reaction was stirred at about 0° C. for about 1 hour and then stirred at room temperature for about 24 hours. The solvent was evaporated under reduced pressure. The purity of the PIP-C6-C12-Cl compound was about 99% as verified by NMR using $D_2O$ (not shown) and the yield of this reaction-product compound was about 99%.

As shown in FIG. 19, similar methodologies were used to make the following compounds with similar purities and yields: PIP-C6-C14; PIP-C6-C14-Cl; PIP-C6-C16; PIP-C6-C16-Cl; PIP-C8-C14; PIP-C8-C14-Cl; PIP-C10-C14; PIP-C10-C14-Cl; PIP-C12-C12; PIP-C12-C12-Cl; PIP-C12-C14; PIP-C12-C14-Cl; PIP-C12-C16; and PIP-C12-C16-Cl.

Figure 20:
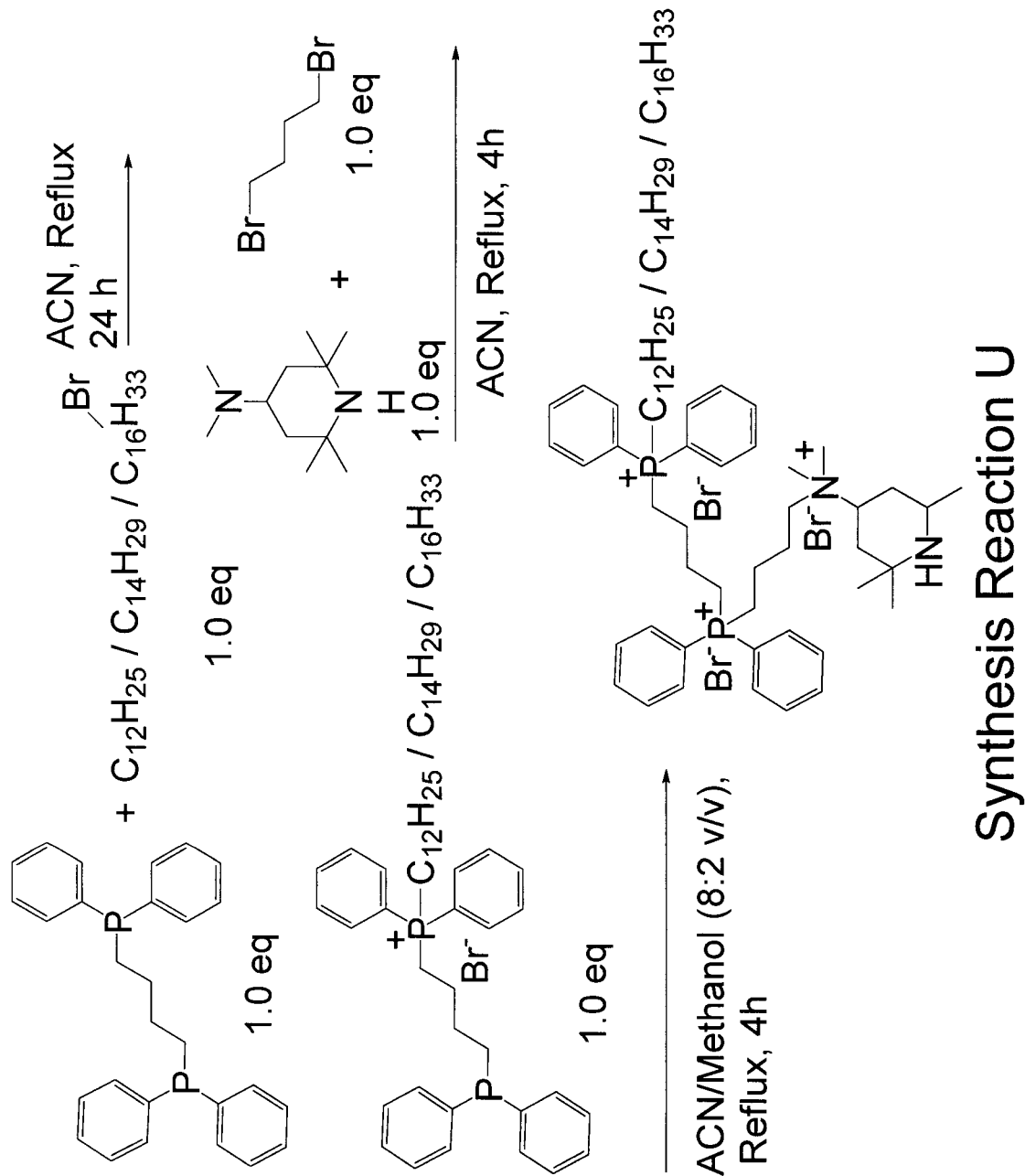
FIG. 20 is an example of a synthesis reaction series for producing a reaction-product compound with three cationic centers according to an embodiment of the present disclosure that may be used as a component of a liquid disinfectant formulation.

FIG. 20 shows another example of a series of reactions that use DMATMP as a reactant for synthesizing a reaction-product compound. This series of reactions is referred to as Synthesis Reaction U and it produces a reaction-product compound with an N-halamine precursor group, three cationic centers, and a carbon chain attached to the third cationic center. In this example, the reaction-product compound is referred to as PIP-C4-PPh2-C4-PPh2-C12/C14/

C16. PIP refers to the cyclic N-halamine precursor group piperidine. The first C4 refers to the four-carbon chain between the first cationic center, and the second cationic center. The first cationic center is a QAS and the second cationic center is a phosphate-based cationic center (P) with two phenyl groups attached thereto (Ph2). The second C4 refers to the four-carbon chain between the second cationic center, and the third cationic center, which is also a phosphate-based cationic center (P) with two phenyl groups attached thereto (Ph2). C12/C14/C16 refers to a carbon chain that is connected to the third cationic center and that can be a saturated 12, 14 or 16 carbon chain.

To make one of the PIP-C4-PPh2-C4-PPh2-C12/C14/C16 compounds, about 1.0 eq of 1, 4-bis (diphenylphosphino) butane and about 1.0 eq of bromo-dodecane or bromo-tetradecane or bromo-hexadecane were dissolved in acetonitrile in a reaction vessel and refluxed for about 24 hours. The reaction mixture evaporated and appeared as a white precipitate, which was dissolved again by adding methanol in a drop-wise fashion until a clear solution appeared.

In a second reaction vessel, about 1.0 eq of TMTMP and about 1.0 eq of 1, 4-dibromobutane were dissolved in acetonitrile. The reaction mixture was stirred under reflux condition for about 4 hours in acetonitrile and the solvent was evaporated, which resulted in a white precipitate.

The contents of the two reaction vessels were combined and dissolved in a toluene/methanol mix. The reaction mixture was stirred again under reflux condition for about 24 hours in a toluene/methanol mixture. The solvent was evaporated and dried under vacuum to produce a white precipitate.

Figure 21:
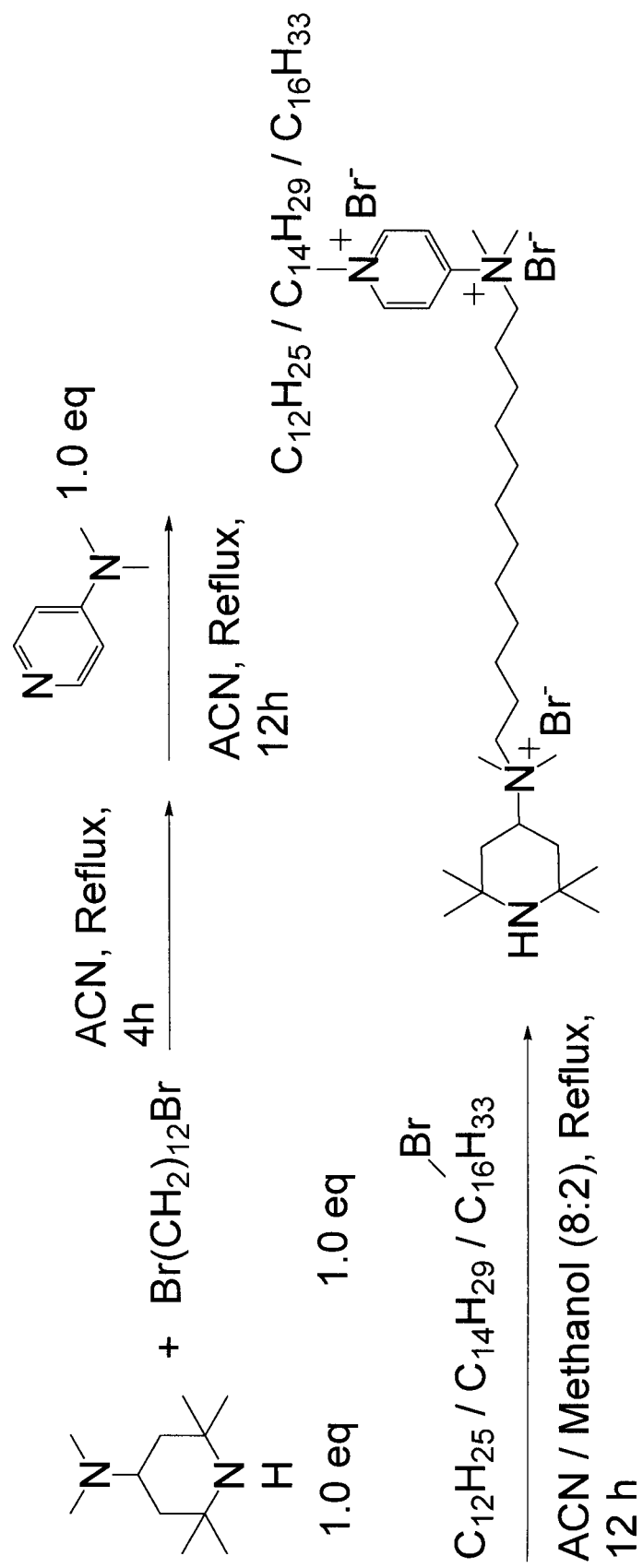
FIG. 21 is an example of a synthesis reaction series for producing a reaction-product compound with three cationic centers according to an embodiment of the present disclosure that may be used as a component of a liquid disinfectant formulation.

FIG. 21 shows another example of a series of reactions that use DMATMP as a reactant for synthesizing a reaction-product compound. This series of reactions is referred to as Synthesis Reaction V and it produces a reaction-product compound with an N-halamine precursor group, three cationic centers, and a carbon chain attached to the third cationic center. In this example, the reaction-product compound is referred to as PIP-C12-DMAP-C12/C14/C16. PIP refers to the cyclic N-halamine precursor group piperidine. C12 refers to the twelve-carbon chain between the first cationic center, and the second cationic center. The first and second cationic centers are each a QAS. DMAP refers to the third cationic center and C12/C14/C16 refers a carbon chain that is connected to the third cationic center and that can be a saturated twelve-, fourteen- or sixteen-carbon chain.

To make one of the PIP-C12-DMAP-C12/C14/C16 compounds, about 1.0 eq of DMATMP and about 1.0 eq of 1, 12-dibromobutane were dissolved in acetonitrile within a reaction vessel and refluxed for about 4 hours. The reaction mixture appeared as a clear solution. Following which, about 1.0 eq of 4-N, N-dimethylamino pyridine was added and the mixture was refluxed for about 12 hours. Following which, about the 1.0 eq of bromo-dodecane or bromo-tetradecane or bromo-hexadecane was added and refluxed for about 12 hours in a mixture of acetonitrile/methanol (8:2 v/v). The solvent was evaporated and dried under vacuum.

Further Examples for Coating Soft-Surfaces

Figures 33, 33A:
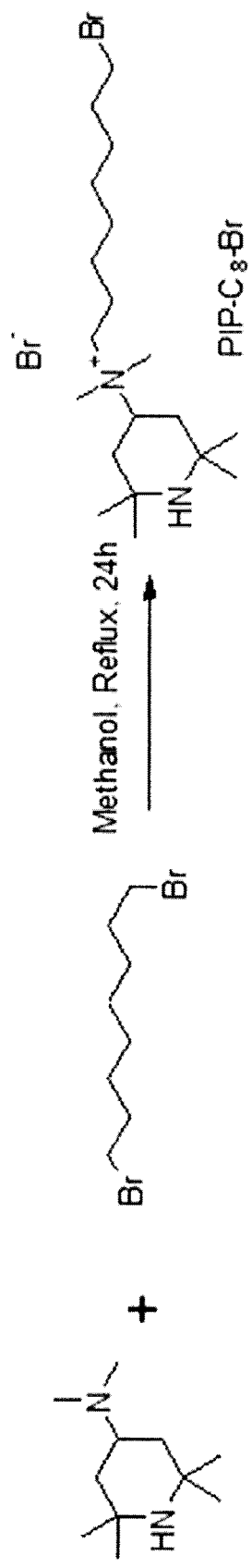
Figure 33B:
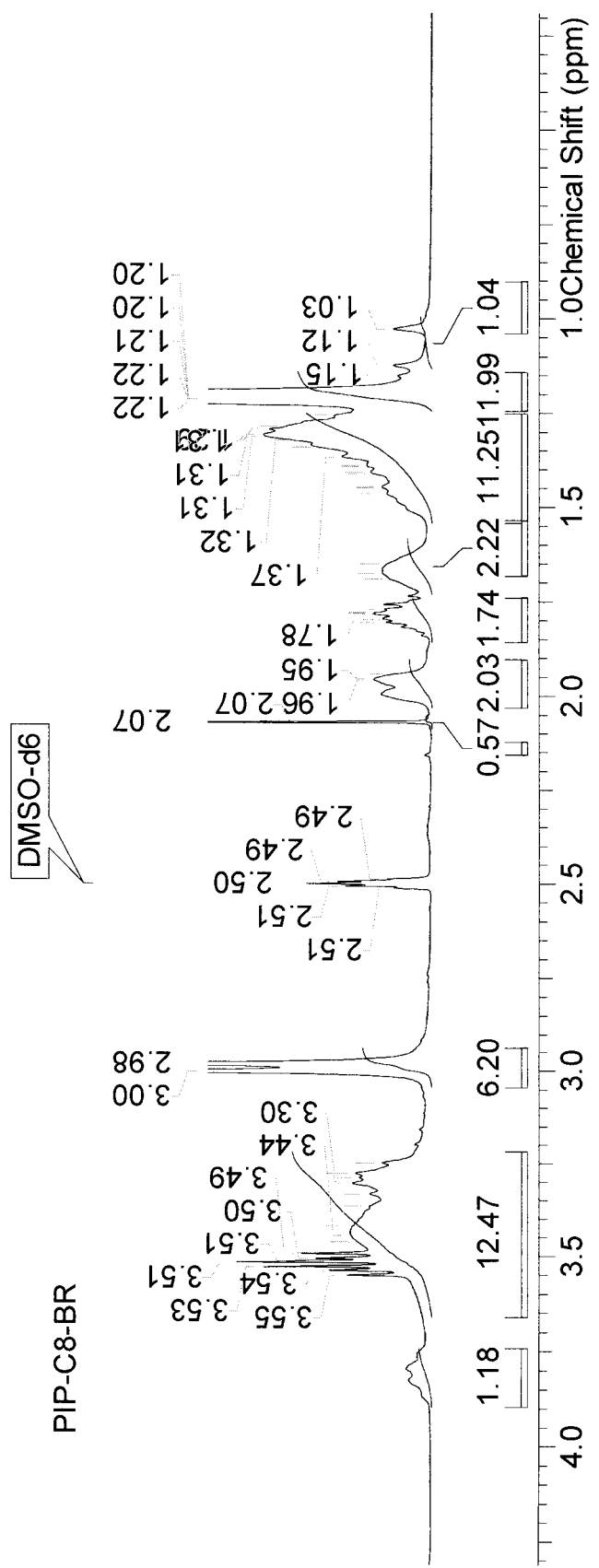

FIG. 33A shows another example of a reaction that uses a compound of Formula 2 for making a reaction-product compound with an N-halamine precursor group and a cationic center. The following were added to a reaction vessel: 1.0 eq. of N,N-dimethylamino-2,2,6,6-tetramethyl-piperidine and dropwise addition of 1.0 eq. 1,8-dibromooctane dissolved in methanol, followed by reflux for 24 hours. The solvent was evaporated and dried under vacuum and recovered as a white solid. The purity of the compound was verified by NMR in d6-DMSO (FIG. 33B), which was 98%. The yield of the product was 99%.

Figures 34, 34A:
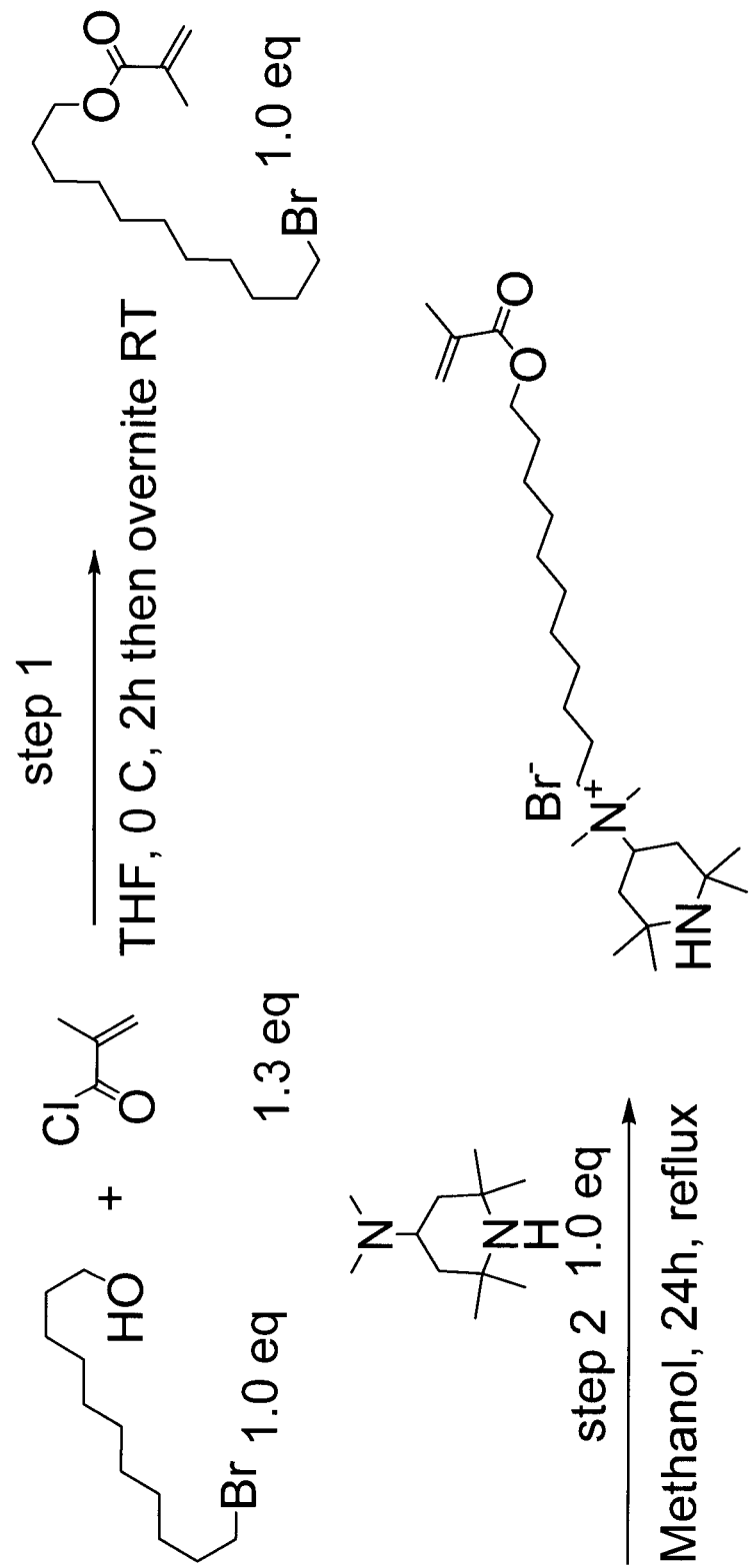

FIG. 34A shows another example of a set of reactions that uses a compound of Formula 2 for making a reaction-product compound with an N-halamine precursor group, a cationic center and a methyl-methacrylate CIG. In a first step 1 the following were added into a reaction vessel: 1.0 eq. of 11-bromoundecanol dissolved in anhydrous THF under Nitrogen atmosphere and kept at 0° C. To this 1.3 eq. of Methacryloyl chloride were added and stirred at 0° C. for two hours and then left for overnight under room temperature conditions. After 24 Hours, the solvent was evaporated completely and the remaining intermediate was washed 3 times with NaHCO$_3$ (saturated solution) and extracted with ethyl acetate until the aqueous layer turned basic. The organic layer was evaporated to produce a light yellow oil which semi solidified as a white gel. The purity of the compound was verified by NMR in CDCl3, which was around 98%. The yield of the product was 89%.

Figure 34B:
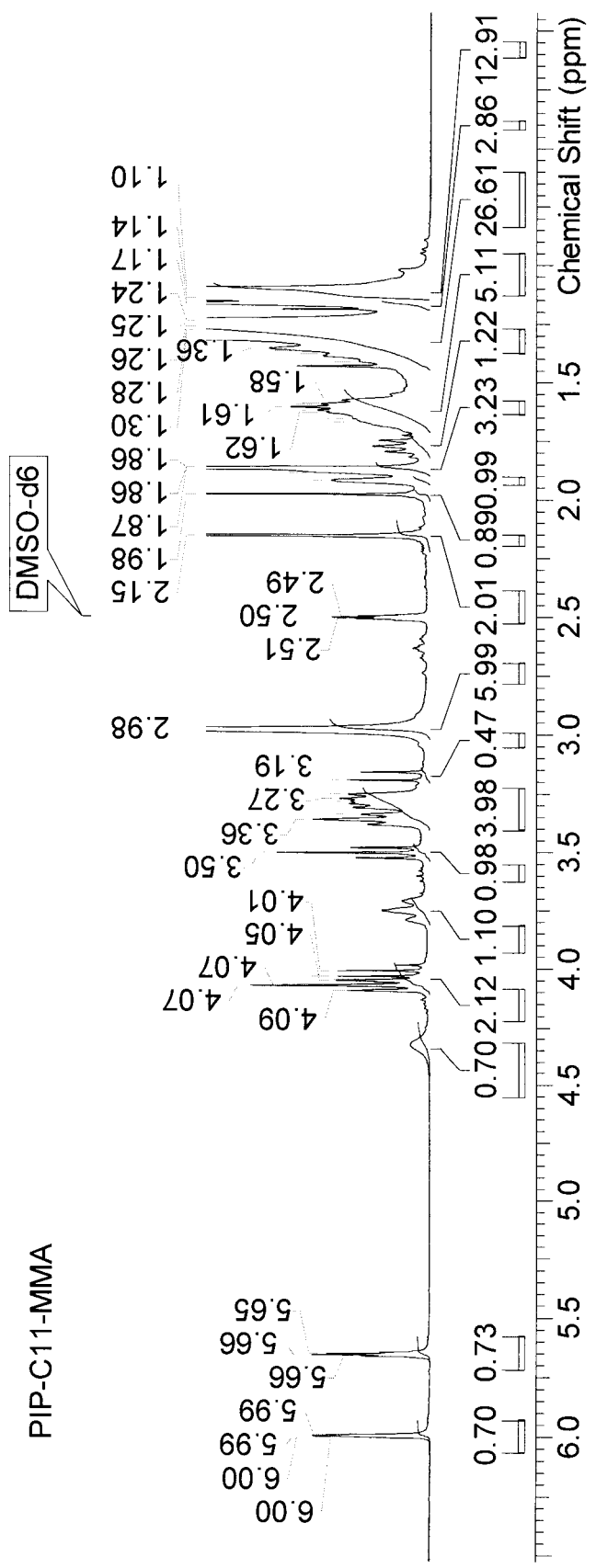
Figure 55:
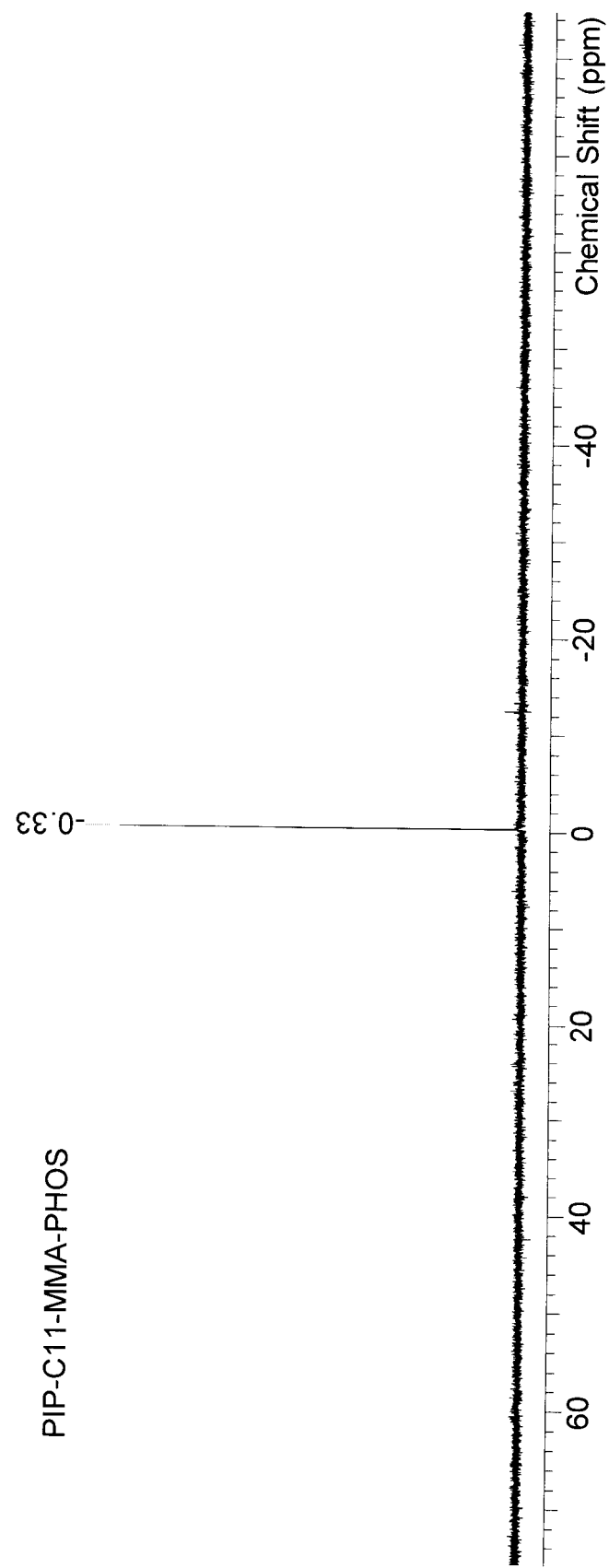
FIG. 55 is an example of a phosphorous-31 NMR spectrum from the reaction-compound shown in FIG. 34.

In a second step another reactant 1.0 eq of N,N-dimethylamino-2,2,6,6-tetramethyl-piperidine was added to the 1 eq. of step 1 product. The reaction mixture was stirred under reflux condition for 24 hours in methanol. The solvent was evaporated and dried under vacuum. The purity of the compound was verified by NMR in DMSO-d6 (FIG. 34B), which was 98%. FIG. 55 shows the phosphorous-31 NMR spectrum from this reaction-product compound. The yield of the product was 98%.

Figures 35, 35A:
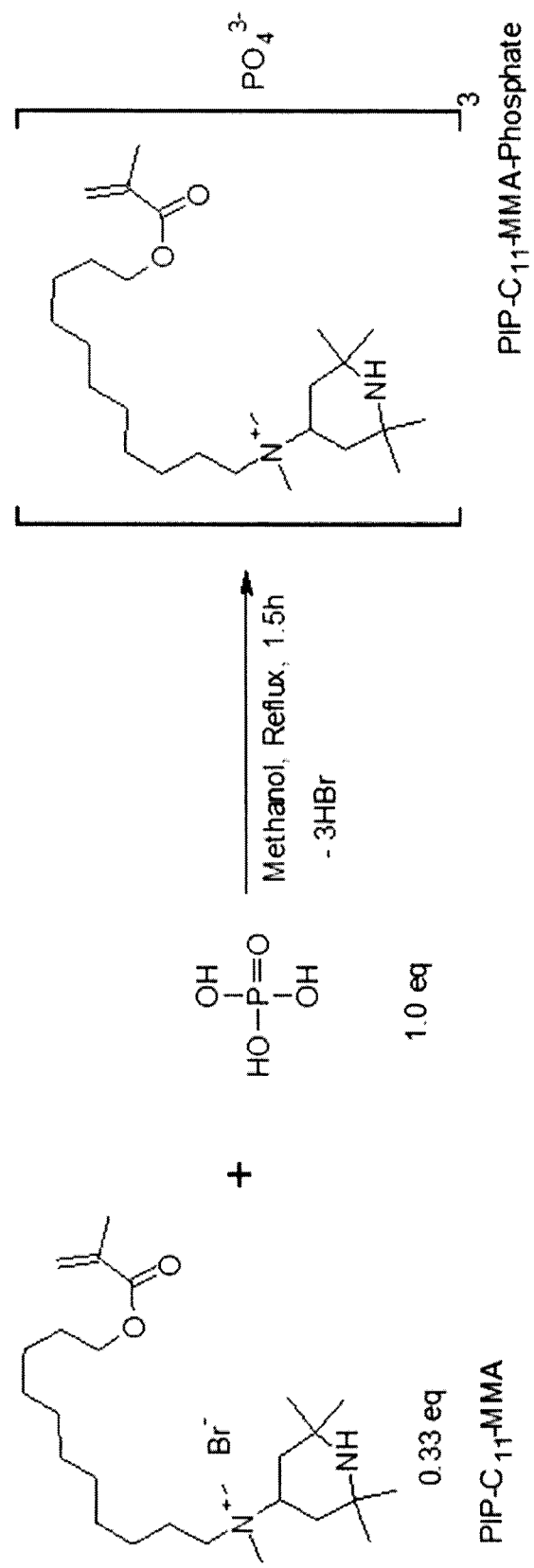
Figure 35B:
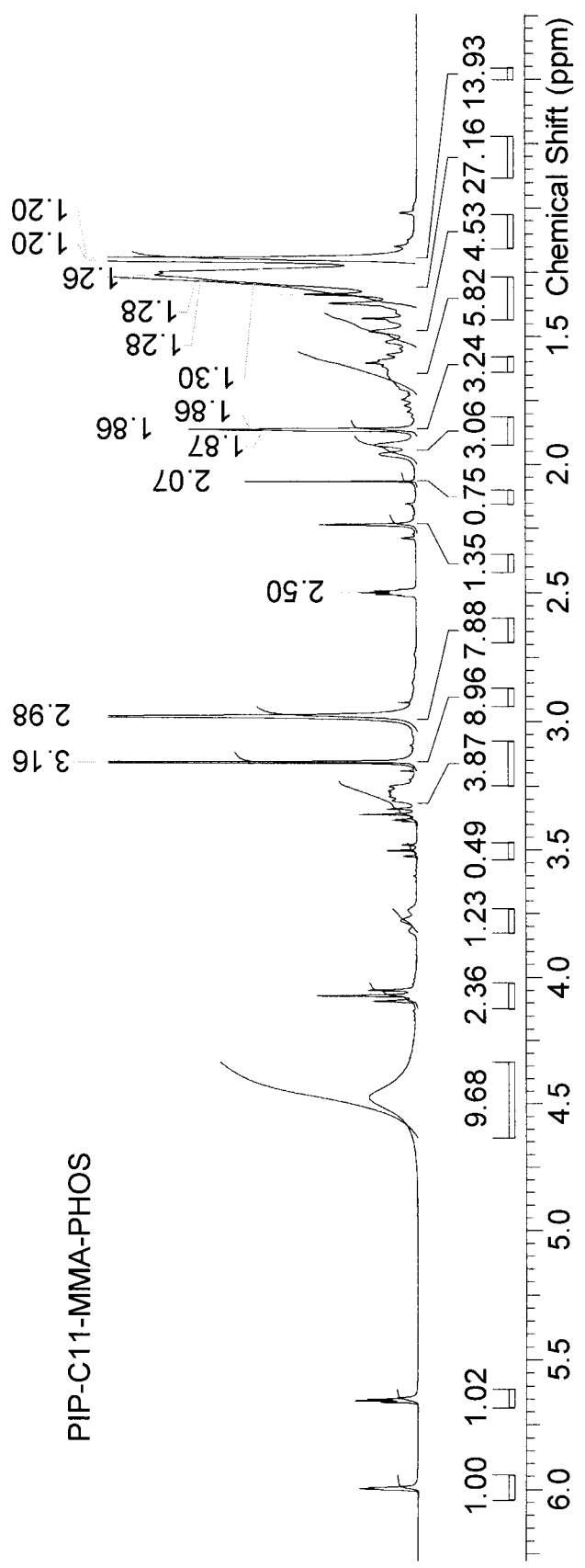
Figure 56:
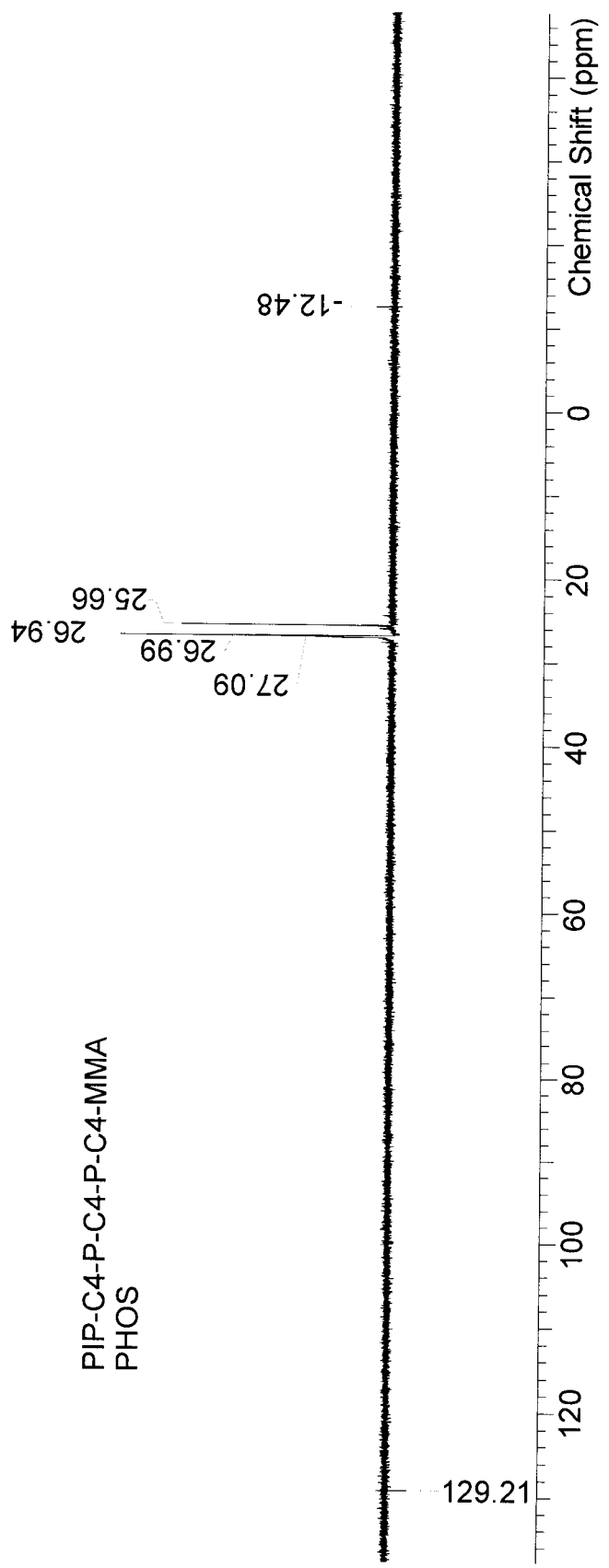
FIG. 56 is an example of a phosphorous-31 NMR spectrum from the reaction-compound shown in FIG. 35.

FIG. 35A shows another example of a set of reactions that uses a compound of Formula 2 for making a reaction-product compound with an N-halamine precursor group, a cationic center and a methyl-methacrylate CIG. The following were added to a reaction vessel: 0.33 eq of PIP-C11-MMA, 1.0 eq of Phosphoric acid dissolved in methanol, mixed and refluxed for 1.5 hours. The solvent of reaction mixture evaporated to recover an off-white gel. The purity was checked by NMR (proton as well as phosphonium-31) (99%) (FIG. 35B). FIG. 56 shows the phosphorous-31 NMR spectrum from this reaction-product compound. The yield was 99%.

Figures 36, 36A:
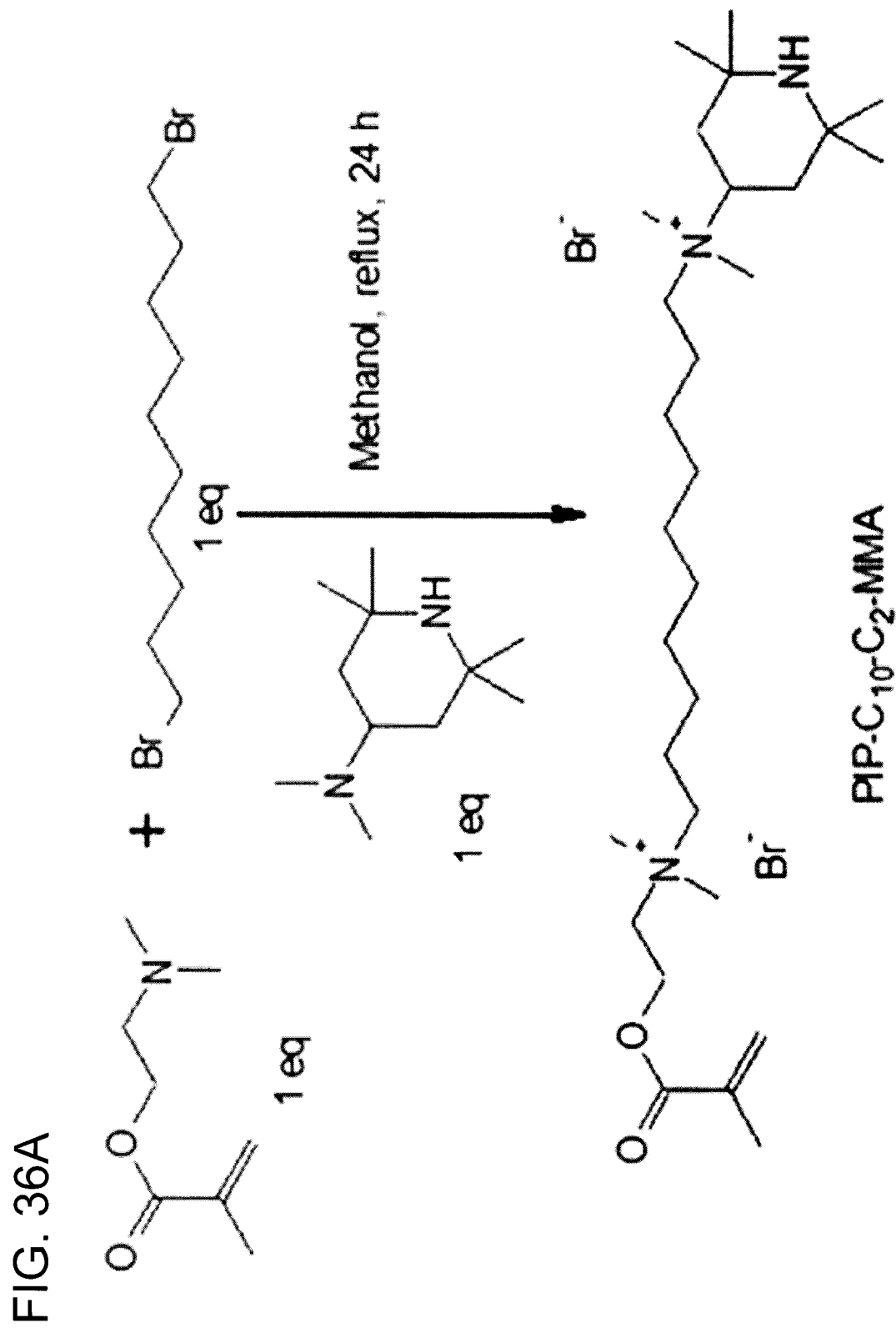
Figure 36B:
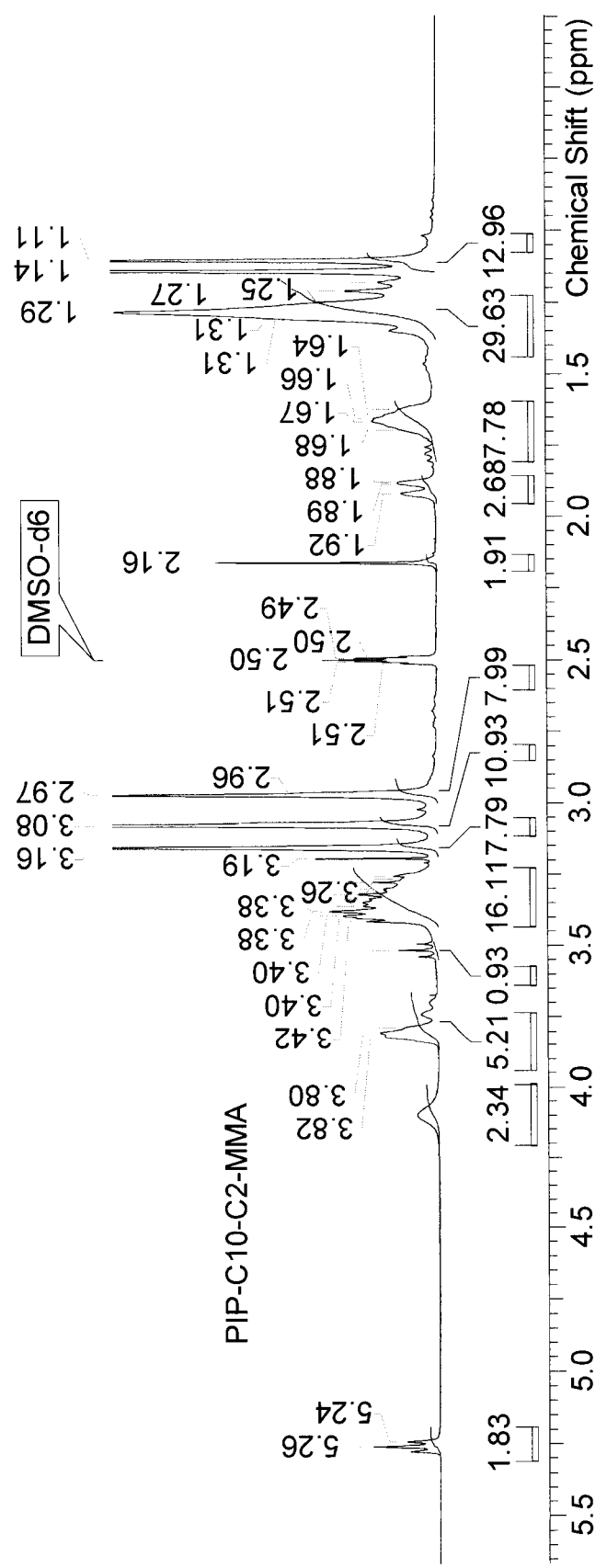
Figure 57:
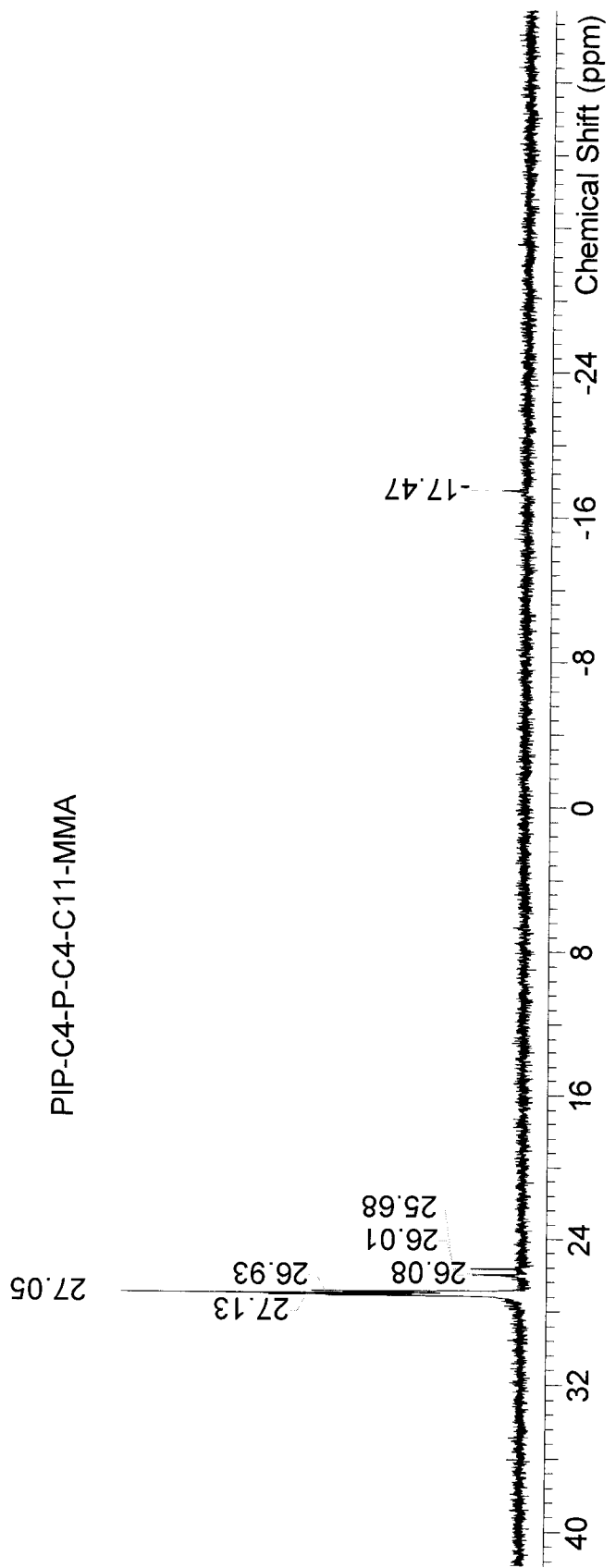
FIG. 57 is an example of a phosphorous-31 NMR spectrum from the reaction-compound shown in FIG. 41.

FIG. 36A shows another example of a set of reactions that uses a compound of Formula 2 for making a reaction-product compound with an N-halamine precursor group, a cationic center and a methyl-methacrylate CIG. The following were added to a reaction vessel: 1.0 eq of 1,10-dibromodecane dissolved in methanol, 1.0 eq of 2-(N,N-Dimethylaminoethylene)methacrylate dissolved in methanol separately, these were added dropwise for an hour to the reaction vessel and refluxed for 24 hours. To the same reaction mixture added the third reactant 1.0 eq of N,N-dimethylamino-2,2,6,6-tetramethyl-piperidine. The reaction mixture was stirred under reflux conditions for 24 hours in methanol. The solvent was evaporated and dried under vacuum to form a clear gummy substance or a white semi-solid. The purity of the compound was verified by NMR in DMSO-d6 (FIG. 36B), which was about 98%. FIG. 57 shows the phosphorous-31 NMR spectrum from this reaction-product compound. The yield of the product was 98%.

Figures 37, 37A:
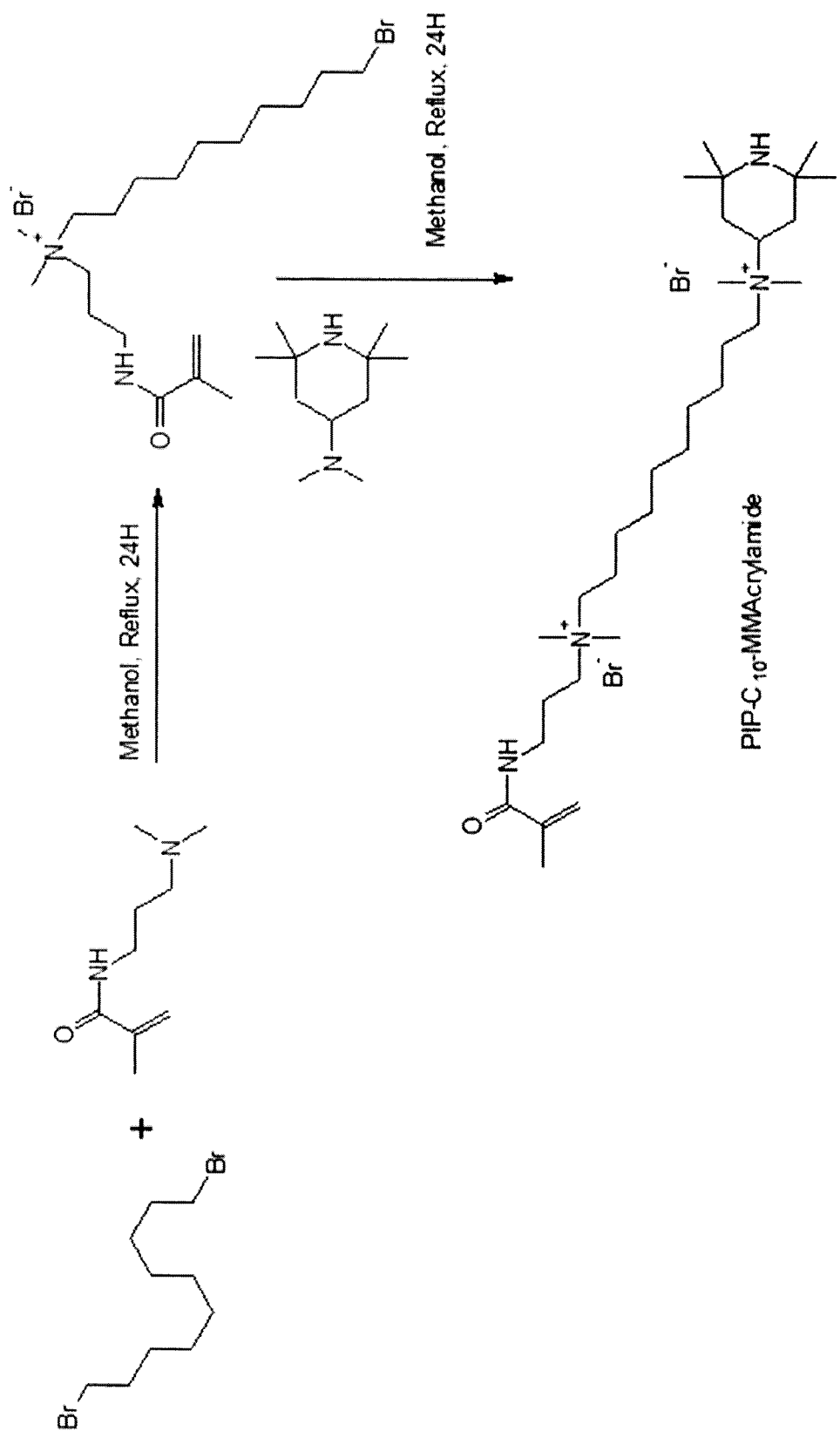
Figure 37B:
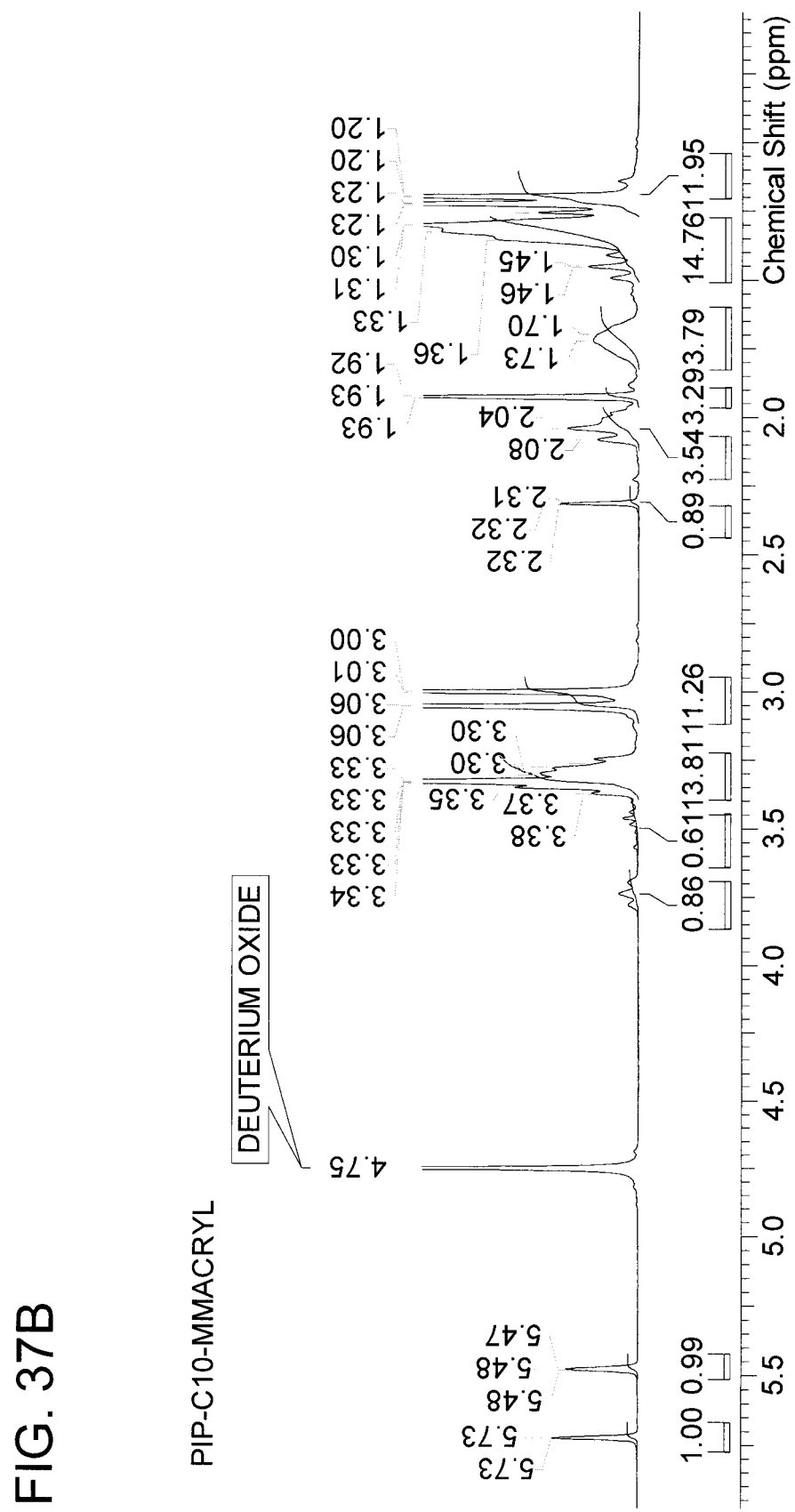

FIG. 37A shows another example of a set of reactions that uses a compound of Formula 2 for making a reaction-product compound with an N-halamine precursor group, a cationic center and a methyl-methacrylate CIG. The following were added to a reaction vessel: 1.0 eq of 1,10-dibromodecane dissolved in methanol, 1.0 eq of 2-(N,N-Dimethylaminopropylene)methacrylamide dissolved in methanol separately, these were added dropwise for an hour to the reaction vessel and refluxed for 24 hours. To the same reaction mixture a third reactant 1.0 eq of N,N-dimethylamino-2,2,6,6-tetramethyl-piperidine was added. The reaction mixture was stirred under reflux condition for 24 hours in methanol. The solvent was evaporated and dried under vacuum to form a clear gummy substance or a white semi-solid. The purity of the compound was verified by NMR in D2O (FIG. 37B), which was about 98%. The yield of the product was 98%.

Figures 38, 38A:
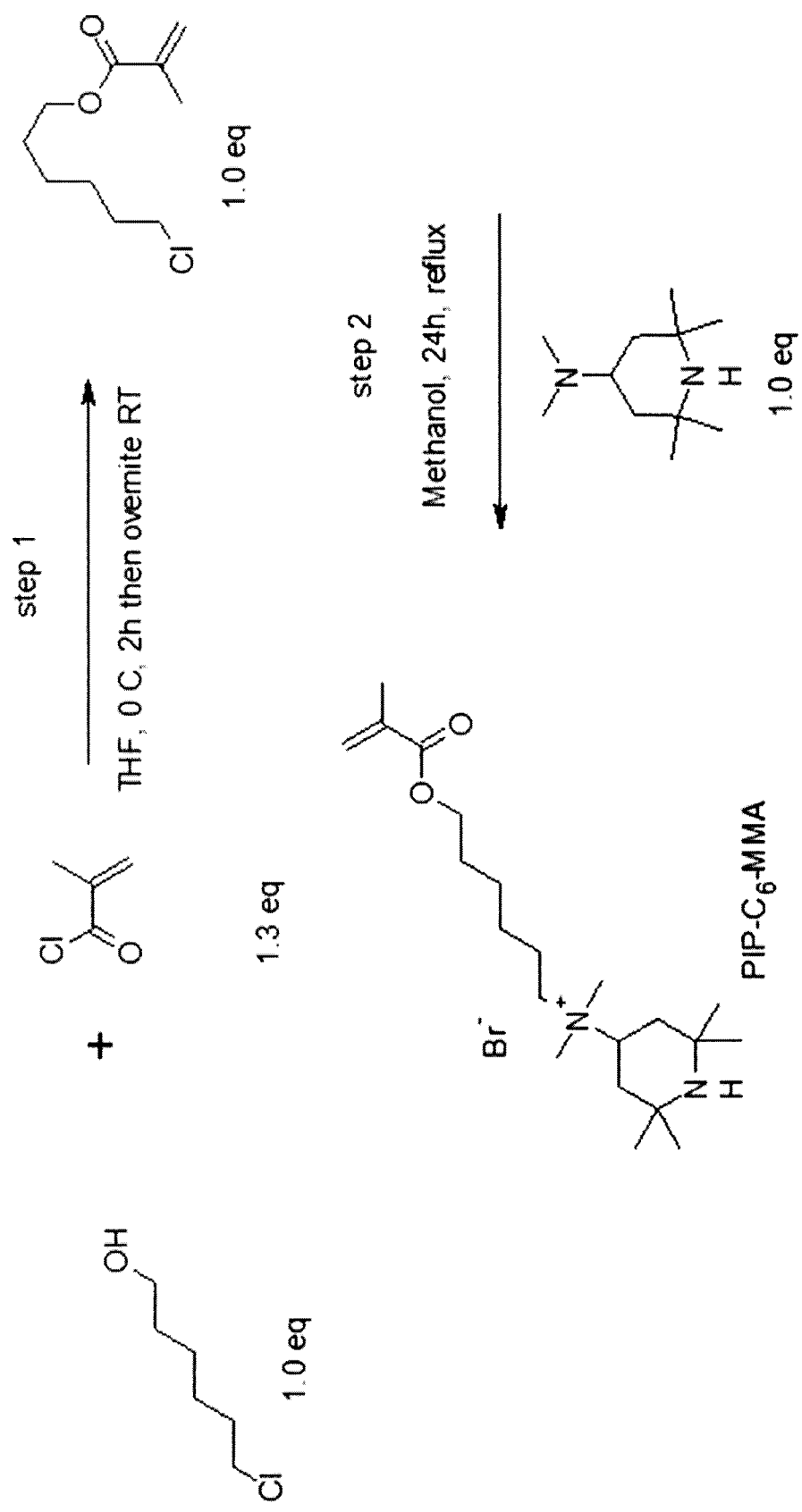
Figure 38B:
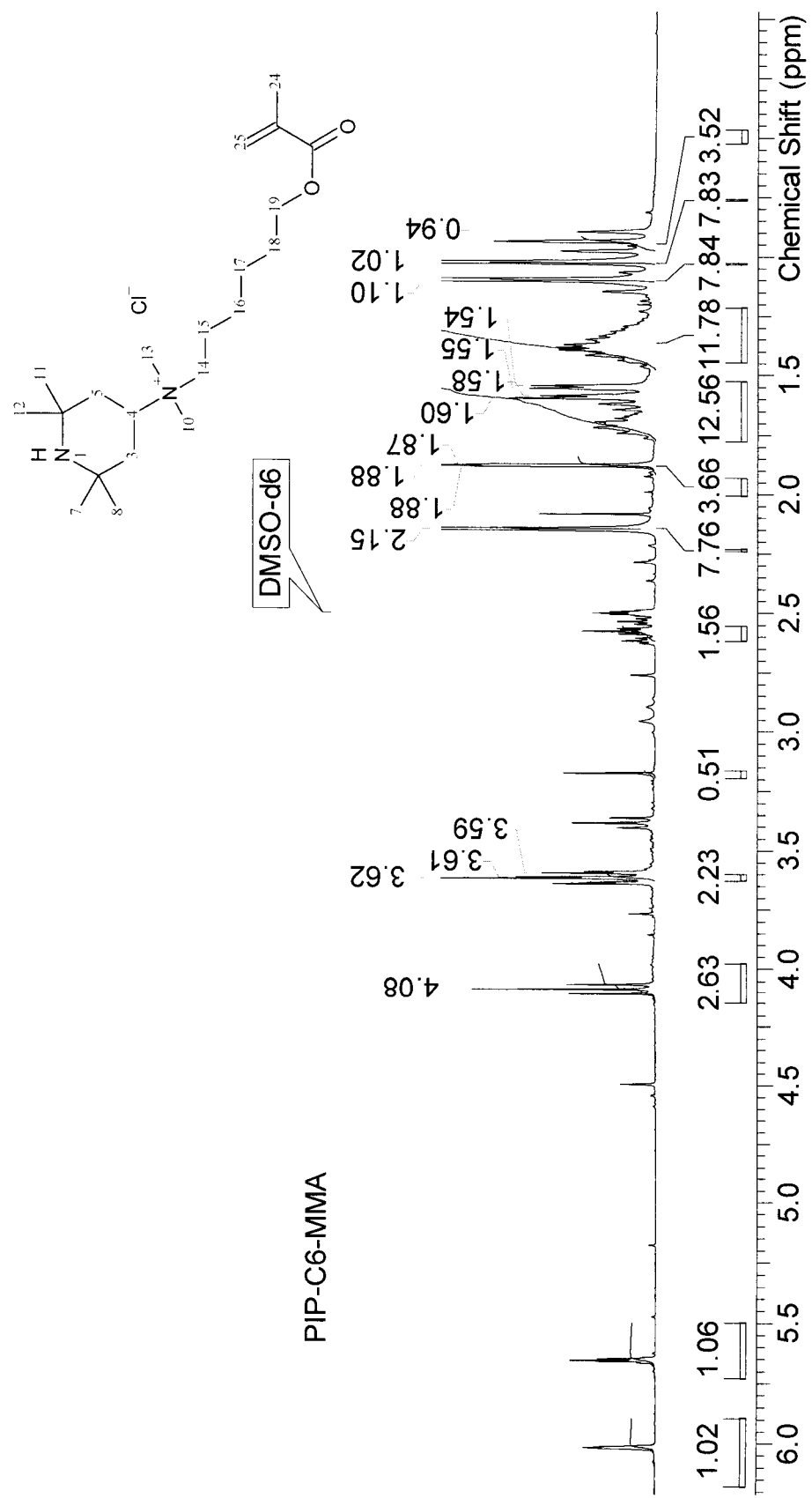

FIG. 38A shows another example of a set of reactions that uses a compound of Formula 2 for making a reaction-product compound with an N-halamine precursor group, a cationic center and a methyl-methacrylate CIG. The following were added to a reaction vessel in a first step: 1.0 eq. of 6-chlorohexanol dissolved in anhydrous THF under nitrogen and kept at 0° C. To this, 1.3 eq. of Methacryloyl chloride, stirred at 0° C. for two hours were added in a dropwise fashion and then left for overnight under room temperature conditions. After 24 Hours, the solvent evaporated. This was followed by three wash with a NaHCO$_3$ saturated solution and then extraction with ethyl acetate until the aqueous layer turned basic. Evaporated the organic layer to get light yellow oil which formed a semi-solid white gel. The purity of the compound was verified by NMR in CDCl$_3$ (not shown), which was around 98%. The yield of the product was 95%. In a second step, 1.0 eq of N, N-dimethyl-2,2,6,6-tetramethyl-piperidine was added to the step 1 reaction product. The reaction mixture was stirred under reflux conditions for 24 hours in methanol. The solvent was evaporated and dried under vacuum. The purity of the compound was verified by NMR in DMSO-d6 (FIG. 38B) and mass spec, which was about 98%. The yield of the product was 98%.

Figures 39, 39A:
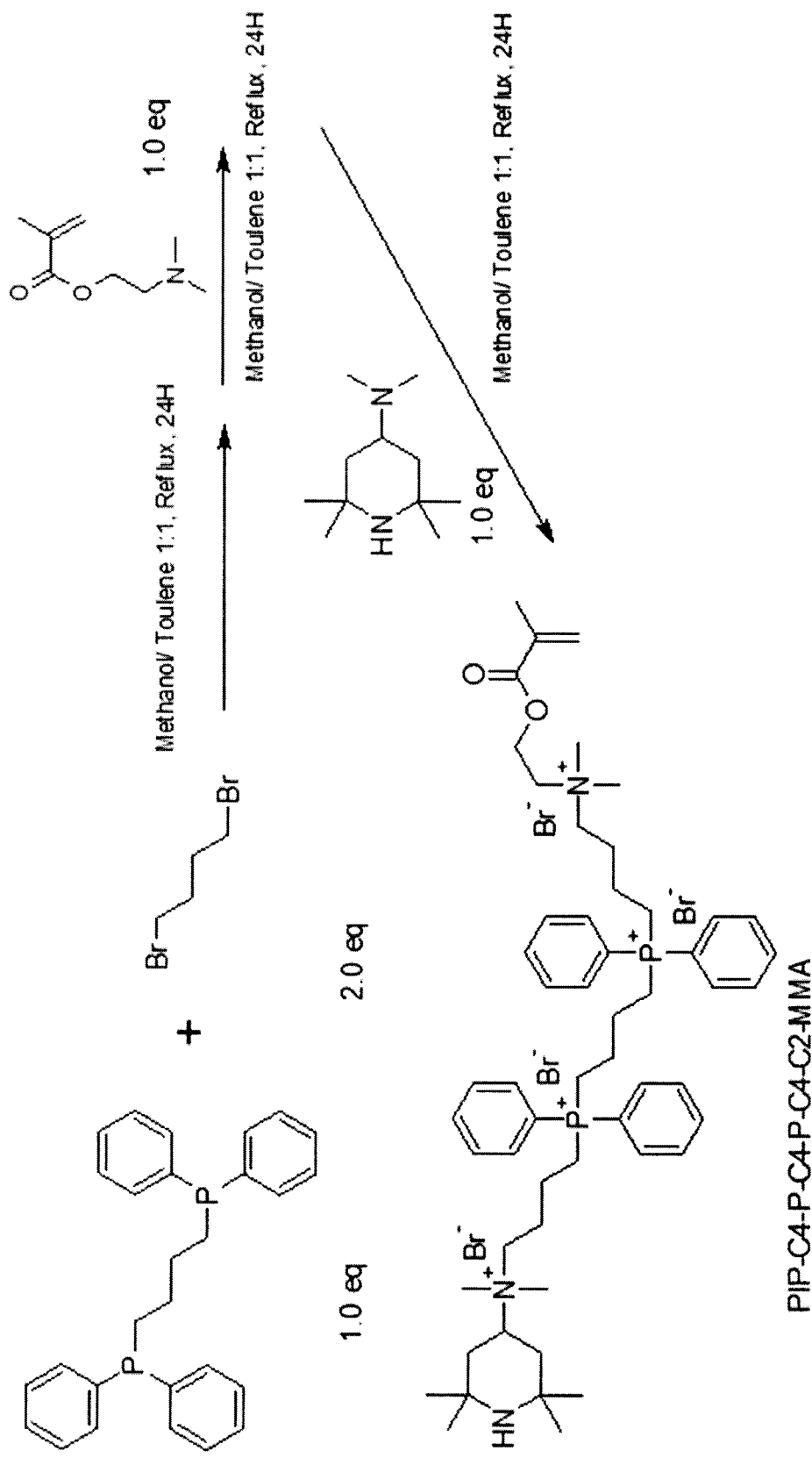
Figure 39B:
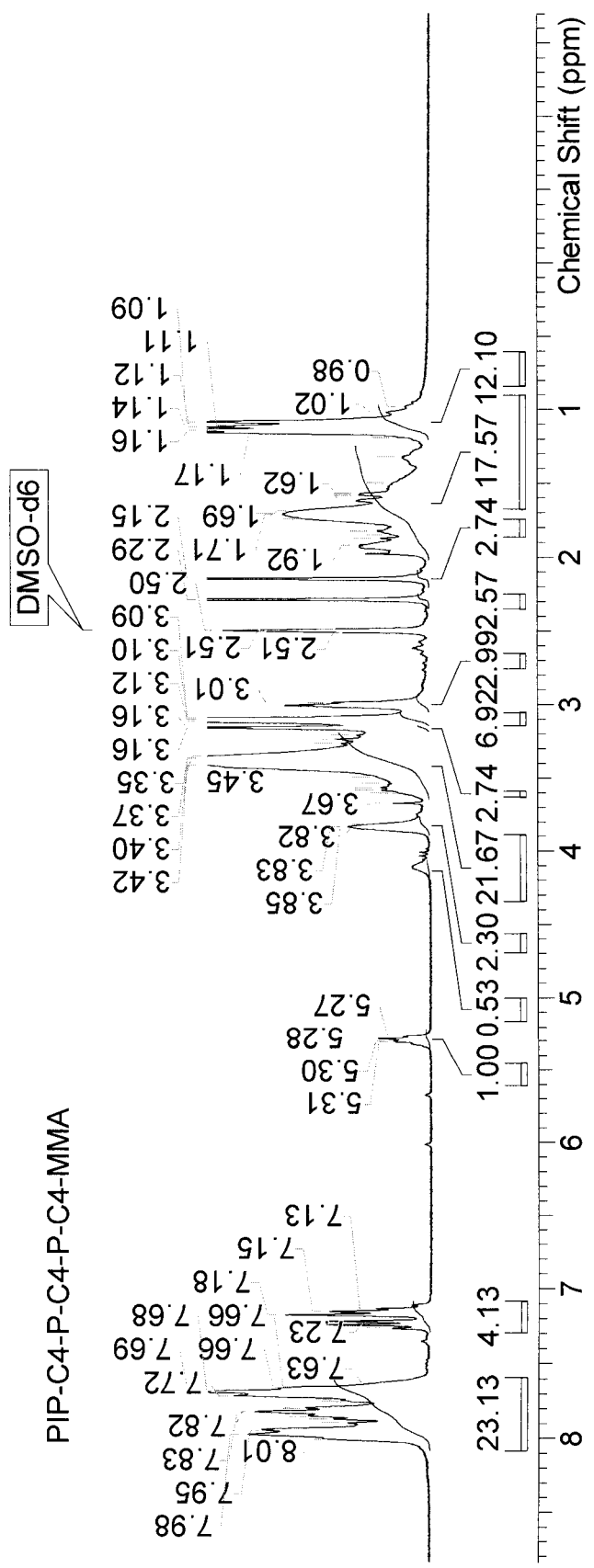

FIG. 39A shows another example of a set of reactions that uses a compound of Formula 2 for making a reaction-product compound with an N-halamine precursor group, a cationic center and a methyl-methacrylate CIG. The following were added to a reaction vessel: 1.0 eq of 1,4-Bis (diphenylphosphino)butane and 2.0 eq of 1,4-dibromobutane dissolved in toluene/methanol (1:1 v/v) and refluxed for 24 hours. In the same reaction vessel, a third reactant 1.0 eq of N,N-(Dimethylamino-ethylene)methacrylate was added and refluxed for another 24 hours. Again to the same reaction vessel a fourth reactant 1.0 eq. of N, N-dimethyl-2,2,6,6-tetramethyl-piperidine was added refluxed for another 24 hours. The solvent evaporated and was dried under vacuum to produce a white precipitate. NMR (proton and phosphorus-31) confirmed a purity of about 98% (not shown). The yield of the product was 98%.

Figures 40, 40A:
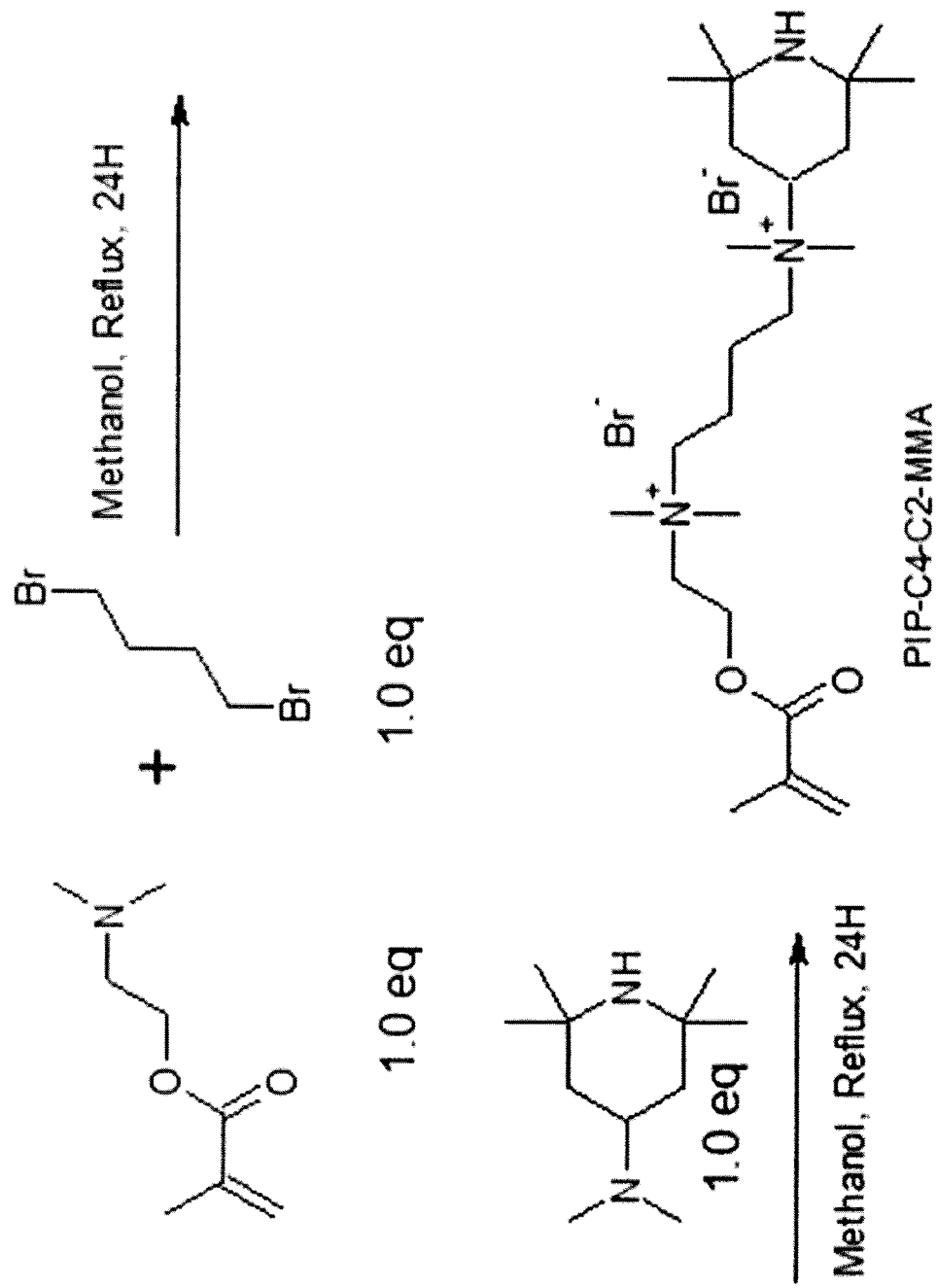

FIG. 40A shows another example of a set of reactions that uses a compound of Formula 2 for making a reaction-product compound with an N-halamine precursor group, a cationic center and a methyl-methacrylate CIG. The following were added to a reaction vessel: 1.0 eq of N,N-(Dimethylaminoethylene)methacrylate and 1.0 eq of 1,4-dibromobutane dissolved in methanol which refluxed for 24 hours. After that added a third reactant 1.0 eq of N,N-dimethylamino-2,2,6,6-tetramethyl-piperidine was added. The reaction mixture was stirred under reflux condition for 24 hours in methanol. The solvent evaporated and dried under vacuum. The purity of the compound checked by NMR in D2O, which was around 98%. The yield of the product was 98%.

FIG. 40B shows another example of a set of reactions that uses a compound of Formula 2 for making a reaction-product compound with an N-halamine precursor group, a cationic center and a methyl-methacrylate CIG. The following were added to a reaction vessel: 1.0 eq of 1,8-dibromooctane dissolved in methanol, 1.0 eq of 2-(N,N-Dimethylaminoethylene)methacrylate dissolved in methanol separately, were added dropwise for an hour to the reaction vessel and refluxed for 24 hours. To the same reaction mixture a third reactant 1.0 eq of N,N-dimethylamino-2,2, 6,6-tetramethyl-piperidine was added. The reaction mixture was stirred under reflux condition for 24 hours in methanol. The solvent evaporated and was dried under vacuum to form a gummy, clear semi-solid. The purity of the compound was verified by NMR in DMSO-d6, which was 98%. The yield of the product was 98%.

Figures 41, 41A:
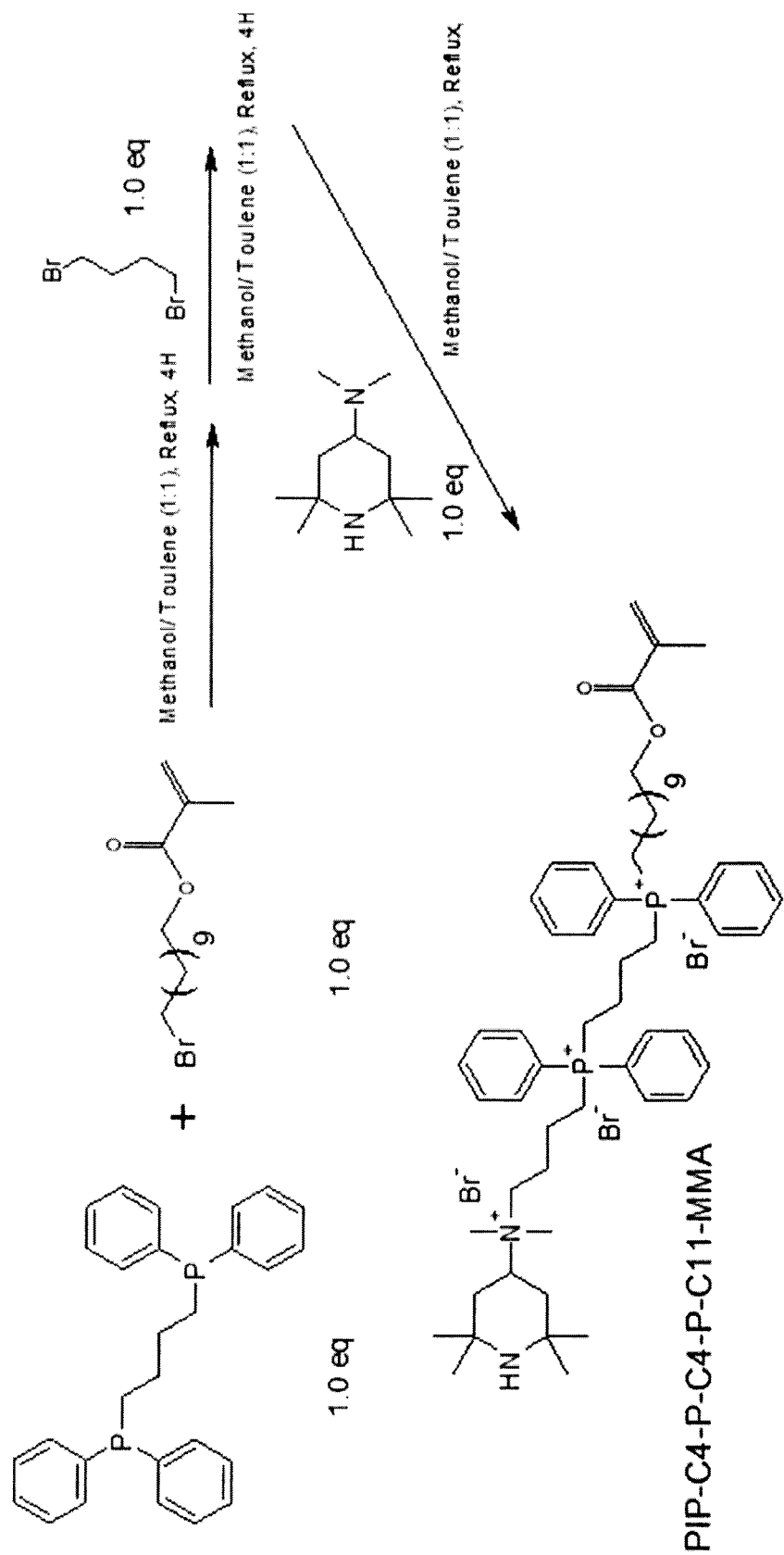
Figure 41B:
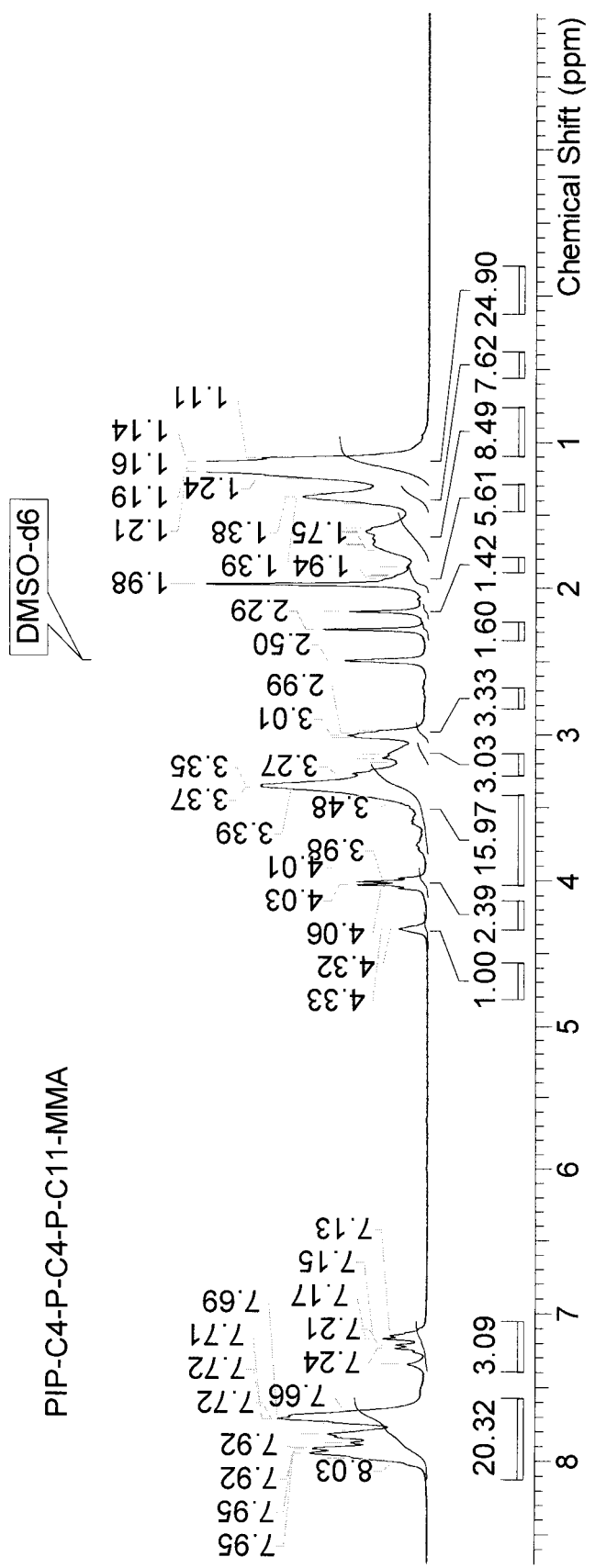

FIG. 41A shows another example of a set of reactions that uses a compound of Formula 2 for making a reaction-product compound with an N-halamine precursor group, a cationic center and a methyl-methacrylate CIG. The following were added to a reaction vessel: 1.0 eq of 1,4-Bis (diphenylphosphino)butane and 1.0 eq of 11-bromo-undecane-methylmethacrylate dissolved in toluene/methanol (1:1 v/v) and were refluxed for 24 hours. In the same reaction vessel, a third reactant 1.0 eq of 1,4-dibromobutane was added and refluxed for another 24 hours. A fourth reactant 1.0 eq. of N,N-dimethylamino-2,2,6,6-tetramethyl-piperidine was added to the same reaction vessel and refluxed for another 24 hours. The solvent evaporated and was dried under vacuum to get a white powdered precipitate. The NMR (proton—shown in FIG. 41B and phosphorus-31 not shown) and mass spec confirmed a purity of about 98%. FIG. 57 shows the phosphorous-31 NMR spectrum from this reaction-product compound. The yield of the product was 98%.

Further Examples for Coating Hard-Surfaces

Figures 42, 42A:
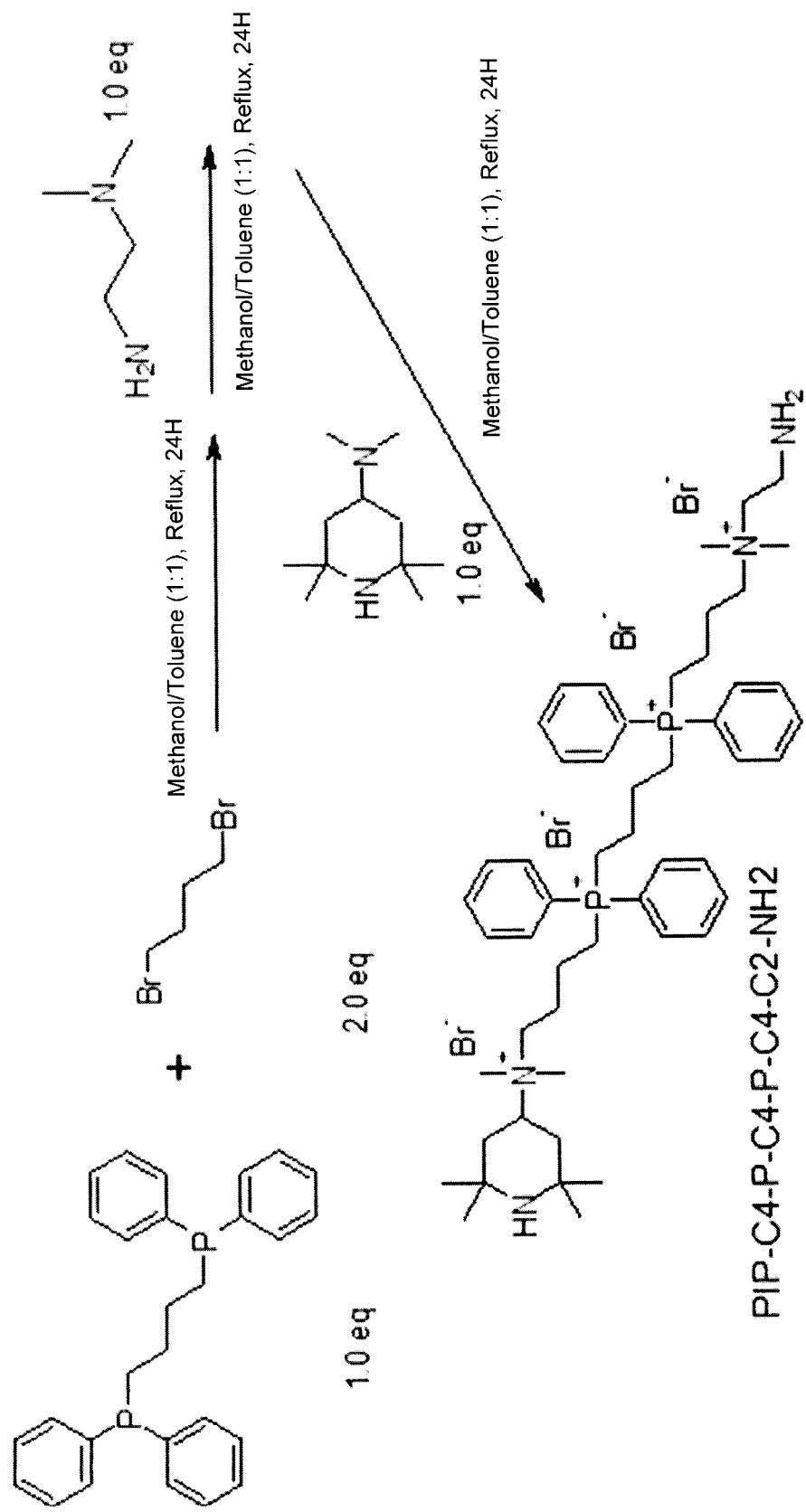
Figure 42B:
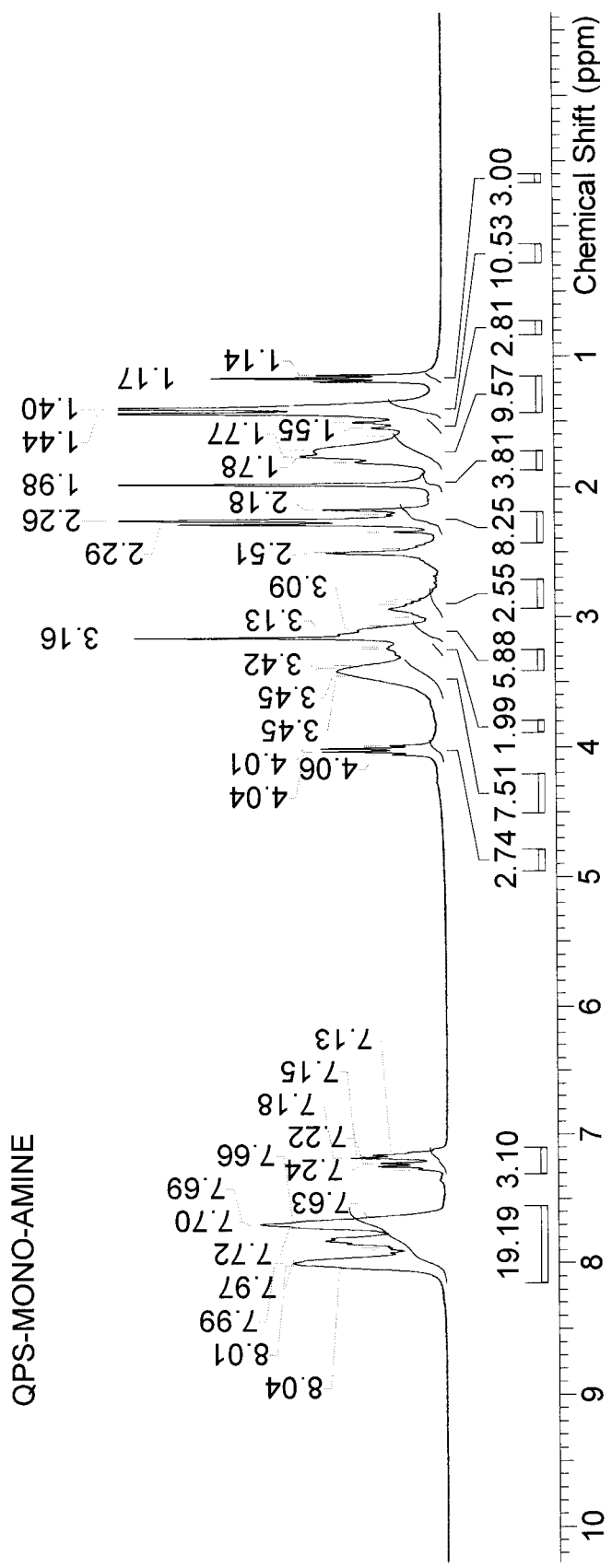
Figure 58:
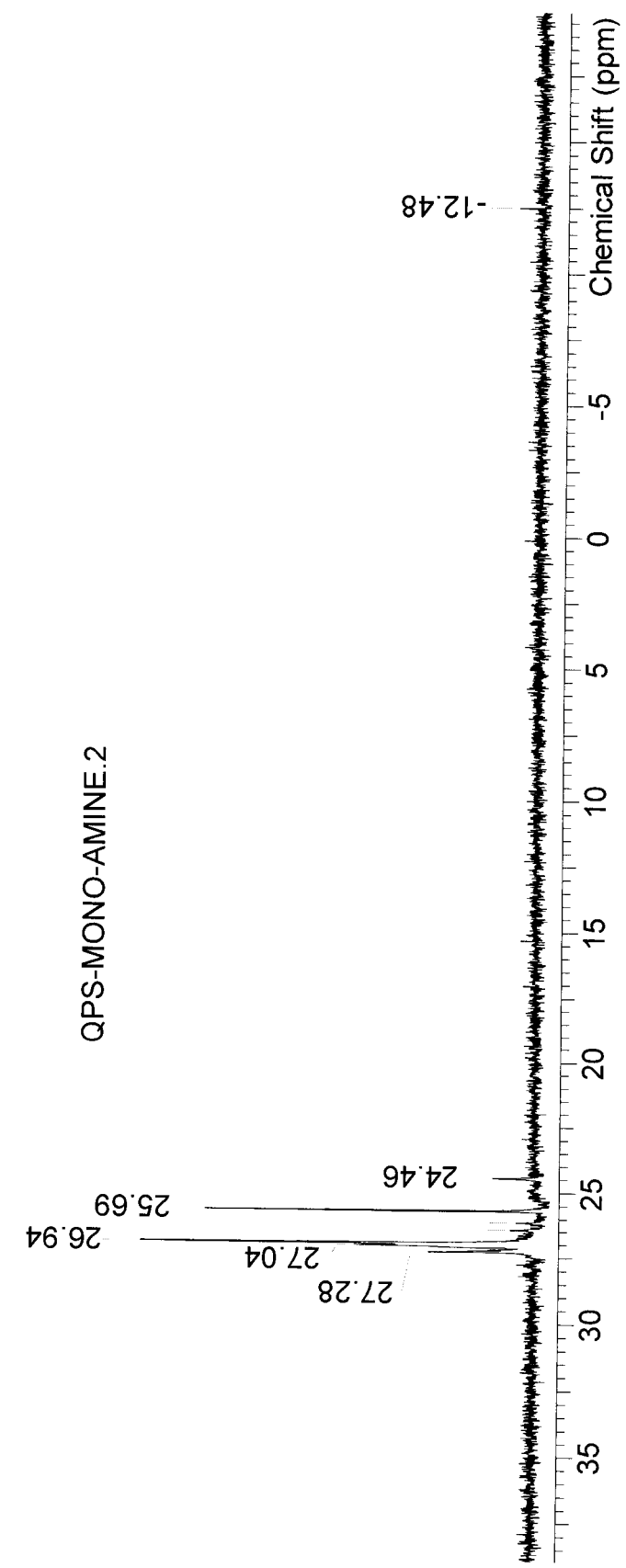
FIG. 58 is an example of a phosphorous-31 NMR spectrum from the reaction-compound shown in FIG. 42.

FIG. 42A shows another example of a set of reactions that uses a compound of Formula 2 for making a reaction-product compound with an N-halamine precursor group, a cationic center and an amine CIG. In some embodiments of the present disclosure, the reaction-product compound shown in FIG. 42A may be useful in epoxy-based coating formulations. The following were added to a reaction vessel: 1.0 eq of 1,4-Bis(diphenylphosphino)butane and 2.0 eq of 1,4-dibromobutane dissolved in toluene/methanol (1:1 v/v) which were then refluxed for 24 hours. In the same reaction vessel, a third reactant 1.0 eq of N,N-Dimethylethylenediamine was added and then refluxed for another 24 hours. Again to the same reaction vessel a fourth reactant 1.0 eq. of N,N-dimethylamino-2,2,6,6-tetramethyl-piperidine was added and the reaction vessel contents were refluxed for another 24 hours. The solvent was evaporated and dried under vacuum to produce a white precipitate. NMR (proton shown in FIG. 42B and the phosphorus-31 NMR shown in FIG. 58) and mass spec confirmed a purity of about 97%. The yield of the product was 99%.

Figure 43B:
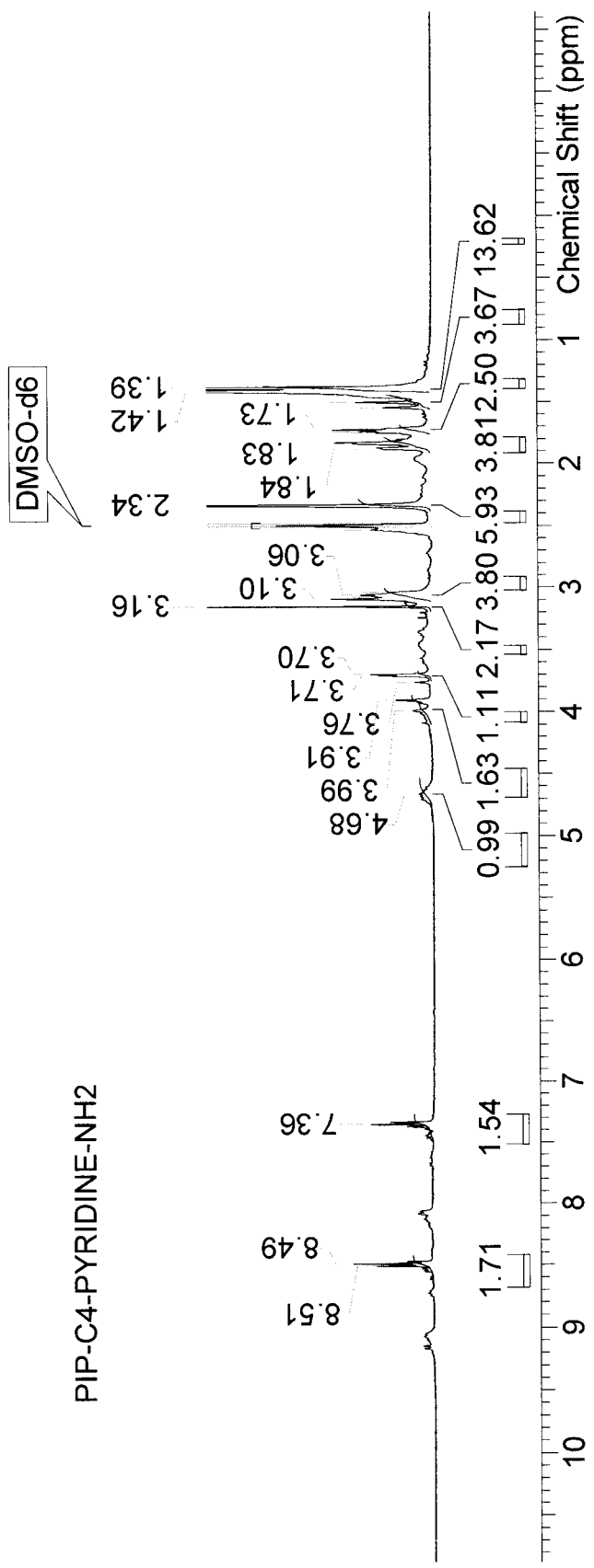

FIG. 43A shows another example of a set of reactions that uses a compound of Formula 2 for making a reaction-product compound with an N-halamine precursor group, a cationic center and an amine CIG. In some embodiments of the present disclosure, the reaction-product compound shown in FIG. 43A may be useful in epoxy-based coating formulations. The following were added to a reaction vessel: 1.0 eq of N,N-dimethylamino-2,2,6,6-tetramethyl-piperidine and 1.0 eq of 1,4-dibromobutane dissolved in methanol which were then refluxed for 12 hours. After that a third reactant 1.0 eq of 4-aminopyridine was added. The reaction mixture was stirred under reflux conditions for 24 hours in methanol. The solvent evaporated and was dried under vacuum to get a green powdered-compound. The purity of the compound checked by NMR in DMSO-d6 (FIG. 43B), which around 98%. The yield of the product was 99%.

Figures 44, 44A:
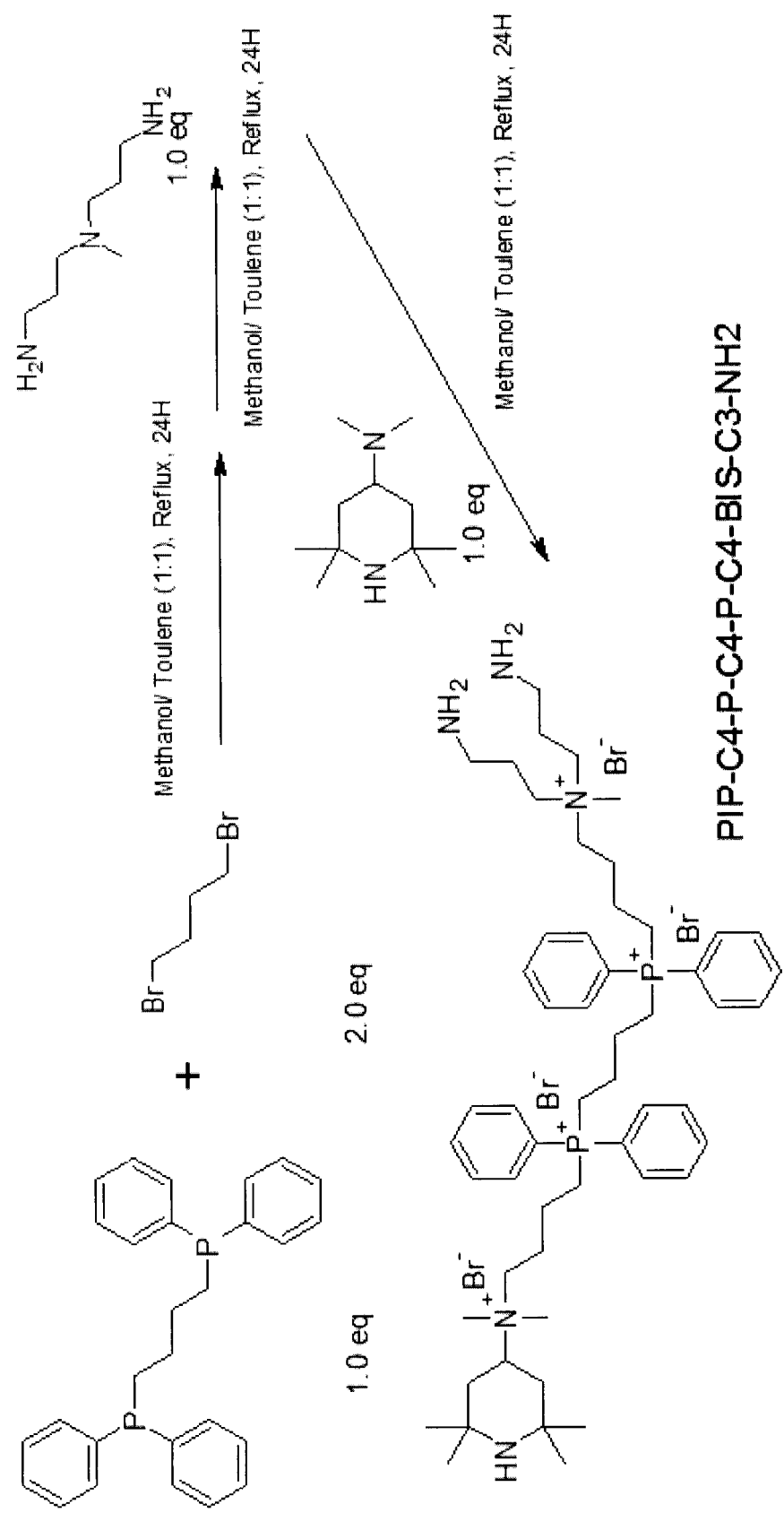

FIG. 44A shows another example of a set of reactions that uses a compound of Formula 2 for making a reaction-product compound with an N-halamine precursor group, a cationic center and two amine CIGs. In some embodiments of the present disclosure, the reaction-product compound shown in FIG. 44A may be useful in epoxy-based coating formulations. The following were added to a reaction vessel: 1.0 eq of 1,4-Bis(diphenylphosphino)butane and 2.0 eq of 1,4-dibromobutane dissolved in toluene/methanol (1:1 v/v) and refluxed for 24 hours. In the same reaction vessel, a third reactant 1.0 eq of 3,3-Diamino-N-methyldipropylamine was added and refluxed for another 24 hours. A fourth reactant 1.0 eq. of N,N-dimethylamino-2,2,6,6-tetramethyl-piperidine was added and refluxed for another 24 hours. The solvent was evaporated and dried under vacuum to get a white precipitate. The NMR (proton not shown and phosphorus-31 not shown) and mass spec confirmed a purity of about 97%. The yield of the product was 99%.

Figure 44B:
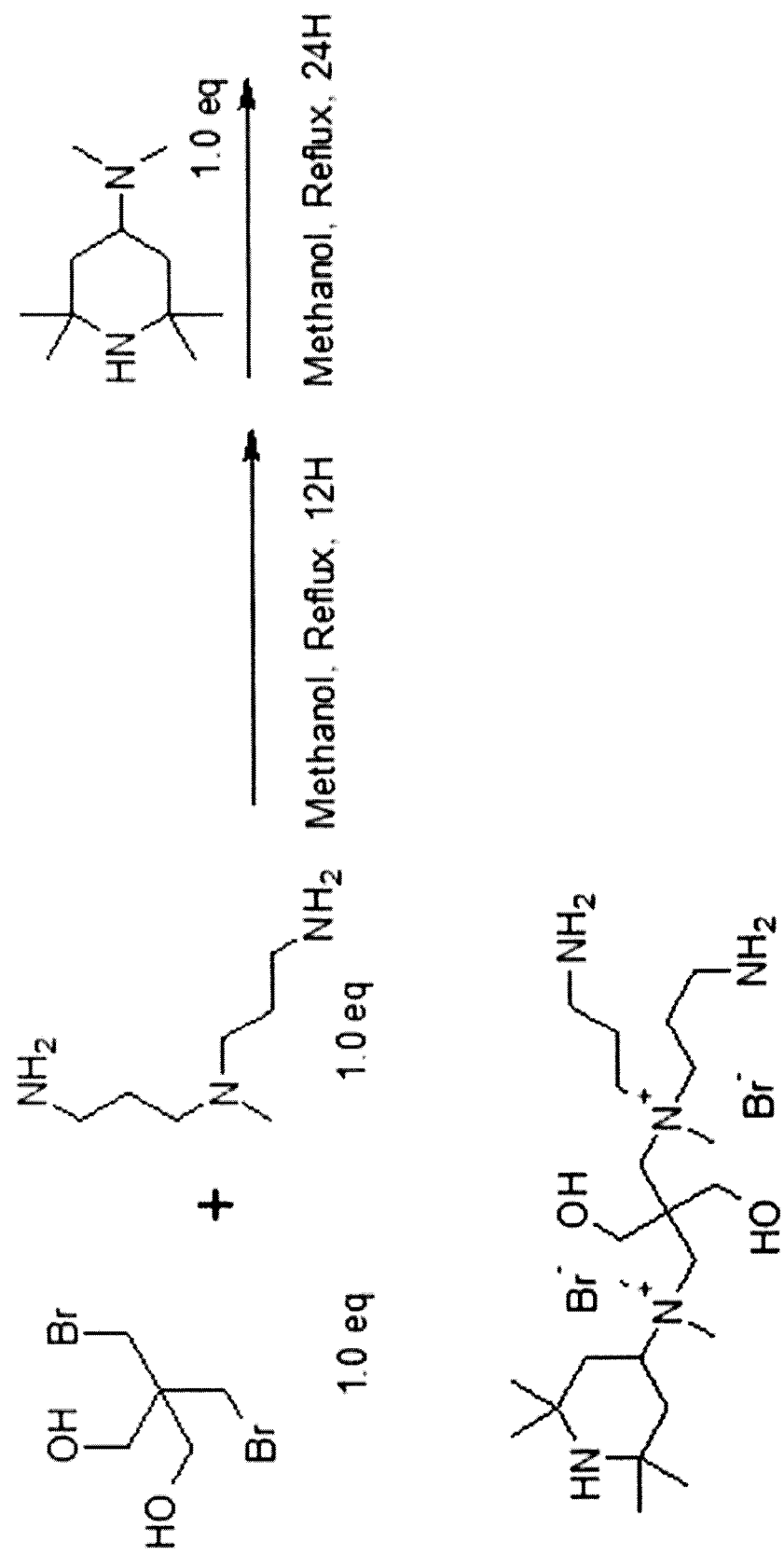
FIG. 44B shows the reactants and the reaction-product compound is referred to herein as PIP-C3(BIS-OH)-BIS-C3-NH2.

FIG. 44B shows another example of a set of reactions that uses a compound of Formula 2 for making a reaction-product compound with an N-halamine precursor group, a cationic center and two amine CIGs. In some embodiments of the present disclosure, the reaction-product compound shown in FIG. 44B may be useful in epoxy-based coating formulations. The following were added to a reaction vessel: 1.0 eq of 3,3-Diamino-N-methyldipropylamine and 1.0 eq of 2,2-bis(bromomethyl)-1,3-propanediol dissolved in methanol separately were mixed and refluxed for 12 hours. The reaction mixture evaporated. After that a third reactant 1.0 eq of N,N-dimethylamino-2,2,6,6-tetramethyl-piperidine was added. The reaction mixture was stirred under reflux condition for 24 hours in methanol. The solvent evaporated and dried under vacuum to form a clear gel. The purity of the compound checked by NMR in DMSO (not shown), which was around 98%. The yield of the product was 99%.

Figure 44C:
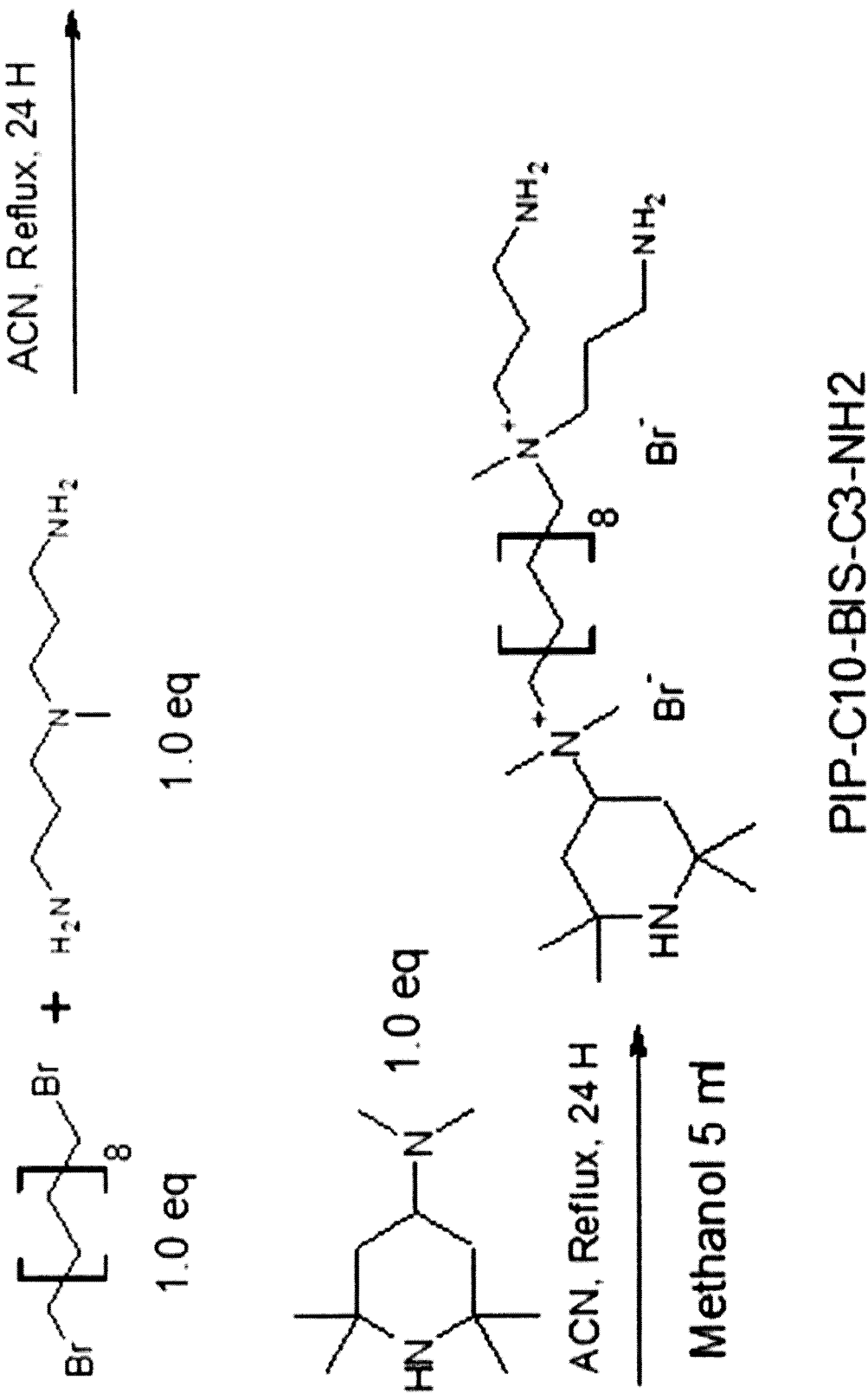
FIG. 44C shows the reactants and the reaction-product compound is referred to herein as PIP-C10-BIS-C3-NH2.

FIG. 44C shows another example of a set of reactions that uses a compound of Formula 2 for making a reaction-product compound with an N-halamine precursor group, a cationic center and two amine CIGs. In some embodiments of the present disclosure, the reaction-product compound shown in FIG. 44C may be useful in epoxy-based coating formulations. The following were added to a reaction vessel: 1.0 eq of 3,3-Diamino-N-methyldipropylamine and 1.0 eq of 1,10-dibromodecane dissolved in acetonitrile separately were mixed and refluxed for 24 hours. The reaction mixture evaporated and appeared as an orange oil, which was dissolved again by adding acetonitrile/methanol mixture (8:2 v/v) clear solution appeared. After that a third reactant 1.0 eq of N,N-dimethylamino-2,2,6,6-tetramethyl-piperidine was added. The reaction mixture was stirred under reflux condition for 24 hours in acetonitrile/methanol. The solvent was evaporated and dried under vacuum to form an off-white solid. The purity of the compound checked by NMR in DMSO (not shown), which was around 98%. The yield of the product was 99%.

Figures 45, 45A:
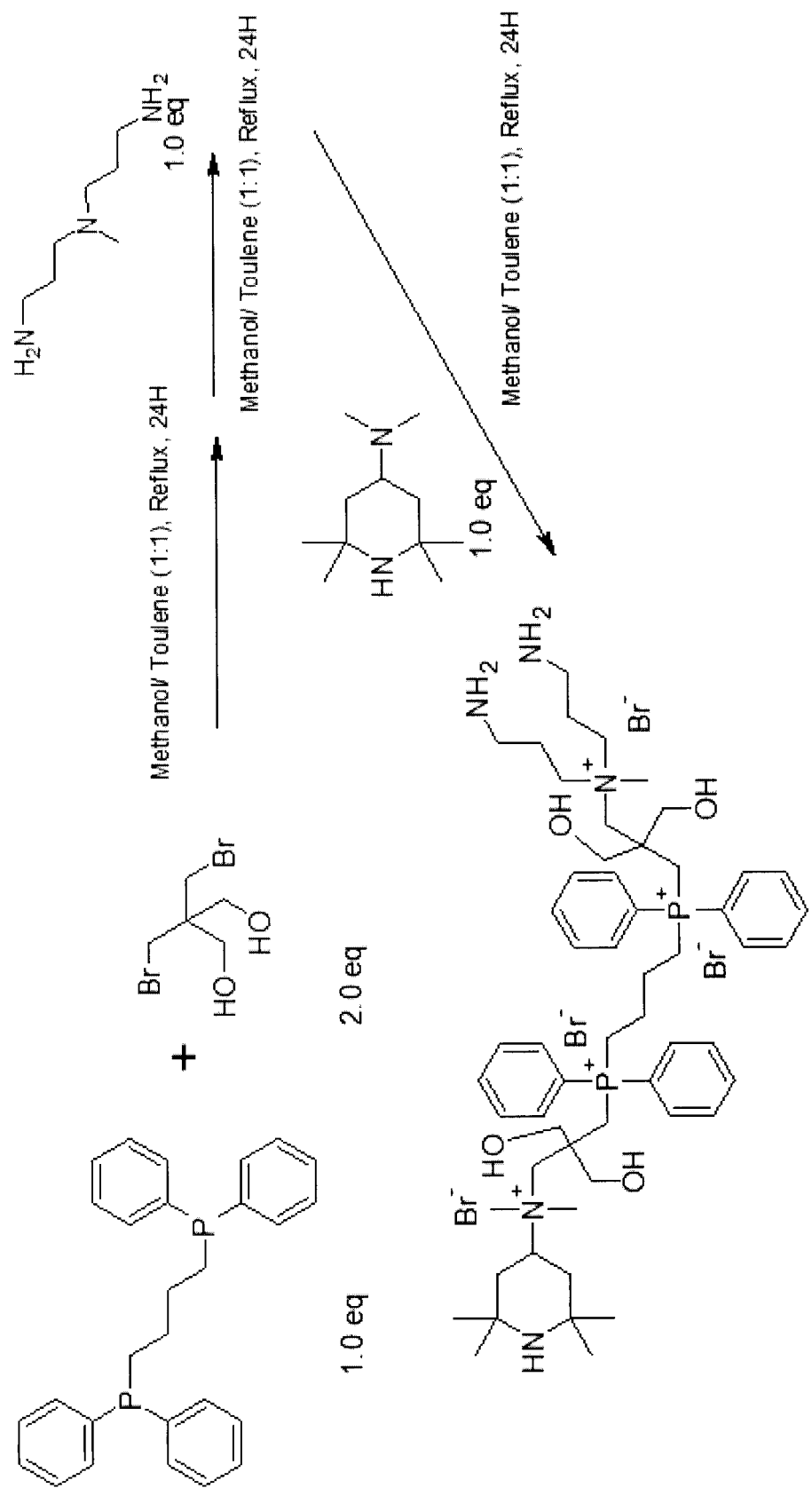

FIG. 45A shows another example of a set of reactions that uses a compound of Formula 2 for making a reaction-product compound with an N-halamine precursor group, a cationic center and two amine CIGs. In some embodiments of the present disclosure, the reaction-product compound shown in FIG. 45A may be useful in epoxy-based coating formulations. The following were added to a reaction vessel: 1.0 eq of 1,4-Bis(diphenylphosphino)butane and 2.0 eq of 2,2-bis(bromomethyl)-1,3-propanediol dissolved in toluene/methanol (1:1 v/v) and refluxed for 24 hours. In the same reaction vessel, a third reactant 1.0 eq of 3,3-Diamino-N-methyldipropylamine was added and refluxed for another 24 hours. Again to the same reaction vessel a fourth reactant 1.0 eq. of N,N-dimethylamino-2,2,6,6-tetramethyl-piperidine was added and refluxed for another 24 hours. The solvent evaporated and dried under vacuum to get a clear gel. The NMR (proton—not shown) confirmed a purity of about 97%. The yield of the product was 99%.

Figure 45B:
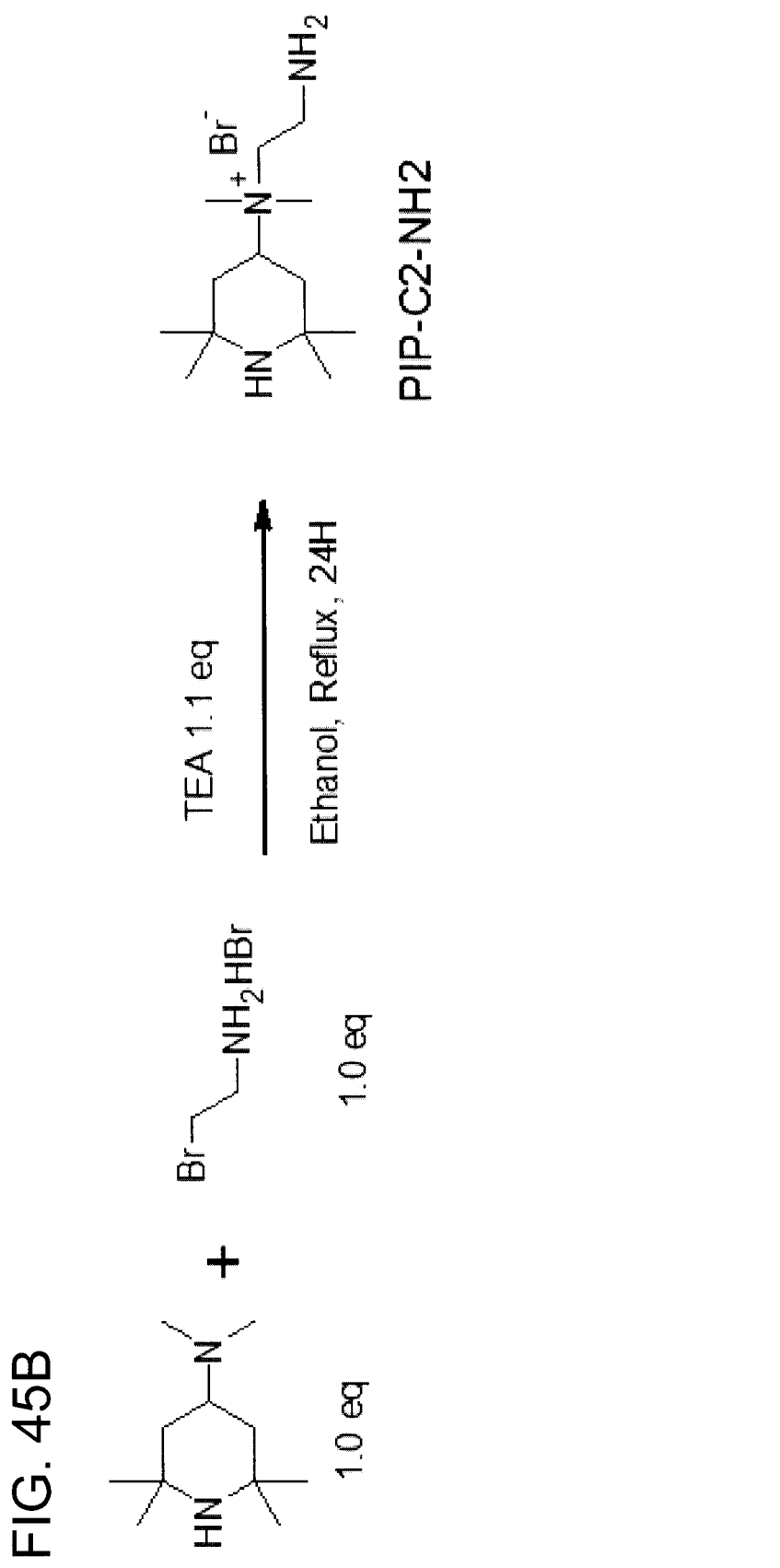
FIG. 45B shows the reactants and the reaction-product compound is referred to herein as PIP-C2-NH2.
Figure 45C:
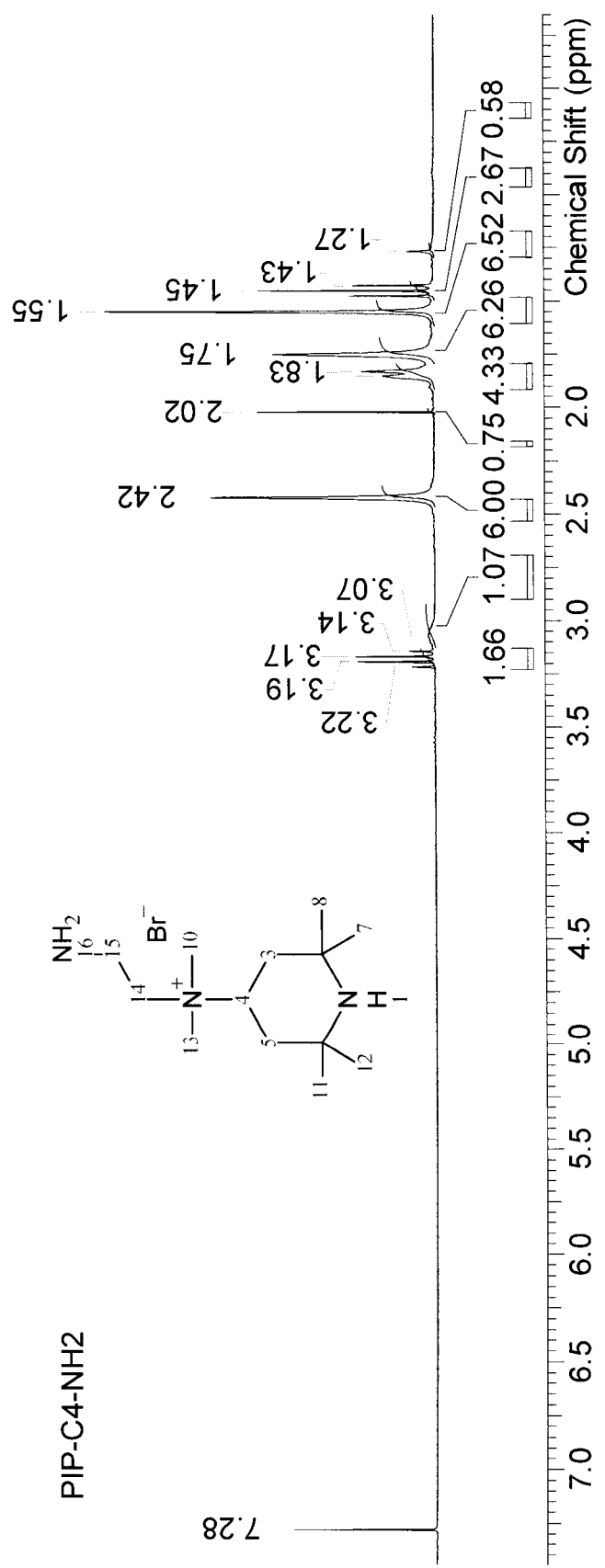
FIG. 45C shows an example of NMR spectroscopy data of the reaction-product compound of FIG. 45B.

FIG. 45B shows another example of a set of reactions that uses a compound of Formula 2 for making a reaction-product compound with an N-halamine precursor group, a cationic center and an amine CIGs. In some embodiments of the present disclosure, the reaction-product compound shown in FIG. 45A may be useful in epoxy-based coating formulations. The following were added to a reaction vessel: 1.0 eq of N,N-dimethylamino-2,2,6,6-tetramethyl-piperidine, 1.0 eq of 2-bromoethyleneamine hydrobromide and 1.1 eq of triethylamine (TEA) dissolved in ethanol which were then refluxed for 24 hours. The solvent was evaporated and dried under vacuum. A white crystalline product was washed with ethyl acetate and filtered to remove triethylamine hydrobromide salts. The purity of the compound checked by NMR in CDCl3 (FIG. 45C), which around 98%. The yield of the product was 99%.

Figure 46:
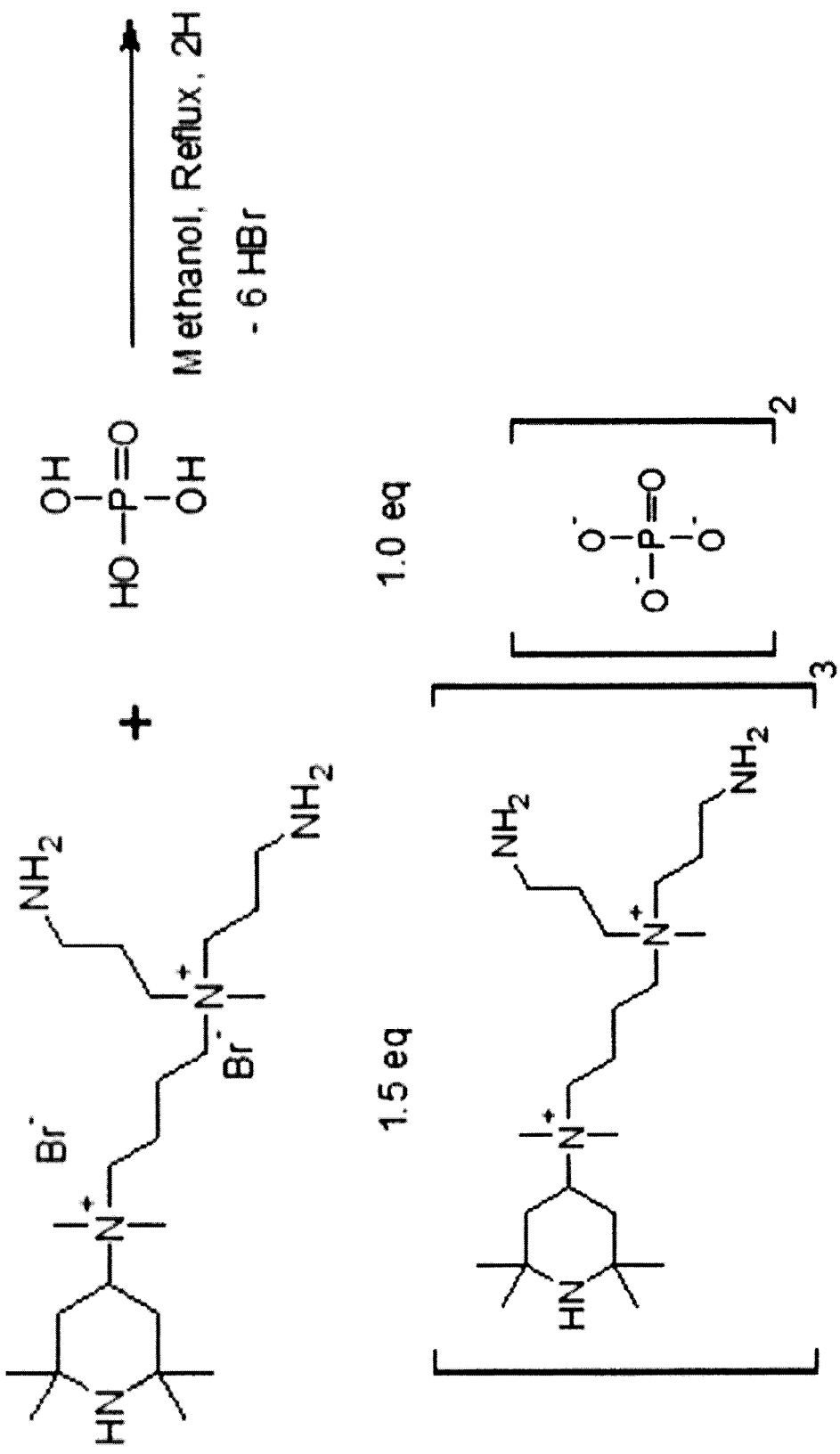
Figure 46B:
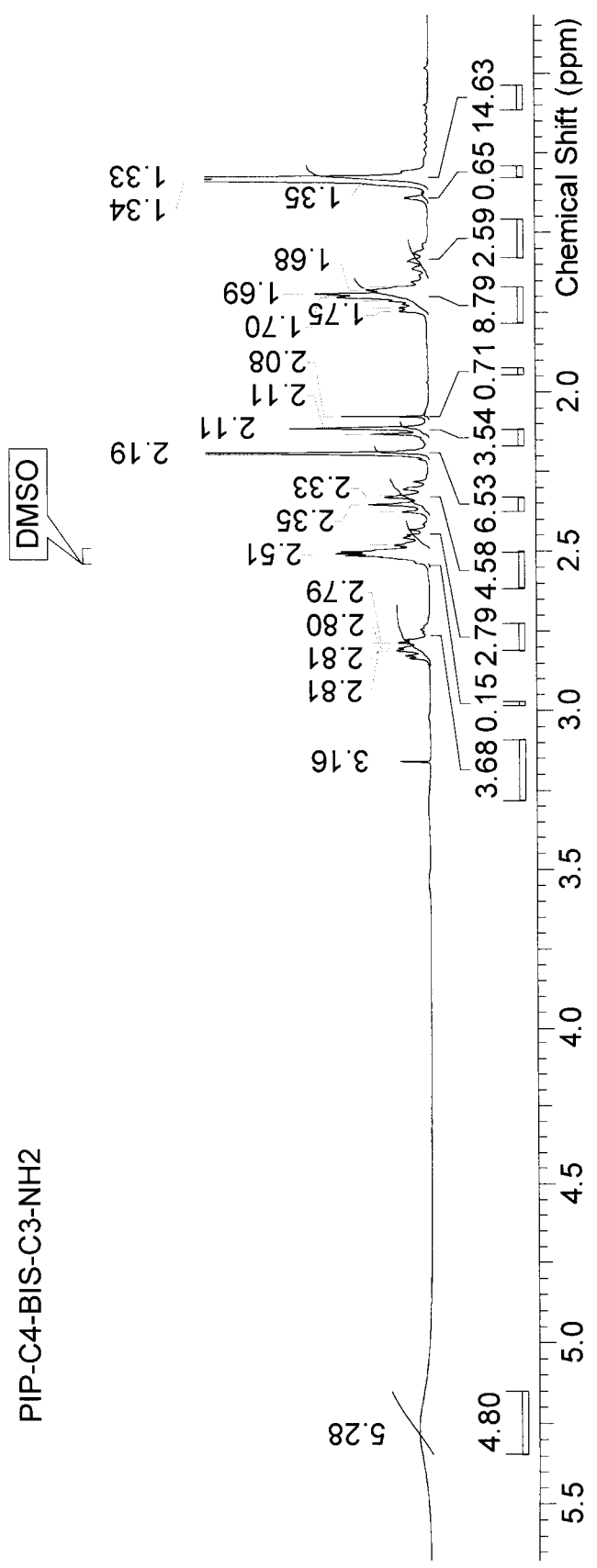

FIG. 46A shows another example of a set of reactions that uses a compound of Formula 2 for making a reaction-product compound with an N-halamine precursor group, a cationic center and two amine CIGs. In some embodiments of the present disclosure, the reaction-product compound shown in FIG. 46A may be useful in epoxy-based coating formulations. The following were added to a reaction vessel: 1.5 eq of PIP-C4-BIS-C3-NH2 and 1.0 eq of phosphoric acid dissolved in methanol, mixed and refluxed for 2 hours. The solvent of reaction mixture was evaporated to get a white gel and kept under a high vacuum for further drying. The purity was checked by proton NMR (99%) (FIG. 46B) and yield was 99%.

Figures 47, 47A:
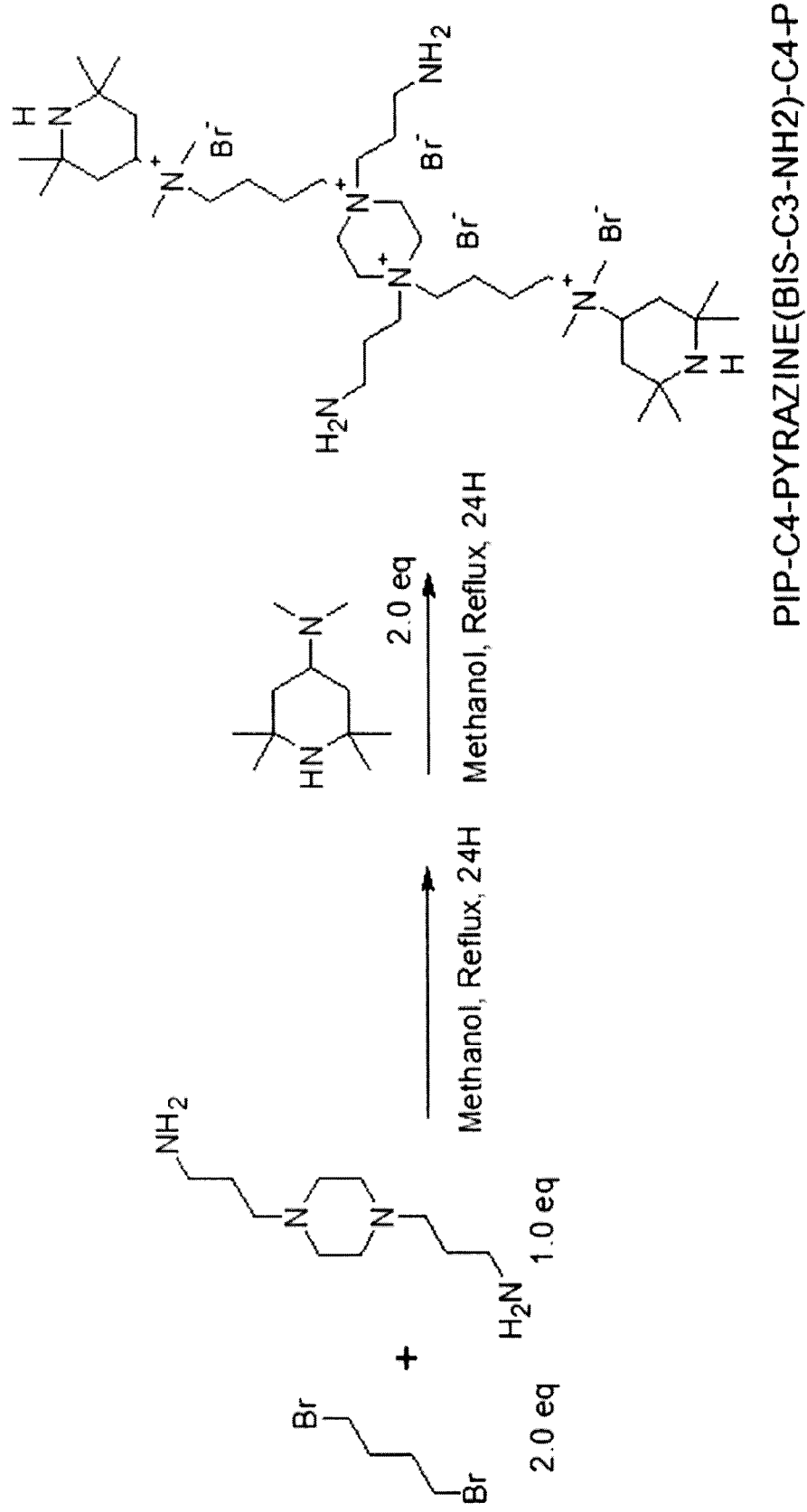
Figure 47B:
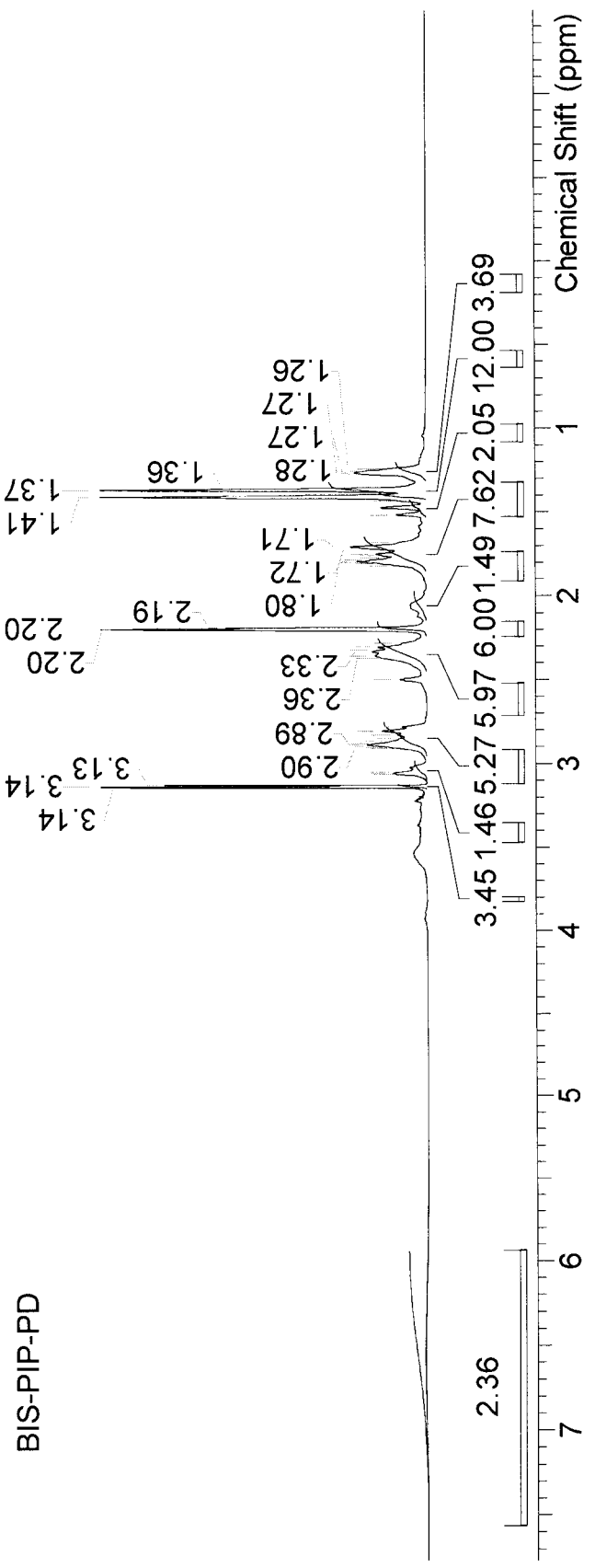

FIG. 47A shows another example of a set of reactions that uses a compound of Formula 2 for making a reaction-product compound with an N-halamine precursor group, a cationic center and two amine CIGs. In some embodiments of the present disclosure, the reaction-product compound shown in FIG. 47A may be useful in epoxy-based coating formulations. The following were added to a reaction vessel: 1.0 eq of 1,4-Bis(3-aminopropyl)piperazine, 2.0 eq of 1,4-dibromobutane dissolved in methanol separately, mixed and refluxed for 24 hours. After that a third reactant 2.0 eq of N,N-dimethylamino-2,2,6,6-tetramethyl-piperidine was added. The reaction mixture was stirred under reflux condition for 24 hours in methanol. The solvent was evaporated and dried under vacuum to form a yellow gel. The purity of the compound checked by proton NMR in DMSO (FIG. 47B), which around 98%. The yield of the product was 99%.

Figures 48, 48A:
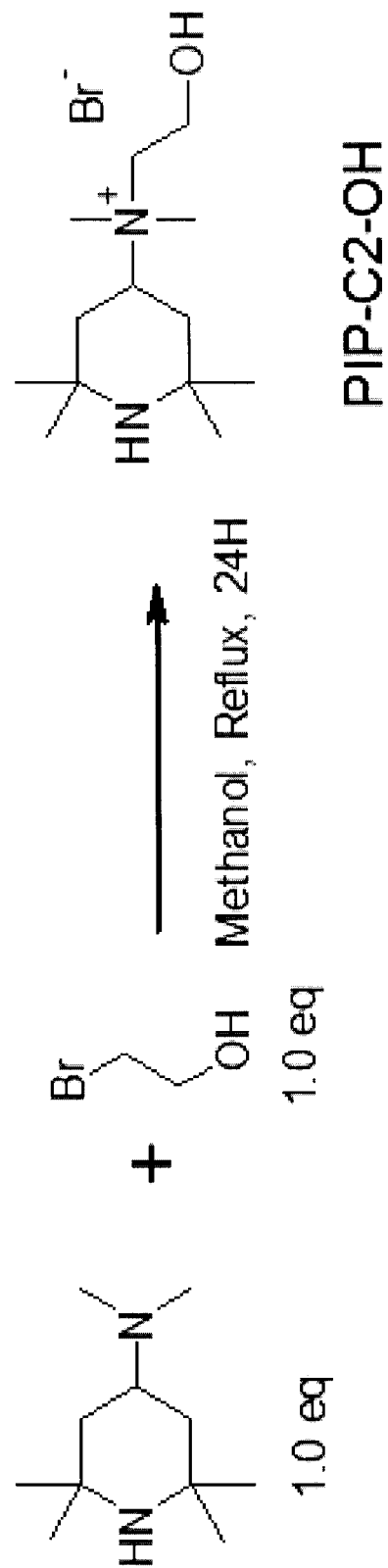
Figure 48B:
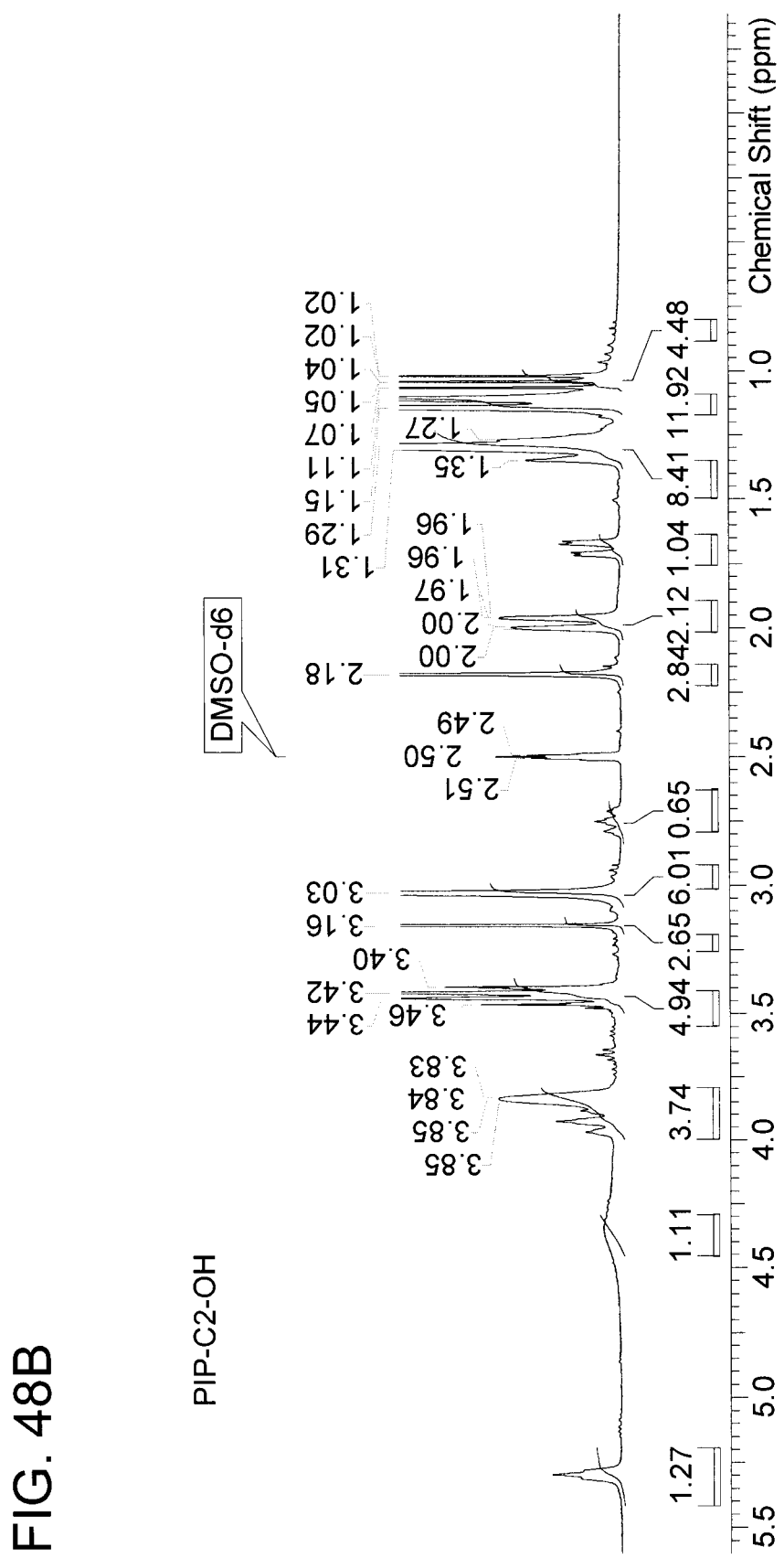

FIG. 48A shows another example of a set of reactions that uses a compound of Formula 2 for making a reaction-product compound with an N-halamine precursor group, a cationic center and a hydroxyl CIG. In some embodiments of the present disclosure, the reaction-product compound shown in FIG. 48A may be useful in epoxy-based coating formulations. The following were added to a reaction vessel: 1.0 eq of N,N-dimethylamino-2,2,6,6-tetramethyl-piperidine and 1.0 eq of 2-bromoethanol dissolved in methanol and refluxed for 24 hours. The solvent was evaporated and dried under vacuum. The purity of the compound checked by NMR in DMSO (FIG. 48B), which around 98%. The yield of the product was 99%.

Figures 49, 49A:
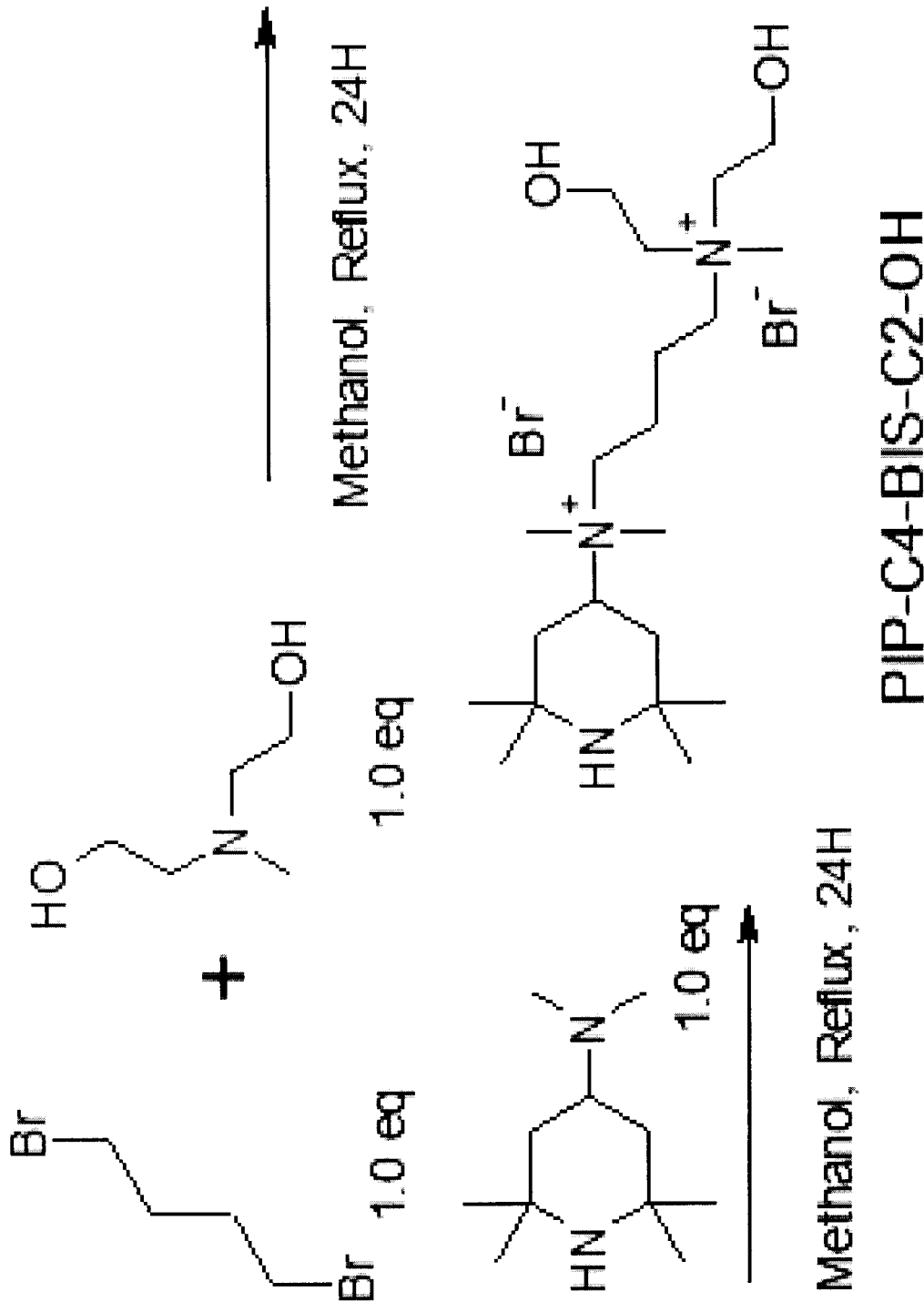

FIG. 49A shows another example of a set of reactions that uses a compound of Formula 2 for making a reaction-product compound with an N-halamine precursor group, a cationic center and two hydroxyl CIGs. In some embodiments of the present disclosure, the reaction-product compound shown in FIG. 49A may be useful in epoxy-based coating formulations. The following were added to a reaction vessel: 1.0 eq of 2,2'-Methyliminodiethanol and 1.0 eq of 1,4-dibromobutane dissolved in methanol separately, mixed and refluxed for 24 hours. After that a third reactant 1.0 eq of N,N-dimethylamino-2,2,6,6-tetramethyl-piperidine was added. The reaction mixture was stirred under reflux condition for 24 hours in methanol. The solvent was evaporated and dried under vacuum to form a clear gel. The purity of the compound checked by NMR in D$_2$O, which around 98%. The yield of the product was 99%.

Figure 49B:
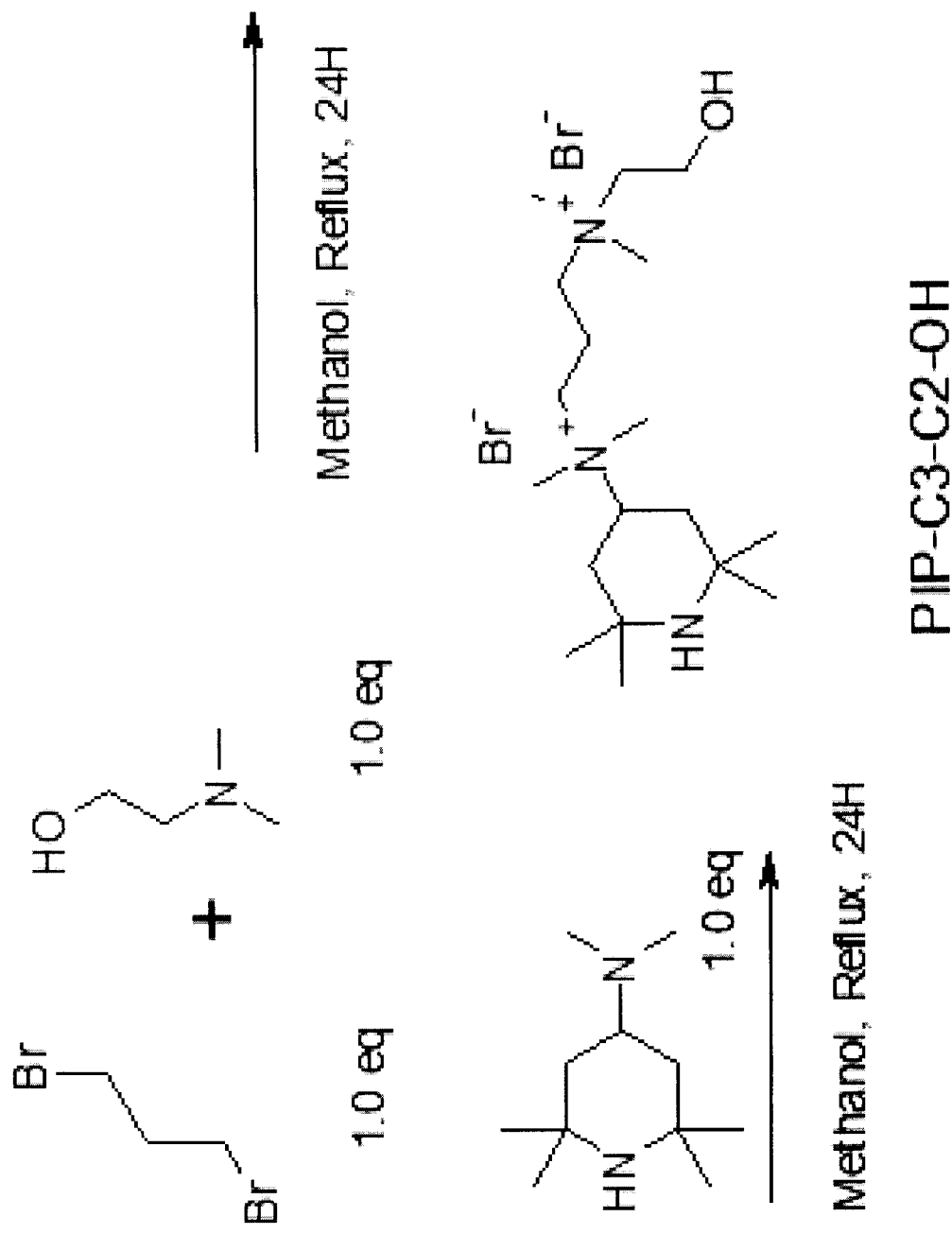
Figure 49C:
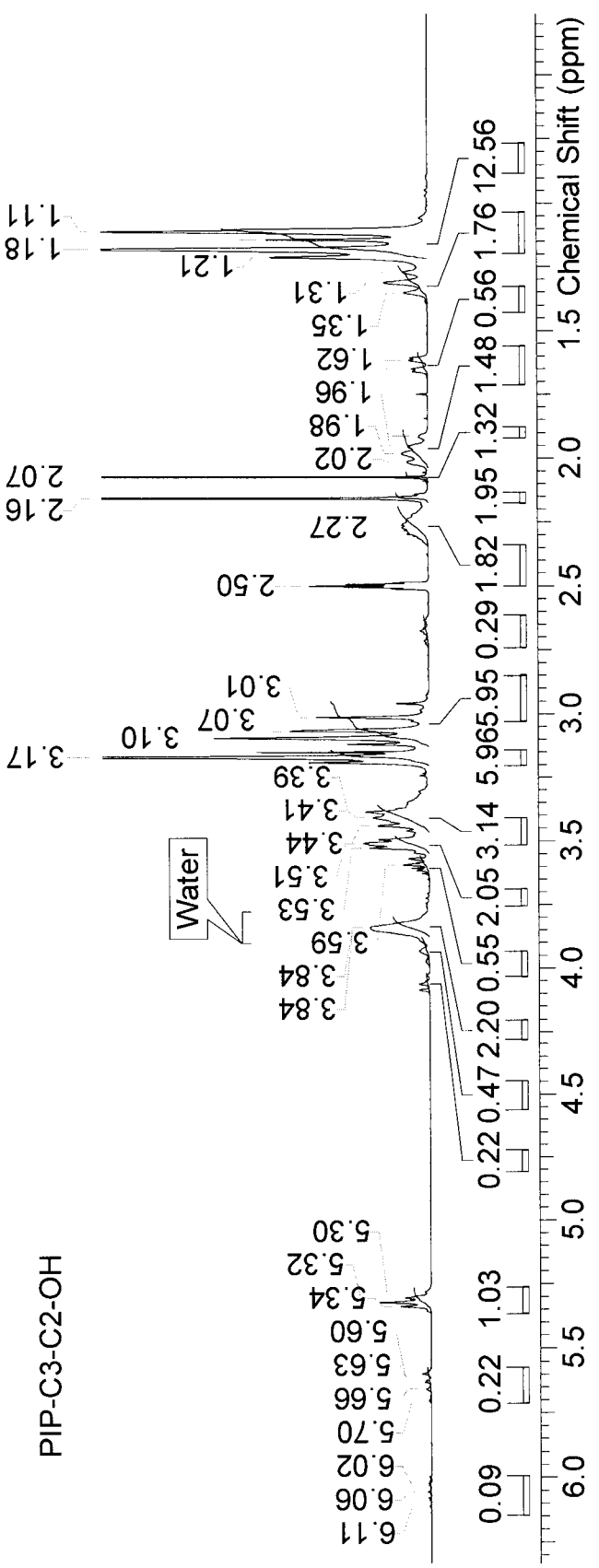

FIG. 49B shows another example of a set of reactions that uses a compound of Formula 2 for making a reaction-product compound with an N-halamine precursor group, a cationic center and two hydroxyl CIGs. In some embodiments of the present disclosure, the reaction-product compound shown in FIG. 49B may be useful in epoxy-based coating formulations. The following were added to a reaction vessel: 1.0 eq of N,N-dimethylethanolamine, 1.0 eq of 1,3-dibromopropane dissolved in methanol separately, mixed and refluxed for 24 hours. After that a third reactant 1.0 eq of N,N-dimethylamino-2,2,6,6-tetramethyl-piperidine was added. The reaction mixture was stirred under reflux condition for 24 hours in methanol. The solvent was evaporated and dried under vacuum to form as clear gel. The purity of the compound checked by NMR in DMSO (FIG. 49C), which around 98%. The yield of the product was 99%.

Figure 50:
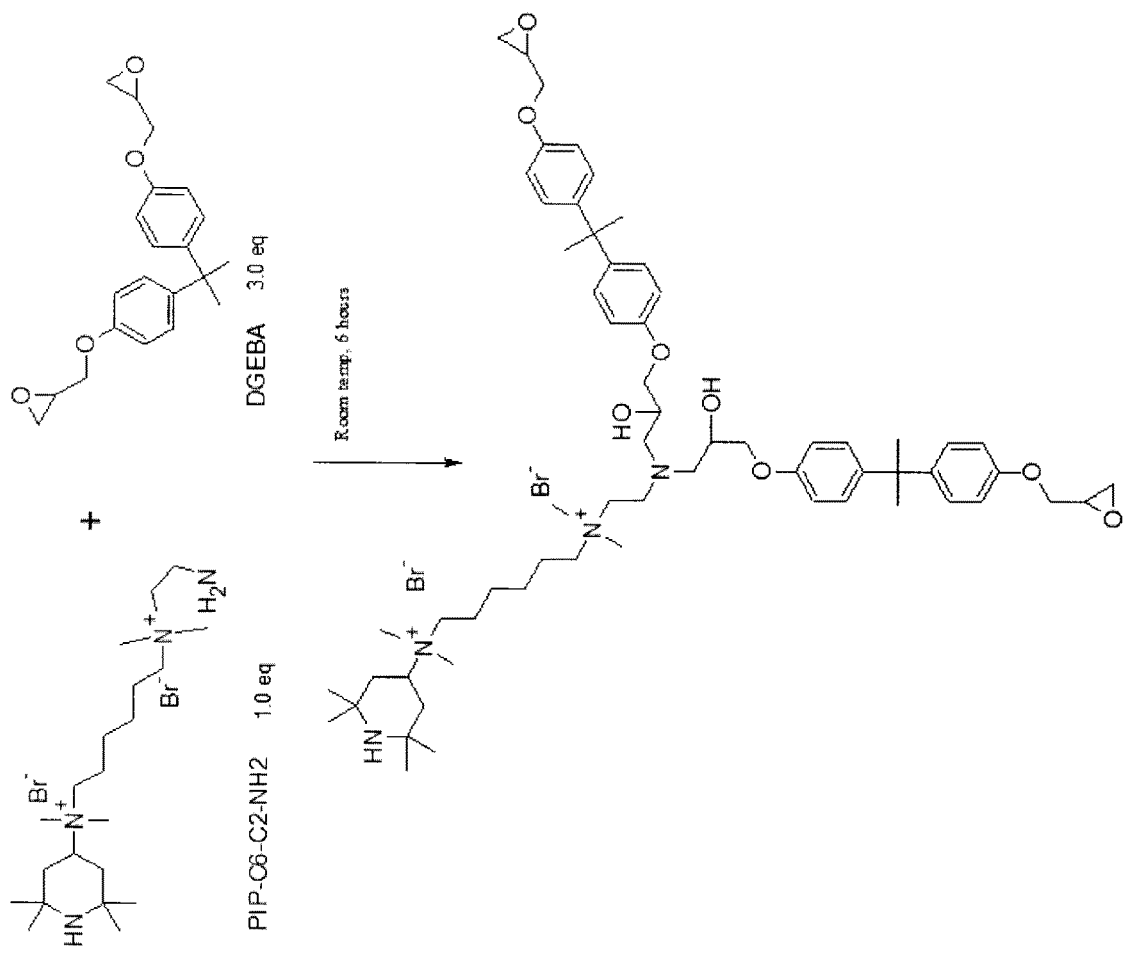
FIG. 50 is an example of another synthesis reaction series for producing reaction-product compounds with two epoxide CIGs and two hydroxyl CIGs according to an embodiment of the present disclosure.

FIG. 50 shows another example of a set of reactions that uses a compound of Formula 2 for making a reaction-product compound with an N-halamine precursor group, a cationic center and two epoxide CIGs. In some embodiments of the present disclosure, the reaction-product compound shown in FIG. 50 may be useful in epoxy-based coating formulations. The following were added to a reaction vessel: 1.0 eq of PIP-C6-C2-NH2, 3 eq of DEGBA dissolved in methanol and stirred at room temperature for 6 hours. The solvent was evaporated and dried under high vacuum to form crystalline light yellow hygroscopic solid. Electrospray ionization mass spectroscopy results demonstrated the expected mass, less one bromide ion. The yield calculated was 99%.

Figure 51B:
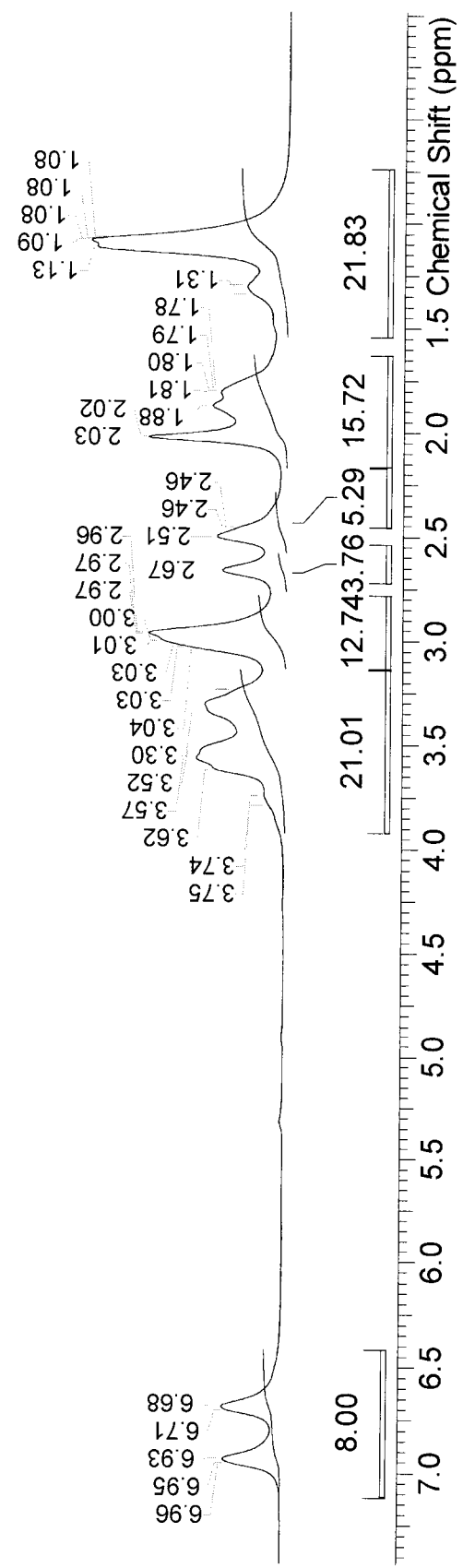

FIG. 51A shows another example of a set of reactions that uses a compound of Formula 2 for making a reaction-product compound with an N-halamine precursor group, a cationic center and four epoxide CIGs. In some embodiments of the present disclosure, the reaction-product compound shown in FIG. 51A may be useful in epoxy-based coating formulations. The following were added to a reaction vessel: 1.0 eq of N,N-dimethylamino-2,2,6,6-tetramethyl-piperidine, 1.0 eq of 1,4-dibromobutane dissolved in methanol separately, mixed and refluxed for 12 hours. After that a third reactant 0.5 eq of 4,4'-Methylenebis(N,N-diglycidylaniline) was added. The reaction mixture was stirred under reflux conditions for 24 hours in methanol. The solvent was evaporated and dried under vacuum to form a clear gel. The purity of the compound checked by NMR in DMSO (FIG. 51B), which around 98%. The yield of the product was 99%.

Figure 52:
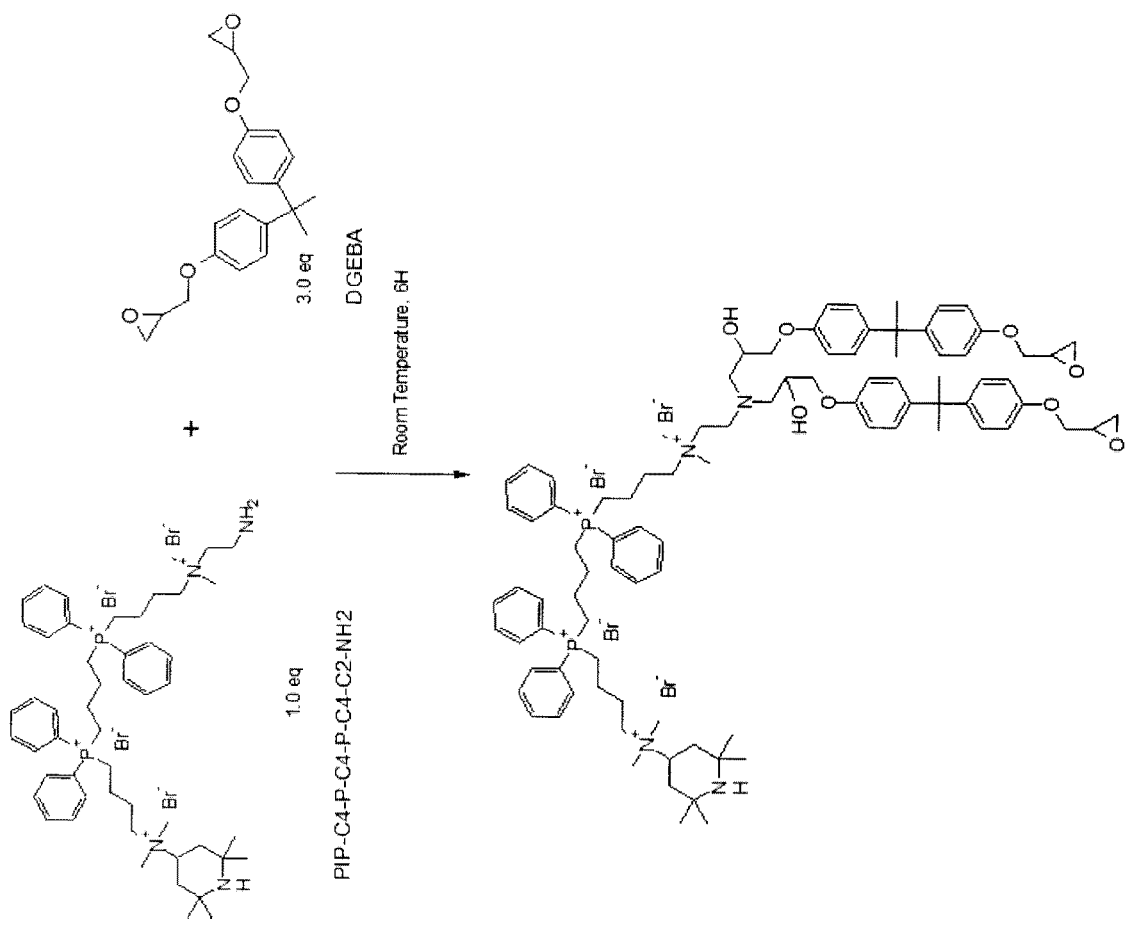
FIG. 52 is an example of another synthesis reaction series for producing reaction-product compounds with two epoxide CIGs and two hydroxyl CIGs according to an embodiment of the present disclosure.
Figure 53:
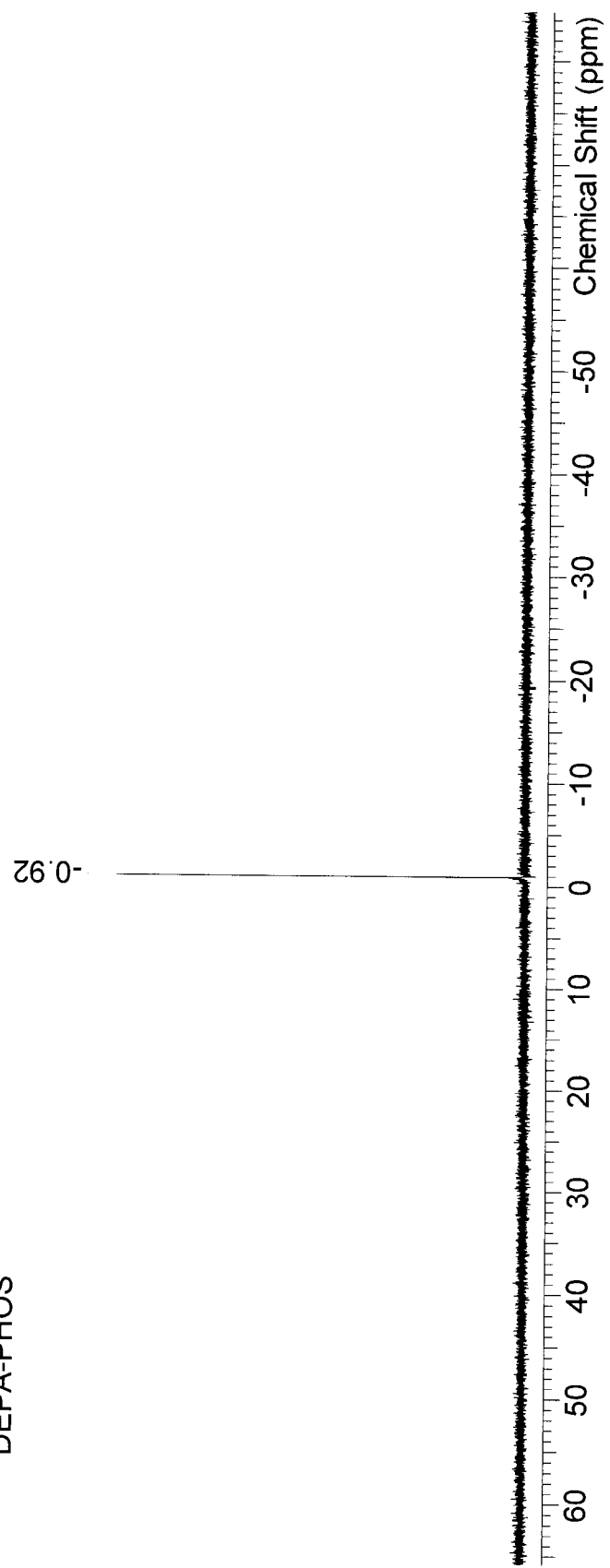
FIG. 53 is an example of a phosphorous-31 NMR spectrum from the reaction-compound shown in FIG. 2.

FIG. 52 shows another example of a set of reactions that uses a compound of Formula 2 for making a reaction-product compound with an N-halamine precursor group, a cationic center and four epoxide CIGs. In some embodiments of the present disclosure, the reaction-product compound shown in FIG. 52 may be useful in epoxy-based coating formulations. The following were added to a reaction vessel: 1.0 eq of PIP-C4-P-C4-P-C4-C2-NH2 and 3 eq of DEGBA was dissolved in methanol and stirred at room temperature for 6 hours. The solvent was evaporated and dried under high vacuum to form a crystalline, white hygroscopic solid. NMR data was confirmatory of a 1:2 ratio of the reaction-product compound to DEGBA (not shown). Electrospray ionization mass spectroscopy results demonstrated the expected mass, less one bromide ion. The yield calculated was 99%.

I claim:

1. A process for making a reaction-product compound, the process comprising a step of:
   a. reacting a reactant compound of Formula 1:

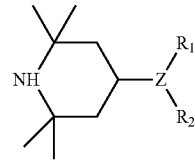

(1)

wherein
Z is either N or Y,
when Z is N then R1 and R2 are each independently selected from a group of methyl, ethyl or n-propyl; and
when Z is Y then R1 and R2 are both nil and Y is selected from Cl, Br and I, with one or more further reactants,
wherein the one or more further reactants comprise a coating incorporation group that is one of: a vinyl group, a vinyl acetate group, an acrylate group, a methacrylate group, a methyl methacrylate group, an acrylamide group, a styrenic group, a hydroxyl group, an alkyloxy group, an aldehyde group, a ketone group, a carboxy group, an epoxide, an amine group, an imine group, an imide group, an azide group, an amide group, a cyanate group, an isocyanate group, a carbamide group, a thiourea, a thiol group, a sulfinic group, a sulfone group, a sulfoxide group or combinations thereof; and
wherein the reaction-product compound is a monomer comprising at least one cyclic N-halamine precursor group, at least one cationic nitrogen center and the at least one coating incorporation group on a substituent of the cationic nitrogen center, and wherein the at least one coating incorporation group makes the reaction-product compound incorporatable into a polymer.

2. The process of claim 1, wherein the polymer is one of: an acetate polymer; a vinyl ester polymer a vinyl acetate homopolymer; an acrylate polymer; a melamine; a modified melamine; a urethane polymer; a polyurethane polymer; an aliphatic urethane polymer; a polyesters; a self-crosslinking polyesters; an epoxide polymer; a fluoropolymer; a silicone or silicone derivative polymer; a polyethylene; a polypropylene; a polyvinyl chloride; a polyamide; a polybutylene; a poly(buta-1,3-diene); a polysulfone; a precursor of any of the polymers listed above and any combinations thereof.

3. The process of claim 2, wherein the vinyl ester polymer is a vinyl acetate polymer.

4. The process of claim 2, wherein the acrylate polymer is a methacrylate polymer.

5. The process of claim 2, wherein the epoxide polymer is an epoxide ester polymer.

6. The process of claim 1, wherein the compound is of Formula 2:

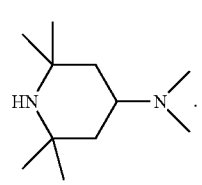
(2)
7. The process of claim 1, wherein the compound is of Formula 3:
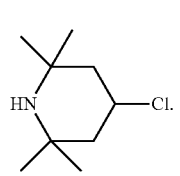
(3)
* * * * *